United States Patent
Bolli et al.

(10) Patent No.: US 12,304,902 B2
(45) Date of Patent: May 20, 2025

(54) HYDROXYHETEROCYCLOALKANE-CARBAMOYL DERIVATIVES

(71) Applicant: Idorsia Pharmaceuticals Ltd, Allschwil (CH)

(72) Inventors: Martin Bolli, Allschwil (CH); John Gatfield, Allschwil (CH); Corinna Grisostomi, Allschwil (CH); Lubos Remen, Allschwil (CH); Christoph Sager, Allschwil (CH); Cornelia Zumbrunn, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 18/264,751

(22) PCT Filed: Feb. 8, 2022

(86) PCT No.: PCT/EP2022/052948
§ 371 (c)(1),
(2) Date: Aug. 8, 2023

(87) PCT Pub. No.: WO2022/171594
PCT Pub. Date: Aug. 18, 2022

(65) Prior Publication Data
US 2024/0124427 A1    Apr. 18, 2024

(30) Foreign Application Priority Data
Feb. 9, 2021    (WO) ............... PCT/EP2021/053084

(51) Int. Cl.
*C07H 19/12*    (2006.01)
*C07D 405/14*    (2006.01)

(52) U.S. Cl.
CPC ........... *C07D 405/14* (2013.01); *C07H 19/12* (2013.01)

(58) Field of Classification Search
None
See application file for complete search history.

(56) References Cited

U.S. PATENT DOCUMENTS

| | | |
|---|---|---|
| 2014/0099319 A1 | 4/2014 | Traber |
| 2020/0155586 A1 | 5/2020 | Zomer et al. |
| 2022/0281855 A1 | 9/2022 | Bolli et al. |
| 2022/0306674 A1 | 9/2022 | Bolli et al. |
| 2022/0315619 A1 | 10/2022 | Bolli et al. |
| 2022/0324847 A1 | 10/2022 | Bolli et al. |
| 2023/0295182 A1 | 9/2023 | Bolli et al. |
| 2023/0348442 A1 | 11/2023 | Bolli et al. |

FOREIGN PATENT DOCUMENTS

| | | |
|---|---|---|
| WO | WO 02/057284 A1 | 7/2002 |
| WO | WO 2005/113568 A1 | 12/2005 |
| WO | WO 2005/113569 A1 | 12/2005 |
| WO | WO 2014/067986 A1 | 5/2014 |
| WO | WO 2014/078655 A1 | 5/2014 |
| WO | WO 2016/120403 A1 | 8/2016 |
| WO | WO 2017/007689 A1 | 1/2017 |
| WO | WO 2018/011094 A1 | 1/2018 |
| WO | WO 2018/209255 A1 | 11/2018 |
| WO | WO-2018209276 A1 * | 11/2018 ......... A61K 31/4439 |
| WO | WO 2019/067702 A1 | 4/2019 |
| WO | WO 2019/075045 A1 | 4/2019 |
| WO | WO 2019/089080 A1 | 5/2019 |
| WO | WO 2020/078807 A1 | 4/2020 |
| WO | WO 2020/078808 A1 | 4/2020 |
| WO | WO 2020/104335 A1 | 5/2020 |
| WO | WO 2020/210308 A1 | 10/2020 |
| WO | WO 2021/001528 A1 | 1/2021 |

(Continued)

OTHER PUBLICATIONS

U.S. Appl. No. 17/633,895, filed Feb. 8, 2022 (371(c) Date), Bolli et al.

(Continued)

*Primary Examiner* — Traviss C McIntosh, III
(74) *Attorney, Agent, or Firm* — Hoxie & Associates LLC

(57) ABSTRACT

The present invention relates to compounds of Formula (I)

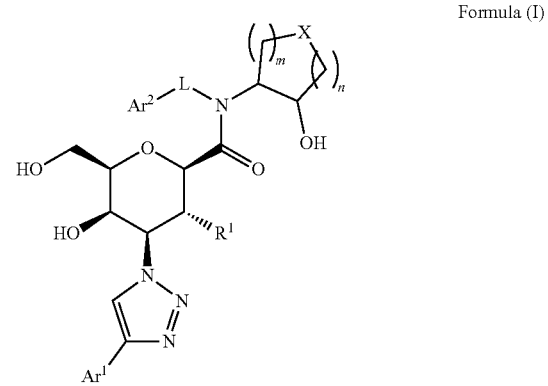

Formula (I)

wherein X, $Ar^1$, $Ar^2$, L, n, m, and $R^1$ are as described in the description, their preparation, to pharmaceutically acceptable salts thereof, and to their use as pharmaceuticals, to pharmaceutical compositions containing one or more compounds of Formula (I), and especially to their use as Galectin-3 inhibitors.

13 Claims, No Drawings

(56) References Cited

FOREIGN PATENT DOCUMENTS

| WO | WO 2021/004940 A1 | 1/2021 |
|---|---|---|
| WO | WO 2021/028323 A1 | 2/2021 |
| WO | WO 2021/028336 A1 | 2/2021 |
| WO | WO 2021/028570 A1 | 2/2021 |
| WO | WO 2021/038068 A1 | 3/2021 |
| WO | WO 2022/073969 A1 | 4/2022 |
| WO | WO 2022/090544 A1 | 5/2022 |
| WO | WO 2022/184755 A1 | 9/2022 |

OTHER PUBLICATIONS

U.S. Appl. No. 17/633,941, filed Feb. 8, 2022 (371(c) Date), Bolli et al.
U.S. Appl. No. 17/634,512, filed Feb. 10, 2022 (371(c) Date), Bolli et al.
U.S. Appl. No. 17/638,799, filed Feb. 25, 2022 (371(c) Date), Bolli et al.
U.S. Appl. No. 18/248,007, filed Apr. 5, 2023 (371(c) Date), Bolli et al.
U.S. Appl. No. 18/251,273, filed May 1, 2023 (371(c) Date), Bolli et al.
U.S. Appl. No. 18/548,833, filed Sep. 1, 2023 (371(c) Date), Bolli et al.
Arciniegas, E. et al., "Galectin-1 and Galectin-3 and Their Potential Binding Partners in the Dermal Thickening of Keloid Tissues," The American Journal of Dermatopathology, 2019, 41 (3), 193-204.
Barondes, S. et al., "Galectins: A Family of Animal β-Galactoside-Binding Lectins," Cell, 1994, 76, 597-598.
Burguillos, M. et al., "Macroglia-Secreted Galectin-3 Acts as a Toll-like Receptor 4 Ligand and Contributes to Microglial Activation," Cell Reports, 2015, 10, 1626-1638.
Caniglia, J. et al., "A potential role for Galectin-3 inhibitors in the treatment of COVID-19," PeerJ, 2020, 8:e9392, 10 pages, doi:10.7717/peerj.9392.
Chen, W-S. et al., "Galectin-3 Inhibition by a Small-Molecule Inhibitor Reduces Both Pathological Corneal Neovascularization and Fibrosis," Investigative Ophthalmology & Visual Science, 2017, 58 (1), 9-20.
Chen, Y-J. et al., "Galectin-3 Enhances Avian H5N1 Influenza A Virus-Induced Pulmonary Inflammation by Promoting NLRP3 Inflammasome Activation," The American Journal of Pathology, 2018, 188 (4), 1031-1042.
Chiariotti, L. et al., "Galectin genes: Regulation of expression," Glycoconjugate Journal, 2004, 19, 441-449.
Dang, Z. et al., "Tubular Atrophy and Interstitial Fibrosis After Renal Transplantation is Dependent on Galectin-3," Transplantation, 2012, 93 (5), 477-484.
Deroo, E. et al., "The role of galectin-3 and galectin-3-binding protein in venous thrombosis," Blood, 2015, 125 (11), 1813-1821.
Falcone, C. et al., "Galectin-3 Plasma Levels and Coronary Artery Disease: A New Possible Biomarker of Acute Coronary Syndrome," International Journal of Immunopathology and Pharmacology, 2011, 24 (4), 905-913.
Farhad, M. et al., "The role of Galectin-3 in modulating tumor growth and immunosuppression within the tumor microenvironment," OncoImmunology, 2018, 7(6), e1434467, 8 pages, https://doi.org/10.1080/2162402X.2018.1434467.
Galectin Therapeutics, "Combination Immunotherapy with Galectin-3 Inhibitor GR-MD-02 Enhances Effects in Pre-clinical Models and Early Results of Phase 1 Clinical Trials," Press Release, dated 2017, 3 pages.
Galectin Therapeutics, "Galectin Therapeutics Announces Results from Phase 2b NASH-CX Trial," Bloomberg, Press Release, dated 2017, 5 pages.
Galecto Biotech, "Galecto Biotech's Lead Molecule TD139 is Safe, Well Tolerated, with Direct Target Engagement and Biomarker Effects in a Clinical Phase Ib/IIa trial in IPF Patients," Press Release, dated 2017, 4 pages.
Gao, P. et al., "Galectin-3: its role in asthma and potential as an anti-inflammatory target," Respiratory Research, 2013, 14:136, 9 pages, doi:10.1186/1465-9921-14-136.
Gehlken, C. et al., "Galectin-3 in Heart Failure: An Update of the Last 3 Years," Heart Failure Clinics, 2018, 14, 75-92.
Greene, T. et al., Eds., Protective Groups in Organic Synthesis, Wiley-Interscience, 1999.
Guha, P. et al., "Cod glycopeptide with picomolar affinity to galectin-3 suppresses T-cell apoptosis and prostate cancer metastasis," Proceedings of the National Academy of Sciences, 2013, 110 (13), 5052-5057.
Henderson, N. et al., "Galectin-3 regulates myofibroblast activation and hepatic fibrosis," Proceedings of the National Academy of Sciences, 2006, 103 (13), 5060-5065.
Henderson, N. et al., "Galectin-3 Expression and Secretion Links Macrophages to the Promotion of Renal Fibrosis," The American Journal of Pathology, 2008, 172 (2), 288-298.
Henderson, N. et al., "The regulation of inflammation by galectin-3," Immunological Reviews, 2009, 230, 160-171.
Hsu, D. et al., "Galectin-3 Expression is Induced in Cirrhotic Liver and Hepatocellular Carcinoma," International Journal of Cancer, 1999, 81, 519-526.
Jin, Q-h. et al., "Serum galectin-3: a risk factor for vascular complications in type 2 diabetes mellitus," Chinese Medical Journal, 2013, 126 (11), 2109-2115.
Johannes, L. et al., "Galectins at a glance," Journal of Cell Science, 2018, 131, jcs208884, 9 pages, doi:10.1242/jcs.208884.
Kikuchi, Y. et al., "Galectin-3-positive call infiltration in human diabetic nephropathy," Nephrology Dialysis Transplantation, 2004, 19 (3), 602-607.
Lacina, L. et al., "Glycophenotype of Psoriatic Skin," Folia Biologica (Praha), 2006, 52, 10-15.
Ladouceur, S. et al., "One-Pot Click Synthesis of 1N-Alkyl-4-aryl-1,2,3-triazoles from Protected Arylalkynes and Alkyl Bromides," Synthesis, 2011, 22, 3604-3611.
Leffler, H. et al., "Introduction to galectins," Glycoconjugate Journal, 2004, 19, 433-440.
Li, P. et al., "Hematopoietic-derived Galectin-3 Causes Cellular and Systemic Insulin Resistance," HHS Public Access, Author manuscript, available in PMC 2017, 22 pages, face of article states: Published in final edited form as: Cell, 2016, 167(4), 973-984, doi:10.1016/j.cell.2016.10.025.
Liu, F-T. et al., "Galectins in acute and chronic inflammation," Annals of the New York Academy of Sciences, 2012, 1253, 80-91.
Lowary, T. et al., "Recognition of synthetic O-methyl, epimeric, and amino analogues of the acceptor α-L-Fuc $p$-(1 → 2)-β-D-Gal $p$-OR by the blood-group A and B gene-specified glycosyltransferases," Carbohydrate Research, 1994, 251, 33-67.
Mackinnon, A. et al., "Regulation of Transforming Growth Factor-βI-driven Lung Fibrosis by Galectin-3," American Journal of Respiratory and Critical Care Medicine, 2012, 185 (5), 537-546.
Nachtigal, M. et al., "Galectin-3 Expression in Human Atherosclerotic Lesions," American Journal of Pathology, 1998, 152 (5), 1199-1208.
Nishi, Y. et al., "Role of Galectin-3 in Human Pulmonary Fibrosis," Allergology International, 2007, 56 (1), 57-65.
Noël, J-C. et al., "Galectin-3 is Overexpressed in Various Forms of Endometriosis," Applied Immunohistochemistry & Molecular Morphology, 2011, 19 (3), 253-257.
Rao, S. et al., "Regulation of Eosinophil Recruitment and Activation by Galectins in Allergic Asthma," Frontiers in Medicine, 2017, 4:68, 12 pages, doi:10.3389/fmed.2017.00068.
Rebholz, C. et al., "Plasma galectin-3 levels are associated with the risk of incident chronic kidney disease," Kidney International, 2018, 93, 252-259.
Remington, The Science and Practice of Pharmacy, 21st Edition, 2005, Part 5, "Pharmaceutical Manufacturing," published by Lippincott Williams & Wilkins.
Ruvolo, P., "Galectin 3 as a guardian of the tumor microenvironment," Biochimica et Biophysica Acta, 2016, 1863, 427-437.

(56) References Cited

OTHER PUBLICATIONS

Saegusa J. et al., "Galectin-3 is Critical for the Development of the Allergic Inflammatory Response in a Mouse Model of Atopic Dermatitis," The American Journal of Pathology, 2009, 174 (3), 922-931.
Sano, H. et al, "Human Galectin-3 is a Novel Chemoattractant for Monocytes and Macrophages," The Journal of Immunology, 2000, 165 (4), 2156-2164.
Sciacchitano, S. et al., "Galectin-3: One Molecule for an Alphabet of Diseases, from A to Z," International Journal of Molecular Sciences, 2018, 19, 379, 59 pages, doi:10.3390/ijms19020379.
Sharma, U. et al., "Novel anti-inflammatory mechanisms of N-Acetyl-Ser-Asp-Lys-Pro in hypertension-induced target organ damage," HHS Public Access, Author manuscript, available in PMC 2019, 17 pages, face of article states: Published in final edited form as: *Am J Physiol Heart Circ Physiol.*, 2008, 294(3): H1226-H1232, doi:10.1152/ajpheart.00305.2007.
Stahl, P. et al., Eds., Handbook of Pharmaceutical Salts, Properties, Selection, and Use, Wiley-VCH, 2008.
Suhara, Y. et al., "Oligomers of Glycamino Acid," Bioorganic & Medicinal Chemistry, 2002, 10, 1999-2013.
Sundblad, V. et al., "Regulated expression of galectin-3, a multifunctional glycan-binding protein, in haematopoietic and non-haematopoietic tissues," Histology and Histopathology, 2011, 26, 247-265.
Taniguchi, T. et al., "Serum Levels of Galectin-3: Possible Association with Fibrosis, Aberrant Angiogenesis, and Immune Activation in Patients with Systemic Sclerosis," Journal of Rheumatology, 2012, 39 (3), 539-544.
Thandavarayan, R. et al., "14-3-3 protein regulates Ask1 signaling and protects against diabetic cardiomyopathy," Biochemical Pharmacology, 2008, 75, 1797-1806.
Vuong, L. et al., "An Orally Active Galectin-3 Antagonist Inhibits Lung Adenocarcinoma Growth and Augments Response to PD-L1 Blockade," Cancer Research, 2019, 79 (7), 1480-1492.
Wouters, J. et al., Eds., Pharmaceutical Salts and Co-crystals, RSC Publishing, 2012.
Zbigniew, J. et al., Eds., Click Chemistry in Glycoscience, New Developments and Strategies, John Wiley & Sons, Inc., Hoboken, New Jersey, 2013.
Zhong, X. et al., "The role of galectin-3 in heart failure and cardiovascular disease," Clinical and Experimental Pharmacology and Physiology, 2019, 46, 197-203.

* cited by examiner

HYDROXYHETEROCYCLOALKANE-CARBAMOYL DERIVATIVES

CROSS REFERENCE TO RELATED APPLICATIONS

This application is a National Stage Entry under 35 U.S.C. § 371 of International Application No. PCT/EP2022/052948 filed Feb. 8, 2022, which claims priority to International Application No. PCT/EP2021/053084 filed Feb. 9, 2021, the contents of each of which are hereby incorporated by reference in their entireties.

The present invention relates to compounds of Formula (I) which are galectin-3 inhibitors and their use in the prevention/prophylaxis or treatment of diseases and disorders that are related to galectin-3 binding to natural ligands. The invention also concerns related aspects including processes for the preparation of the compounds, pharmaceutical compositions containing one or more compounds of Formula (I), and their medical use as Galectin-3 inhibitors. The compounds of Formula (I)) may especially be used as single agents or in combination with one or more therapeutic agents.

Galectins are defined as a protein family based on conserved 3-galactoside-binding sites found within their characteristic ~130 amino acid (aa) carbohydrate recognition domains (CRDs) (Barondes S H et al., Cell 1994; 76, 597-598). Human, mouse and rat genome sequences reveal the existence of at least 16 conserved galectins and galectin-like proteins in one mammalian genome (Leffler H. et al., Glycoconj. J. 2002, 19, 433-440). So far, three galectin subclasses were identified, the prototypical galectins containing one carbohydrate-recognition domain (CRD); the chimaera galectin consisting of unusual tandem repeats of proline- and glycine-rich short stretches fused onto the CRD; and the tandem-repeat-type galectins, containing two distinct CRDs in tandem connected by a linker (Zhong X., Clin Exp Pharmacol Physiol. 2019; 46:197-203). As galectins can bind either bivalently or multivalently, they can e.g. cross-link cell surface glycoconjugates to trigger cellular signaling events. Through this mechanism, galectins modulate a wide variety of biological processes (Sundblad V. et al., Histol Histopathol 2011; 26: 247-265).

Galectin-3 (Gal-3), the only chimaera type in the galectin family, has a molecular weight of 32-35 kDa and consists of 250 amino acid residues in humans, a highly conserved CRD and an atypical N-terminal domain (ND). Galectin-3 is monomeric up to high concentrations (100 µM), but can aggregate with ligands at much lower concentrations, which is promoted by its N-terminal non-CRD region via an oligomerisation mechanism that is not yet completely understood (Johannes, L. et al., Journal of Cell Science 2018; 131, jcs208884).

Gal-3 is widely distributed in the body, but the expression level varies among different organs. Depending on its extracellular or intracellular localization, it can display a broad diversity of biological functions, including immunomodulation, host-pathogen interactions, angiogenesis, cell migration, wound healing and apoptosis (Sundblad V. et al., Histol Histopathol 2011; 26: 247-265). Gal-3 is highly expressed in many human tumours and cell types, such as myeloid cells, inflammatory cells (macrophages, mast cells, neutrophils, T cells, eosinophils, etc.), fibroblasts and cardiomyocytes (Zhong X. et al., Clin Exp Pharmacol Physiol. 2019; 46:197-203), indicating that Gal-3 is involved in the regulation of inflammatory and fibrotic processes (Henderson N C. Et al., Immunological Reviews 2009; 230: 160-171; Sano H. et al., J Immunol. 2000; 165(4):2156-64). Furthermore, Gal-3 protein expression levels are up-regulated under certain pathological conditions, such as neoplasms and inflammation (Chiariotti L. et al., Glycoconjugate Journal 2004 19, 441-449; Farhad M. et al., OncoImmunology 2018, 7:6, e1434467).

There are multiple lines of evidence supporting functional involvement of Gal-3 in the development of inflammatory/autoimmune diseases, such as asthma (Gao P. et al. Respir Res. 2013, 14:136; Rao S P et al. Front Med (Lausanne) 2017; 4:68), rheumatoid arthritis, multiple sclerosis, diabetes, plaque psoriasis (Lacina L. et al. Folia Biol (Praha) 2006; 52(1-2):10-5) atopic dermatitis (Saegusa J. et al. Am J Pathol. 2009, 174(3):922-31), endometriosis (Noel J C et al. Appl Immunohistochem Mol Morphol. 2011 19(3):253-7), or viral encephalitis (Liu F T et al., Ann N Y Acad Sci. 2012; 1253:80-91; Henderson N C, et al., Immunol Rev. 2009; 230(1):160-71; Li P et al., Cell 2016; 167:973-984). Recently Gal-3 has emerged as a key player of chronic inflammation and organ fibrogenesis development e.g. liver (Henderson N C et al., PNAS 2006; 103: 5060-5065; Hsu D K et al. Int J Cancer. 1999, 81(4):519-26), kidney (Henderson N C et al., Am. J. Pathol. 2008; 172:288-298; Dang Z. et al. Transplantation. 2012, 93(5):477-84), lung (Mackinnon A C et al., Am. J. Respir. Crit. Care Med 2012, 185: 537-546; Nishi Y. et al. Allergol Int. 2007, 56(1):57-65), heart (Thandavarayan R A et al. Biochem Pharmacol. 2008, 75(9):1797-806; Sharma U. et al. Am J Physiol Heart Circ Physiol. 2008; 294(3):H1226-32), as well as the nervous system (Burguillos M A et al. Cell Rep. 2015, 10(9):1626-1638), and in corneal neovascularization (Chen W S. Et al., Investigative Ophthalmology & Visual Science 2017, Vol. 58, 9-20). Additionally, Gal-3 was found to be associated with dermal thickening of keloid tissues (Arciniegas E. et al., The American Journal of dermatopathology 2019; 41(3): 193-204) and systemic sclerosis (SSc) especially with skin fibrosis and proliferative vasculopathy observed in such condition (Taniguchi T. et al. J Rheumatol. 2012, 39(3):539-44). Gal-3 was found to be up-regulated in patient suffering chronic kidney disease (CKD) associated-kidney failure, and especially in those affected by diabetes. Interestingly, data obtained from this patient population showed correlation between Gal-3 upregulation in glomeruli and the observed urinary protein excretion (Kikuchi Y. et al. Nephrol Dial Transplant. 2004, 19(3):602-7). Additionally, a recent prospective study from 2018 demonstrated that higher Gal-3 plasma levels are associated with an elevated risk of developing incident CKD, particularly among hypertension-suffering population (Rebholz C M. et al. Kidney Int. 2018 January; 93(1): 252-259). Gal-3 is highly elevated in cardiovascular diseases (Zhong X. et al. Clin Exp Pharmacol Physiol. 2019, 46(3):197-203), such as atherosclerosis (Nachtigal M. et al. Am J Pathol. 1998; 152(5):1199-208), coronary artery disease (Falcone C. et al. Int J Immunopathol Pharmacol 2011, 24(4):905-13), heart failure and thrombosis (Nachtigal M. et al., Am J Pathol. 1998; 152(5): 1199-208; Gehlken C. et al., Heart Fail Clin. 2018, 14(1): 75-92; DeRoo E P. et al., Blood. 2015, 125(11):1813-21). Gal-3 blood concentration is elevated in obese and diabetic patients and is associated with a higher risk for micro- and macro-vascular complication (such as heart failure, nephropathy/retinopathy, peripheral arterial disease, cerebrovascular event, or myocardial infarction) (Qi-hui-Jin et al. Chin Med J (Engl). 2013,126(11):2109-15). Gal-3 influences oncogenesis, cancer progression, and metastasis (Vuong L. et al., Cancer Res 2019 (79) (7) 1480-1492), and was shown to exert a role as a pro-tumor factor by acting within the micro tumor environment to suppress immune surveillance (Ruvolo P P. et al. Biochim Biophys Acta. 2016 March, 1863(3):427-437; Farhad M. et al. Oncoimmunology 2018 February 20; 7(6): e1434467). Among the cancers that express high level of Gal-3 are found those affecting the thyroid gland, the central nervous system, the tongue, the breast, the gastric system, the head and neck squamous cell, the pancreas, the bladder, the kidney, the liver, the parathyroid, the salivary glands, but also lymphoma, carcinoma, non-small cell lung cancer, melanoma and neuroblastoma (Sciacchitano S. et al. Int J Mol Sci 2018 Jan. 26, 19(2):379).

Also, Gal-3 inhibition has been proposed to be beneficial in the treatment of COVID-19 (Caniglia J L et al. PeerJ 2020, 8:e9392) and influenza H5N1 (Chen Y J et al. Am. J. Pathol. 2018, 188(4), 1031-1042) possibly due to anti-inflammatory effects.

Recently, Gal-3 inhibitors have shown to have positive effects when used in combination immunotherapy (Galectin Therapeutics. Press Release, Feb. 7, 2017) and idiopathic pulmonary fibrosis (Galecto Biotech. Press Release, Mar. 10, 2017) and in NASH cirrhosis (Dec. 5, 2017). WO20180209276, WO2018209255 and WO20190890080 disclose compounds having binding affinity with galectin proteins for the treatment of systemic insulin resistance disorders. Thus, Gal-3 inhibitors, alone or in combination with other therapies, may be useful for the prevention or treatment of diseases or disorders such as fibrosis of organs, cardiovascular diseases and disorders, acute kidney injury and chronic kidney disease, liver diseases and disorders, interstitial lung diseases and disorders, ocular diseases and disorders, cell proliferative diseases and cancers, inflammatory and autoimmune diseases and disorders, gastrointestinal tract diseases and disorders, pancreatic diseases and disorders, abnormal angiogenesis-associated diseases and disorders, brain-associated diseases and disorders, neuropathic pain and peripheral neuropathy, and/or transplant rejection.

Several publications and patent applications describe synthetic inhibitors of Gal-3 that are being explored as antifibrotic agents (see for example WO2005113568, WO2005113569, WO2014067986, WO2016120403, US20140099319, WO2019067702, WO2019075045, WO2014078655, WO2020078807, WO2020078808 and WO2020210308).

The present invention provides novel compounds of Formula (I) which are Galectin-3 inhibitors. The present compounds may, thus, be useful for the prevention/prophylaxis or treatment of diseases and disorders where modulation of Gal-3 binding to its natural carbohydrate ligands is indicated.

1) In a first embodiment, the invention relates to a compound of Formula (I) (wherein it is understood that the absolute configuration is as depicted in the respective formula):

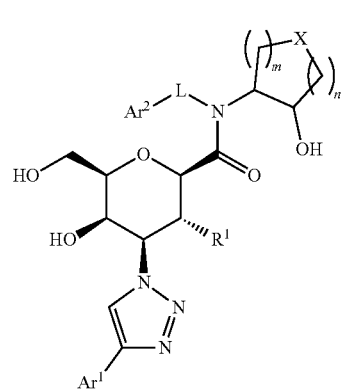

Formula (I)

wherein n and m each, independently, represent the integer 1 or 2 such that n+m equals 2 or 3;

X represents O or $NR^2$; wherein $R^2$ represents hydrogen, $C_{1-3}$-alkyl (especially methyl or ethyl), —CO—H, —$SO_2$—$C_{1-3}$-alkyl (especially $SO_2$—$CH_3$), or —CO—$C_{1-3}$-alkyl (especially —CO—$CH_3$);

$Ar^1$ represents

Aryl (especially phenyl), which is mono-, di-, tri-, tetra-, or penta-substituted (especially di-, or tri-substituted), wherein the substituents are independently selected from halogen; methyl; cyano; methoxy; trifluoromethyl; trifluoromethoxy; and $NR^{N11}R^{N12}$ wherein $R^{N11}$ represents hydrogen and $R^{N12}$ represents hydroxy-$C_{2-3}$-alkyl, or $R^{N11}$ and $R^{N12}$ together with the nitrogen atom to which they are attached form a 4- to 6-membered heterocyclyl selected from morpholin-4-yl, azetidine-1-yl, pyrrolidine-1-yl, and piperidine-1-yl, wherein said 4- to 6-membered heterocyclyl is unsubstituted or mono-substituted with hydroxy (especially the substituents are independently selected from halogen, or methyl);

5- or 6-membered heteroaryl, wherein said 5- or 6-membered heteroaryl independently is unsubstituted, mono- or di-substituted, wherein the substituents are independently selected from halogen, methyl, cyano, and methoxy; or 9- or 10-membered heteroaryl, wherein said 9- or 10-membered heteroaryl independently is unsubstituted, or mono-substituted with methyl;

$R^1$ represents hydroxy;

$C_{1-3}$-alkoxy;

—O—CO—$C_{1-3}$-alkyl;

—O—$CH_2$—$CH_2$—OH; or

—O—$CH_2$—CO—$R^{1X}$ wherein $R^{1X}$ represents

-hydroxy;

morpholin-4-yl; or

—$NR^{N21}R^{N22}$, wherein $R^{N21}$ and $R^{N22}$ together with the nitrogen atom to which they are attached form a 4- to 6-membered heterocyclyl selected from azetidine-1-yl, pyrrolidine-1-yl, and piperidine-1-yl, wherein said 4- to 6-membered heterocyclyl is mono-substituted with hydroxy;

[such substituent $R^1$ especially represents $C_{1-3}$-alkoxy (notably methoxy)]

L represents a direct bond, methylene, or ethylene (especially a direct bond); and Ar² represents phenyl or 5- or 6-membered heteroaryl (especially phenyl), wherein said phenyl or 5- or 6-membered heteroaryl independently is unsubstituted, or mono-, di- or tri-substituted (especially mono-, or di-substituted); wherein the substituents are independently selected from $C_{1-6}$-alkyl (especially methyl), $C_{3-6}$-cycloalkyl, —$CH_2$—$C_{3-6}$-cycloalkyl, $C_{1-3}$-fluoroalkyl, $C_{1-3}$-fluoroalkoxy, $C_{1-3}$-alkoxy (especially methoxy), halogen, morpholine-4-yl, amino, ethynyl, and cyano (especially are independently selected from $C_{1-6}$-alkyl (notably methyl), $C_{1-3}$-alkoxy (notably methoxy), halogen, and cyano);

9-membered bicyclic heteroaryl or 10-membered bicyclic heteroaryl, wherein said 9- or 10-membered bicyclic heteroaryl independently is unsubstituted, mono- or di-substituted, wherein the substituents are independently selected from methyl, methoxy, and halogen; or naphthyl;

or a pharmaceutically acceptable salt thereof.

In a sub-embodiment, said compounds of Formula (I), or, mutatis mutandis, compounds of Formula (II), (III) or (IV) below, are such that the nitrogen linking the heterocycloalkane to the rest of the molecule and the hydroxy substituent of said heterocycloalkane, as depicted in the respective formula, are in relative trans configuration. For avoidance of doubt, compounds of Formula (I) are especially compounds of Formula ($I_S$) as depicted in embodiment 3) below, compounds of Formula ($I_R$) as depicted in embodiment 4) below, or any mixture thereof.

2) A second aspect of the invention relates to compounds of Formula (I) according to embodiment 1), wherein said compounds are also compounds of Formula (II), Formula (III) or Formula (IV) (wherein it is understood that the absolute configuration is as depicted in the respective formula):

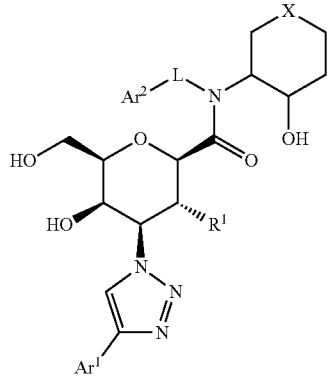

Formula (III)

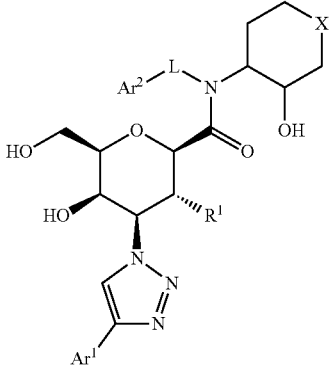

Formula (IV)

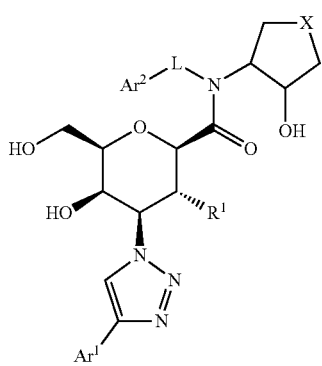

Formula (II)

wherein in each of Formula (II), Formula (III) or Formula (IV), the groups X, Ar¹, Ar², R¹, and L are independently as defined in embodiment 1).

In a first sub-embodiment, the compounds of embodiment 2) refer to the compounds of Formula (II), (III), or (IV) wherein X is O; and wherein the groups Ar¹, Ar², R¹, and L are independently as defined in embodiment 1).

In a second sub-embodiment, the compounds of embodiment 2) refer to the compounds of Formula (II), (III), or (IV) wherein X is NR²; wherein R² represents hydrogen, $C_{1-3}$-alkyl (especially methyl or ethyl), —CO—H, —$SO_2$—$C_{1-3}$-alkyl (especially $SO_2$—$CH_3$), —CO—$C_{1-3}$-alkyl (especially —CO—$CH_3$); and wherein the groups Ar¹, Ar², R¹, and L are independently as defined in embodiment 1).

3) A third aspect of the invention relates to compounds of Formula (I) according to embodiment 1), wherein said compounds are also compounds of Formula ($I_S$) (wherein it is understood that the absolute configuration is as depicted in the respective formula):

Formula (I$_S$)

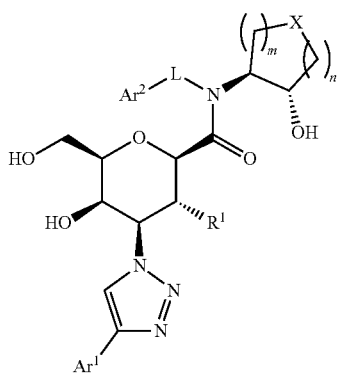

wherein the groups X, Ar$^1$, Ar$^2$, R$^1$, L, m, and n are as defined in embodiment 1). In a particular embodiment, said compounds of Formula (I$_S$) are also compounds of Formula (II$_S$), Formula (III$_S$) or Formula (IV$_S$) (wherein it is understood that the absolute configuration is as depicted in the respective formula):

Formula (II$_s$)

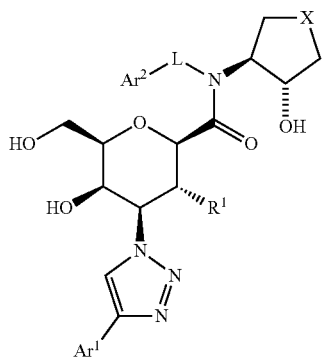

Formula (III$_s$)

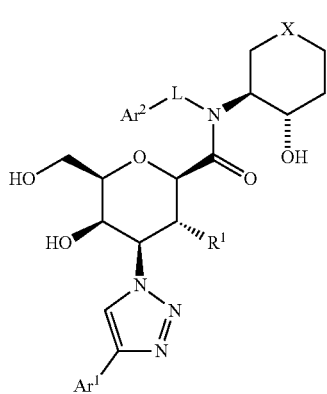

Formula (IV$_s$)

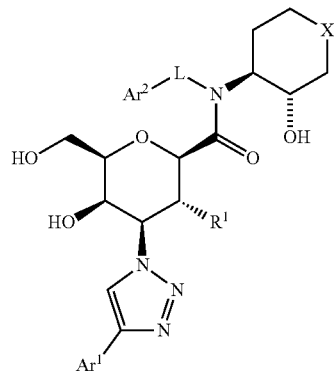

wherein in each of Formula (II$_S$), Formula (III$_S$) or Formula (IV$_S$), the groups X, Ar$^1$, Ar$^2$, R$^1$, and L are independently as defined in embodiment 1).

In a first sub-embodiment, the compounds of embodiment 3) refer to the compounds of Formula (II$_S$), (III$_S$), or (IV$_S$) wherein X is O; and wherein the groups Ar$^1$, Ar$^2$, R$^1$, and L are independently as defined in embodiment 1).

In a second sub-embodiment, the compounds of embodiment 3) refer to the compounds of Formula (II$_S$), (III$_S$), or (IV$_S$) wherein X is NR$^2$; wherein R$^2$ represents hydrogen, C$_{1-3}$-alkyl (especially methyl or ethyl), —CO—H, —SO$_2$—C$_{1-3}$-alkyl (especially SO$_2$—CH$_3$), —CO—C$_{1-3}$-alkyl (especially —CO—CH$_3$); and wherein the groups Ar$^1$, Ar$^2$, R$^1$, and L are independently as defined in embodiment 1).

4) Another aspect of the invention relates to compounds of Formula (I) according to embodiment 1), wherein said compounds are also compounds of Formula (I$_R$) (wherein it is understood that the absolute configuration is as depicted in the respective formula):

Formula (I$_R$)

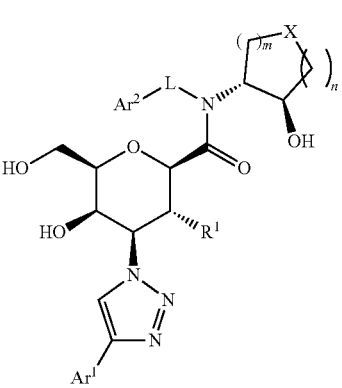

wherein the groups X, Ar$^1$, Ar$^2$, R$^1$, L, m and n are independently as defined in embodiment 1). In a particular embodiment, said compounds of Formula (I$_R$) are also compounds of Formula (II$_R$), Formula (III$_R$) or Formula (IV$_R$) (wherein it is understood that the absolute configuration is as depicted in the respective formula):

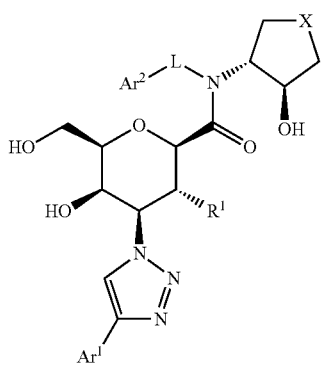

Formula (II_R)

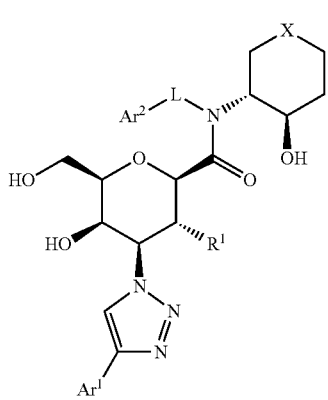

Formula (III_R)

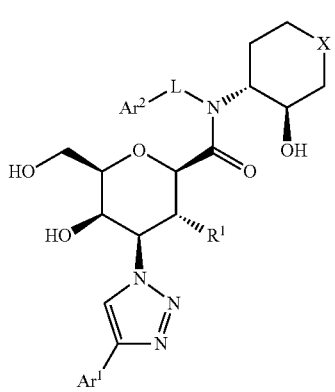

Formula (IV_R)

wherein in each of Formula (II_R), Formula (III_R) or Formula (IV_R), the groups X, Ar¹, Ar², R¹, and L are independently as defined in embodiment 1).

In a first sub-embodiment, the compounds of embodiment 4) refer to the compounds of Formula (II_R), (III_R), or (IV_R) wherein X is O; and wherein the groups Ar¹, Ar², R¹, and L are independently as defined in embodiment 1).

In a second sub-embodiment, the compounds of embodiment 4) refer to the compounds of Formula (II_R), (III_R), or (IV_R) wherein X is NR²; wherein R² represents hydrogen, $C_{1-3}$-alkyl (especially methyl or ethyl), —CO—H, —SO$_2$—$C_{1-3}$-alkyl (especially SO$_2$—CH$_3$), —CO—$C_{1-3}$-alkyl (especially —CO—CH$_3$); and wherein the groups Ar¹, Ar², R¹, and L are independently as defined in embodiment 1).

The compounds of Formula (I) contain five stereogenic or asymmetric centers situated on the tetrahydropyran moiety and which are in the absolute configuration as drawn for Formula (I). The compounds of Formula (I) further contain two stereogenic or asymmetric centers situated on the heterocycloalkane moiety. In a particular embodiment, said compounds of Formula (I), or, mutatis mutandis, compounds of Formula (II), (III) or (IV), are such that the nitrogen linking the heterocycloalkane to the rest of the molecule and the hydroxy substituent of said heterocycloalkane, as depicted in the respective formula, are in relative trans configuration. For avoidance of doubt, compounds of Formula (I) are especially compounds of Formula (I_S) as depicted in embodiment 3), compounds of Formula (I_R) as depicted in embodiment 4), or any mixture thereof.

In addition, the compounds of Formula (I) may contain one, and possibly more stereogenic or asymmetric centers, such as one or more additional asymmetric carbon atoms. The compounds of Formula (I) may thus be present as mixtures of stereoisomers or preferably as pure stereoisomers. Mixtures of stereoisomers may be separated in a manner known to a person skilled in the art.

In case a particular compound (or generic structure) is designated as being in a certain absolute configuration, e.g. as (R)- or (S)-enantiomer, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center. In analogy, two stereogenic centers e.g in a cyclic group may be present in a certain relative configuration.

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

The present invention also includes isotopically labelled, especially ²H (deuterium) labelled compounds of Formula (I) according to embodiments 1) to 18), which compounds are identical to the compounds of Formula (I) except that one or more atoms have each been replaced by an atom having the same atomic number but an atomic mass different from the atomic mass usually found in nature. Isotopically labelled, especially ²H (deuterium) labelled compounds of formulae (I), (II), (III), (IV), (I_S), (II_S), (III_S), (IV_S), (I_R), (II_R), (III_R), (IV_R) and (V), and salts thereof, are within the scope of the present invention. Substitution of hydrogen with the heavier isotope ²H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms. In a sub-embodiment, the compounds of Formula (I) are not isotopically labelled at all. Isotopically labelled compounds of Formula (I) may be prepared in analogy to the methods described hereinafter, but using the appropriate isotopic variation of suitable reagents or starting materials.

In this patent application, a bond drawn as a dotted line shows the point of attachment of the radical drawn. For example, the radical drawn below

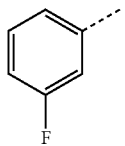

is a 3-fluorophenyl group.

Where the plural form is used for compounds, salts, pharmaceutical compositions, diseases and the like, this is intended to mean also a single compound, salt, or the like.

Any reference to compounds of Formula (I) according to embodiments 1) to 18) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of formulae (I), (II), (III), (IV), $(I_S)$, $(II_S)$, $(III_S)$, $(IV_S)$, $(I_R)$, $(II_R)$, $(III_R)$, $(IV_R)$ and (V) as defined in any one of embodiments 1) to 17), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

In this patent application, the compounds are named using IUPAC nomenclature, but can also be named using carbohydrate nomenclature. Thus, the moiety:

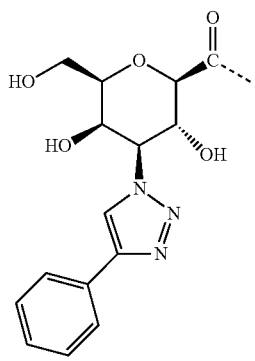

can be named (2R,3R,4S,5R,6R)-3,5-dihydroxy-6-(hydroxymethyl)-4-(4-phenyl-1H-1,2,3-triazol-1-yl)tetrahydro-2H-pyran-2-carbonyl or, alternatively, 1,3-di-deoxy-3-[4-phenyl-1H-1,2,3-triazol-1-yl]-β-D-galactopyranoside-1-carbonyl, wherein the absolute configuration of carbon atom carrying the carbonyl group which is the point of attachment to the rest of the molecule is in (2R)—, respectively, beta-configuration. For example, compound (2R,3R,4S,5R,6R)—N-(3-chlorophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide is to be understood as also referring to: 1,3-di-deoxy-2-O-methyl-3-[4-(3,4,5-trifluorophenyl)-1H-1,2,3-triazol-1-yl]-N-(3-chlorophenyl)-N-((3S,4R)-4-hydroxy-3-tetrahydrofuranyl)-beta-D-galacto-pyranose-1-carboxamide.

Whenever a substituent is denoted as optional, it is understood that such substituent may be absent (i.e. the respective residue is unsubstituted with regard to such optional substituent), in which case all positions having a free valency (to which such optional substituent could have been attached to; such as for example in an aromatic ring the ring carbon atoms and/or the ring nitrogen atoms having a free valency) are substituted with hydrogen where appropriate. Likewise, in case the term "optionally" is used in the context of (ring) heteroatom(s), the term means that either the respective optional heteroatom(s), or the like, are absent (i.e. a certain moiety does not contain heteroatom(s)/is a carbocycle/or the like), or the respective optional heteroatom(s), or the like, are present as explicitly defined. If not explicitly defined otherwise in the respective embodiment or claim, groups defined herein are unsubstituted.

The term "halogen" means fluorine, chlorine, bromine, or iodine (especially fluorine, chlorine or bromine).

The term "alkyl", used alone or in combination, refers to a saturated straight or branched chain hydrocarbon group containing one to six carbon atoms. The term "$C_{x-y}$-alkyl" (x and y each being an integer), refers to an alkyl group as defined before, containing x to y carbon atoms. For example, a $C_{1-6}$-alkyl group contains from one to six carbon atoms. Representative examples of alkyl groups are methyl, ethyl, propyl, isopropyl, butyl, isobutyl, tert.-butyl, pentyl, 3-methyl-butyl, 2,2-dimethyl-propyl and 3,3-dimethyl-butyl. Preferred is methyl. For avoidance of any doubt, in case a group is referred to as e.g. propyl or butyl, it is meant to be n-propyl, respectively n-butyl. In case the substituent of $Ar^1$ or $Ar^2$ represents "$C_{1-6}$-alkyl", the term especially refers to methyl. In case $R^2$ represents "$C_{1-6}$-alkyl", the term especially refers to methyl or ethyl. In case the term "$C_{1-3}$-alkyl" is used relative to a substituent of $R^2$, such as in "—$SO_2$—$C_{1-3}$-alkyl" or "—CO—$C_{1-3}$-alkyl", the term especially refers to methyl.

The term "fluoroalkyl", used alone or in combination, refers to an alkyl group as defined before containing one to three carbon atoms in which one or more (and possibly all) hydrogen atoms have been replaced with fluorine. The term "$C_{x-y}$-fluoroalkyl" (x and y each being an integer) refers to a fluoroalkyl group as defined before containing x to y carbon atoms. For example, a $C_{1-3}$-fluoroalkyl group contains from one to three carbon atoms in which one to seven hydrogen atoms have been replaced with fluorine.

The term "fluoroalkoxy", used alone or in combination, refers to an alkoxy group as defined before containing one to three carbon atoms in which one or more (and possibly all) hydrogen atoms have been replaced with fluorine. The term "$C_{x-y}$-fluoroalkoxy" (x and y each being an integer) refers to a fluoroalkoxy group as defined before containing x to y carbon atoms. For example, a $C_{1-3}$-fluoroalkoxy group contains from one to three carbon atoms in which one to seven hydrogen atoms have been replaced with fluorine.

The term "cycloalkyl", used alone or in combination, refers especially to a saturated monocyclic, or to a fused-, bridged-, or spiro-bicyclic hydrocarbon ring containing three to eight carbon atoms. The term "$C_{x-y}$-cycloalkyl" (x and y each being an integer), refers to a cycloalkyl group as defined before containing x to y carbon atoms. For example, a $C_{3-6}$-cycloalkyl group contains from three to six carbon atoms. Examples of cycloalkyl groups are cyclopropyl, cyclobutyl, cyclopentyl, and cyclohexyl.

The term "alkoxy", used alone or in combination, refers to an alkyl-O— group wherein the alkyl group is as defined before. The term "$C_{x-y}$-alkoxy" (x and y each being an integer) refers to an alkoxy group as defined before containing x to y carbon atoms. Preferred are ethoxy and especially methoxy. In case $R^1$ represents "$C_{1-3}$-alkoxy" the term especially refers to methoxy. In case the substituent of $Ar^2$ represents "$C_{1-3}$-alkoxy", the term especially refers to methoxy.

The term "aryl", used alone or in combination, means phenyl or naphthyl, especially phenyl, wherein said aryl group is unsubstituted or substituted as explicitly defined. For the substituent $Ar^1$ or $Ar^2$ representing "aryl", the term especially means phenyl.

The term "heteroaryl", used alone or in combination, and if not explicitly defined in a broader or more narrow way, means a 5- to 10-membered monocyclic or bicyclic aromatic ring containing one to a maximum of four heteroatoms, each independently selected from oxygen, nitrogen and sulfur. Representative examples of such heteroaryl groups are 5-membered heteroaryl groups such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl, tetrazolyl; 6-membered heteroaryl groups such as pyridinyl, pyrimidinyl, pyridazinyl, pyrazinyl; and 8- to 10-membered bicyclic heteroaryl groups such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, thienopyridinyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined.

For the substituent $Ar^1$ representing "5- or 6-membered heteroaryl", the term especially means thiazolyl (especially 4-chlorothiazol-2-yl). For the substituent $Ar^2$ representing "5- or 6-membered heteroaryl", the term especially means furanyl, thiophenyl, pyrrolyl, thiazolyl, isothiazolyl, isoxazolyl, pyrazolyl, imidazolyl, pyridinyl, or pyrimidinyl; wherein said 5- or 6-membered heteroaryl is unsubstituted or substituted as explicitly defined.

For the substituent $Ar^1$ representing "9- or 10-membered bicyclic heteroaryl", the term especially means benzothiazolyl (especially 2-methylbenzo[d]thiazol-6-yl). For the substituent $Ar^2$ representing "9-membered bicyclic heteroaryl", the term especially means indolyl, benzothiophenyl, benzothiazolyl, or benzoimidazolyl; wherein said 9-membered bicyclic heteroaryl is unsubstituted or substituted as explicitly defined. For the substituent $Ar^2$ representing "10-membered bicyclic heteroaryl", the term especially means quinolinyl or quinoxalinyl; wherein said 10-membered bicyclic heteroaryl is unsubstituted or substituted as explicitly defined.

The term "cyano" refers to a group —CN.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

Further embodiments of the invention are presented hereinafter:

5) Another embodiment relates to compounds according to any of embodiments 1) to 4), wherein $Ar^1$ represents a phenyl which is mono-, di-, tri-, tetra-, or penta-substituted (especially di-, or tri-substituted), wherein the substituents are independently selected from halogen; methyl; cyano; and methoxy.

6) Another embodiment relates to compounds according to any of embodiments 1) to 4), wherein $Ar^1$ represents a phenyl which is di- or tri-substituted, wherein the substituents are independently selected from halogen and methyl.

In a sub-embodiment, at least one of said substituents is attached in meta- or in para-position of said phenyl.

7) Another embodiment relates to compounds according to any of embodiments 1) to 4), wherein $Ar^1$ represents a phenyl which is di- or tri-substituted, wherein the substituents are independently selected from halogen, methyl, and cyano;

wherein at least one of said substituents is attached in a meta- or in the para-position of said phenyl;

wherein notably, if present, said substituent in the para-position is halogen or methyl; and wherein notably, if present, said substituent in meta-position is halogen.

8) Another embodiment relates to compounds according to any of embodiments 1) to 4), wherein $Ar^1$ represents phenyl which is di- or tri-substituted, wherein the substituents are independently selected from halogen; methyl; and cyano (especially halogen or methyl); wherein in case said phenyl is di-substituted, at least one of said substituents is in a meta-position, wherein said substituent is especially halogen; and the other substituent is especially in the other meta- or in para-position; or in case said phenyl is tri-substituted, the substituents form a 2,3,4 or a 3,4,5 substitution pattern, relative to the point of attachment of $Ar^1$, wherein notably the substituent in para-position is halogen or methyl, and the remaining substituents are independently halogen (especially fluoro).

9) Another embodiment relates to compounds according to any of embodiments 1) to 4), wherein $Ar^1$ represents

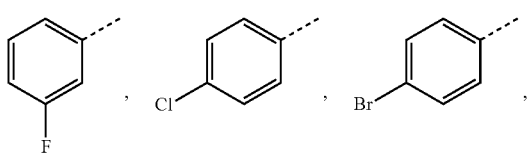
In a sub-embodiment, Ar¹ especially represents a group selected from the groups A) or B):
A)
wherein each of said groups A) and B) forms a particular sub-embodiment.
In another sub-embodiment, Ar¹ especially represents a group selected from the groups C), D) or E):
C)
D)

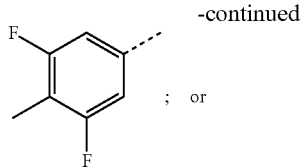

E)

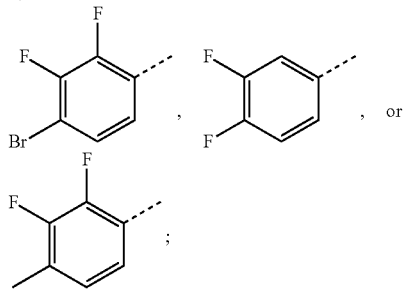

wherein each of said groups C), D) and E) forms a particular sub-embodiment.

10) Another embodiment relates to compounds according to any one of embodiments 1) to 9), wherein $R^1$ represents methoxy.

11) Another embodiment relates to compounds according to any one of embodiments 1) to 10), wherein L represents a direct bond.

12) Another embodiment relates to compounds according to any one of embodiments 1) to 11), wherein $Ar^2$ represents phenyl which is unsubstituted, mono-, di- or tri-substituted (especially mono-, or di-substituted), wherein the substituents are independently selected from $C_{1-6}$-alkyl (especially methyl), $C_{1-3}$-alkoxy (especially methoxy), halogen, and cyano, (wherein especially at least one of said substituents is in a meta-position).

13) Another embodiment relates to compounds according to any one of embodiments 1) to 11), wherein $Ar^2$ represents phenyl which is mono-, or di-substituted, wherein the substituents are independently selected from $C_{1-4}$-alkyl (especially methyl), $C_{1-3}$-alkoxy (especially methoxy), halogen, and cyano, (wherein especially at least one of said substituents is in a meta-position).

14) Another embodiment relates to compounds according to any one of embodiments 1) to 11), wherein $Ar^2$ represents phenyl which is
mono-substituted, wherein the substituent is selected from $C_{1-4}$-alkyl (especially methyl), $C_{1-3}$-alkoxy (especially methoxy), halogen, and cyano (wherein especially said substituent is in meta-position); or
di-substituted, wherein the substituents are independently selected from $C_{1-4}$-alkyl (especially methyl), $C_{1-3}$-alkoxy (especially methoxy), halogen, and cyano (wherein especially said substituents are in meta-position).

15) Another embodiment relates to compounds according to any one of embodiments 1) to 10), wherein the fragment -L-$Ar^2$ represents:

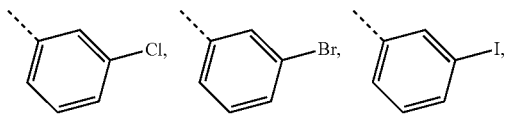

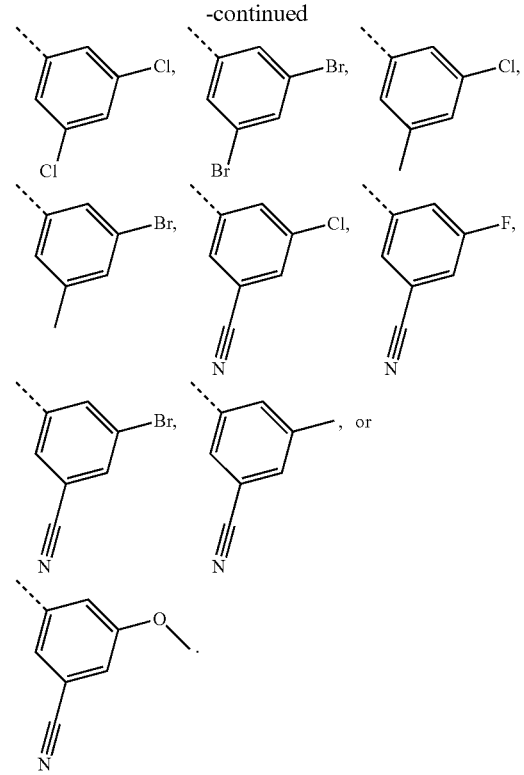

16) The invention, thus, relates to compounds of Formula (I) as defined in embodiment 1), or to such compounds further limited by the characteristics of any one of embodiments 2) to 15), under consideration of their respective dependencies; to pharmaceutically acceptable salts thereof; and to the use of such compounds as further described herein below. For avoidance of any doubt, especially the following embodiments relating to the compounds of Formula (I) are thus possible and intended and herewith specifically disclosed in individualized form:

2+1, 3+1, 4+1, 5+1, 5+2+1, 5+3+1, 5+4+1, 6+1, 6+2+1, 6+3+1, 6+4+1, 7+1, 7+2+1, 7+3+1, 7+4+1, 8+1, 8+2+1, 8+3+1, 8+4+1, 9+1, 9+2+1, 9+3+1, 9+4+1, 10+1, 10+2+1, 10+3+1, 10+4+1, 10+5+1, 10+5+2+1, 10+5+3+1, 10+5+4+1, 10+6+1, 10+6+2+1, 10+6+3+1, 10+6+4+1, 10+7+1, 10+7+2+1, 10+7+3+1, 10+7+4+1, 10+8+1, 10+8+2+1, 10+8+3+1, 10+8+4+1, 10+9+1, 10+9+2+1, 10+9+3+1, 10+9+4+1, 11+1, 11+2+1, 11+3+1, 11+4+1, 11+5+1, 11+5+2+1, 11+5+3+1, 11+5+4+1, 11+6+1, 11+6+2+1, 11+6+3+1, 11+6+4+1, 11+7+1, 11+7+2+1, 11+7+3+1, 11+7+4+1, 11+8+1, 11+8+2+1, 11+8+3+1, 11+8+4+1, 11+9+1, 11+9+2+1, 11+9+3+1, 11+9+4+1, 11+10+1, 11+10+2+1, 11+10+3+1, 11+10+4+1, 11+10+5+1, 11+10+5+2+1, 11+10+5+3+1, 11+10+5+4+1, 11+10+6+1, 11+10+6+2+1, 11+10+6+3+1, 11+10+6+4+1, 11+10+7+1, 11+10+7+2+1, 11+10+7+3+1, 11+10+7+4+1, 11+10+8+1, 11+10+8+2+1, 11+10+8+3+1, 11+10+8+4+1, 11+10+9+1, 11+10+9+2+1, 11+10+9+3+1, 11+10+9+4+1, 12+1, 12+2+1, 12+3+1, 12+4+1, 12+5+1, 12+5+2+1, 12+5+3+1, 12+5+4+1, 12+6+1, 12+6+2+1, 12+6+3+1, 12+6+4+1, 12+7+1, 12+7+2+1, 12+7+3+1, 12+7+4+1, 12+8+1, 12+8+2+1, 12+8+3+1, 12+8+4+1, 12+9+1, 12+9+2+1, 12+9+3+1, 12+9+4+1, 12+10+1, 12+10+2+1, 12+10+3+1, 12+10+4+1, 12+10+5+1, 12+10+5+2+1, 12+10+5+3+1, 12+10+5+4+1, 12+10+6+1, 12+10+6+

2+1, 12+10+6+3+1, 12+10+6+4+1, 12+10+7+1, 12+10+7+2+1, 12+10+7+3+1, 12+10+7+4+1, 12+10+8+1, 12+10+8+2+1, 12+10+8+3+1, 12+10+8+4+1, 12+10+9+1, 12+10+9+2+1, 12+10+9+3+1, 12+10+9+4+1, 12+11+1, 12+11+2+1, 12+11+3+1, 12+11+4+1, 12+11+5+1, 12+11+5+2+1, 12+11+5+3+1, 12+11+5+4+1, 12+11+6+1, 12+11+6+2+1, 12+11+6+3+1, 12+11+6+4+1, 12+11+7+1, 12+11+7+2+1, 12+11+7+3+1, 12+11+7+4+1, 12+11+8+1, 12+11+8+2+1, 12+11+8+3+1, 12+11+8+4+1, 12+11+9+1, 12+11+9+2+1, 12+11+9+3+1, 12+11+9+4+1, 12+11+10+1, 12+11+10+2+1, 12+11+10+3+1, 12+11+10+4+1, 12+11+10+5+1, 12+11+10+5+2+1, 12+11+10+5+3+1, 12+11+10+5+4+1, 12+11+10+6+1, 12+11+10+6+2+1, 12+11+10+6+3+1, 12+11+10+6+4+1, 12+11+10+7+1, 12+11+10+7+2+1, 12+11+10+7+3+1, 12+11+10+7+4+1, 12+11+10+8+1, 12+11+10+8+2+1, 12+11+10+8+3+1, 12+11+10+8+4+1, 12+11+10+9+1, 12+11+10+9+2+1, 12+11+10+9+3+1, 12+11+10+9+4+1, 13+1, 13+2+1, 13+3+1, 13+4+1, 13+5+1, 13+5+2+1, 13+5+3+1, 13+5+4+1, 13+6+1, 13+6+2+1, 13+6+3+1, 13+6+4+1, 13+7+1, 13+7+2+1, 13+7+3+1, 13+7+4+1, 13+8+1, 13+8+2+1, 13+8+3+1, 13+8+4+1, 13+9+1, 13+9+2+1, 13+9+3+1, 13+9+4+1, 13+10+1, 13+10+2+1, 13+10+3+1, 13+10+4+1, 13+10+5+1, 13+10+5+2+1, 13+10+5+3+1, 13+10+5+4+1, 13+10+6+1, 13+10+6+2+1, 13+10+6+3+1, 13+10+6+4+1, 13+10+7+1, 13+10+7+2+1, 13+10+7+3+1, 13+10+7+4+1, 13+10+8+1, 13+10+8+2+1, 13+10+8+3+1, 13+10+8+4+1, 13+10+9+1, 13+10+9+2+1, 13+10+9+3+1, 13+10+9+4+1, 13+11+1, 13+11+2+1, 13+11+3+1, 13+11+4+1, 13+11+5+1, 13+11+5+2+1, 13+11+5+3+1, 13+11+5+4+1, 13+11+6+1, 13+11+6+2+1, 13+11+6+3+1, 13+11+6+4+1, 13+11+7+1, 13+11+7+2+1, 13+11+7+3+1, 13+11+7+4+1, 13+11+8+1, 13+11+8+2+1, 13+11+8+3+1, 13+11+8+4+1, 13+11+9+1, 13+11+9+2+1, 13+11+9+3+1, 13+11+9+4+1, 13+11+10+1, 13+11+10+2+1, 13+11+10+3+1, 13+11+10+4+1, 13+11+10+5+1, 13+11+10+5+2+1, 13+11+10+5+3+1, 13+11+10+5+4+1, 13+11+10+6+1, 13+11+10+6+2+1, 13+11+10+6+3+1, 13+11+10+6+4+1, 13+11+10+7+1, 13+11+10+7+2+1, 13+11+10+7+3+1, 13+11+10+7+4+1, 13+11+10+8+1, 13+11+10+8+2+1, 13+11+10+8+3+1, 13+11+10+8+4+1, 13+11+10+9+1, 13+11+10+9+2+1, 13+11+10+9+3+1, 13+11+10+9+4+1, 14+1, 14+2+1, 14+3+1, 14+4+1, 14+5+1, 14+5+2+1, 14+5+3+1, 14+5+4+1, 14+6+1, 14+6+2+1, 14+6+3+1, 14+6+4+1, 14+7+1, 14+7+2+1, 14+7+3+1, 14+7+4+1, 14+8+1, 14+8+2+1, 14+8+3+1, 14+8+4+1, 14+9+1, 14+9+2+1, 14+9+3+1, 14+9+4+1, 14+10+1, 14+10+2+1, 14+10+3+1, 14+10+4+1, 14+10+5+1, 14+10+5+2+1, 14+10+5+3+1, 14+10+5+4+1, 14+10+6+1, 14+10+6+2+1, 14+10+6+3+1, 14+10+6+4+1, 14+10+7+1, 14+10+7+2+1, 14+10+7+3+1, 14+10+7+4+1, 14+10+8+1, 14+10+8+2+1, 14+10+8+3+1, 14+10+8+4+1, 14+10+9+1, 14+10+9+2+1, 14+10+9+3+1, 14+10+9+4+1, 14+11+1, 14+11+2+1, 14+11+3+1, 14+11+4+1, 14+11+5+1, 14+11+5+2+1, 14+11+5+3+1, 14+11+5+4+1, 14+11+6+1, 14+11+6+2+1, 14+11+6+3+1, 14+11+6+4+1, 14+11+7+1, 14+11+7+2+1, 14+11+7+3+1, 14+11+7+4+1, 14+11+8+1, 14+11+8+2+1, 14+11+8+3+1, 14+11+8+4+1, 14+11+9+1, 14+11+9+2+1, 14+11+9+3+1, 14+11+9+4+1, 14+11+10+1, 14+11+10+2+1, 14+11+10+3+1, 14+11+10+4+1, 14+11+10+5+1, 14+11+10+5+2+1, 14+11+10+5+3+1, 14+11+10+5+4+1, 14+11+10+6+1, 14+11+10+6+2+1, 14+11+10+6+3+1, 14+11+10+6+4+1, 14+11+10+7+1, 14+11+10+7+2+1, 14+11+10+7+3+1, 14+11+10+7+4+1, 14+11+10+8+1, 14+11+10+8+2+1, 14+11+10+8+3+1, 14+11+10+8+4+1, 14+11+10+9+1, 14+11+10+9+2+1, 14+11+10+9+3+1, 14+11+10+9+4+1, 15+1, 15+2+1, 15+3+1, 15+4+1, 15+5+1, 15+5+2+1, 15+5+3+1, 15+5+4+1, 15+6+1, 15+6+2+1, 15+6+3+1, 15+6+4+1, 15+7+1, 15+7+2+1, 15+7+3+1, 15+7+4+1, 15+8+1, 15+8+2+1, 15+8+3+1, 15+8+4+1, 15+9+1, 15+9+2+1, 15+9+3+1, 15+9+4+1, 15+10+1, 15+10+2+1, 15+10+3+1, 15+10+4+1, 15+10+5+1, 15+10+5+2+1, 15+10+5+3+1, 15+10+5+4+1, 15+10+6+1, 15+10+6+2+1, 15+10+6+3+1, 15+10+6+4+1, 15+10+7+1, 15+10+7+2+1, 15+10+7+3+1, 15+10+7+4+1, 15+10+8+1, 15+10+8+2+1, 15+10+8+3+1, 15+10+8+4+1, 15+10+9+1, 15+10+9+2+1, 15+10+9+3+1, 15+10+9+4+1.

In the list above the numbers refer to the embodiments according to their numbering provided hereinabove whereas "+" indicates the dependency from another embodiment. The different individualized embodiments are separated by commas. In other words, "11+9+4+1" for example refers to embodiment 11) depending on embodiment 9), depending on embodiment 4), depending on embodiment 1), i.e. embodiment "11+9+4+1" corresponds to the compounds of Formula (I) according to embodiment 1) further limited by all the features of the embodiments 4), 9), and 11).

17) A further aspect of the invention relates to compounds of Formula (I) according to embodiment 1) which are also compounds of Formula (V) (wherein it is understood that the absolute configuration is as depicted in the respective formula):

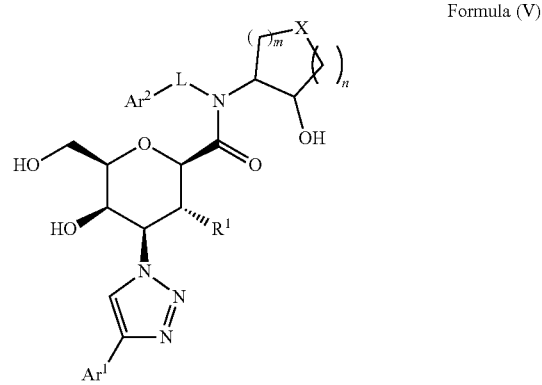

Formula (V)

wherein

X represents O or $NR^2$; wherein $R^2$ represents hydrogen, $C_{1-3}$-alkyl (especially methyl or ethyl), —CO—H, —$SO_2$—$C_{1-3}$-alkyl (especially $SO_2$—$CH_3$), or —CO—$C_{1-3}$-alkyl (especially —CO—$CH_3$);

$Ar^1$ represents phenyl, which is mono-, di-, tri-, tetra-, or penta-substituted (especially di-, or tri-substituted), wherein the substituents are independently selected from halogen; methyl; cyano; and methoxy (especially independently selected from halogen and methyl);

[group $Ar^1$ especially represents a group listed in embodiment 9) or any of its sub-embodiments]

$R^1$ represents
hydroxy;
$C_{1-3}$-alkoxy;
—O—CO—$C_{1-3}$-alkyl;
—O—$CH_2$—$CH_2$—OH; or
—O—$CH_2$—CO—OH;

[such substituent R¹ especially represents $C_{1-3}$-alkoxy (notably methoxy)]

L represents a direct bond or methylene (especially a direct bond); and

Ar² represents phenyl, wherein said phenyl is unsubstituted, mono-, di- or tri-substituted (especially mono-, or di-substituted) wherein the substituents are independently selected from methyl, methoxy, halogen, and cyano;

wherein the characteristics disclosed in embodiments 2) to 16) are intended to apply mutatis mutandis also to the compounds of Formula (V) according to embodiment 17).

18) Another embodiment relates to compounds of Formula (I) according to embodiment 1), which are selected from the following compounds:

(2R,3R,4S,5R,6R)—N-(3-chlorophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)-5-hydroxy-6-(hydroxymethyl)-N-((3S,4R)-4-hydroxytetrahydrofuran-3-yl)-N-(3-iodophenyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3,5-dichlorophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-chloro-5-cyanophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3,5-dibromophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-cyanophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-cyano-5-methoxyphenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-cyano-5-methylphenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-cyano-5-fluorophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)-4-(4-(4-bromo-2,3-difluorophenyl)-1H-1,2,3-triazol-1-yl)-N-(3,5-dichlorophenyl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)-4-(4-(4-bromo-2,3-difluorophenyl)-1H-1,2,3-triazol-1-yl)-N-(3-bromo-5-cyanophenyl)-5-hydroxy-6-(hydroxymethyl)- N-((3S,4R)-4-hydroxytetrahydrofuran-3-yl)-3-methoxytetrahydro-2H-pyran-2-carboxamide;

(2R,3R,4S,5R,6R)-4-(4-(4-bromo-2,3-difluorophenyl)-1H-1,2,3-triazol-1-yl)-N-(3-bromo-5-methylphenyl)-5-hydroxy-6-(hydroxymethyl)- N-((3S,4R)-4-hydroxytetrahydrofuran-3-yl)-3-methoxytetrahydro-2H-pyran-2-carboxamide;

(2R,3R,4S,5R,6R)—N-(3,5-dichlorophenyl)-4-(4-(3,5-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3,5-dibromophenyl)-4-(4-(3,5-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(3,5-difluoro-4-methylphenyl)-1H-1,2,3-triazol-1-yl)-5-hydroxy-6- (hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(3,5-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3,5-dichlorophenyl)-4-(4-(2,3-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(2,3-difluoro-4-methylphenyl)-1H-1,2,3-triazol-1-yl)-5-hydroxy-6- (hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(2,3-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)-4-(4-(4-chloro-3,5-difluorophenyl)-1H-1,2,3-triazol-1-yl)-N-(3,5-dichlorophenyl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)-4-(4-(4-chloro-3,5-difluorophenyl)-1H-1,2,3-triazol-1-yl)-N-(3,5-dibromophenyl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(4-chloro-3,5-difluorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(4-chloro-3,5-difluorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3,5-dichlorophenyl)-4-(4-(3,4-dichlorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3,5-dibromophenyl)-4-(4-(3,4-dichlorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(3,4-dichlorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(3,4-dichlorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-chlorophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)-5-hydroxy-6-(hydroxymethyl)-N-((3R,4S)-4-hydroxytetrahydrofuran-3-yl)-N-(3-iodophenyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3,5-dichlorophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-chloro-5-cyanophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3,5-dibromophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-cyanophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-cyano-5-methoxyphenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-cyano-5-methylphenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-cyano-5-fluorophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)-4-(4-(4-bromo-2,3-difluorophenyl)-1H-1,2,3-triazol-1-yl)-N-(3,5-dichlorophenyl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)-4-(4-(4-bromo-2,3-difluorophenyl)-1H-1,2,3-triazol-1-yl)-N-(3-bromo-5-cyanophenyl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)-4-(4-(4-bromo-2,3-difluorophenyl)-1H-1,2,3-triazol-1-yl)-N-(3-bromo-5-methylphenyl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3,5-dichlorophenyl)-4-(4-(3,5-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3,5-dibromophenyl)-4-(4-(3,5-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(3,5-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(3,5-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3,5-dichlorophenyl)-4-(4-(2,3-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(2,3-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(2,3-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)-4-(4-(4-chloro-3,5-difluorophenyl)-1H-1,2,3-triazol-1-yl)-N-(3,5-dichlorophenyl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)-4-(4-(4-chloro-3,5-difluorophenyl)-1H-1,2,3-triazol-1-yl)-N-(3,5-dibromophenyl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(4-chloro-3,5-difluorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(4-chloro-3,5-difluorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3,5-dichlorophenyl)-4-(4-(3,4-dichlorophenyl)-1H-1,2,3-triazol-1-yl)-5-hydroxy-6-(hydroxymethyl)-N—((3R,4S)-4-hydroxytetrahydrofuran-3-yl)-3-methoxytetrahydro-2H-pyran-2-carboxamide;

(2R,3R,4S,5R,6R)—N-(3,5-dibromophenyl)-4-(4-(3,4-dichlorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(3,4-dichlorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(3,4-dichlorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3,5-dichlorophenyl)-5-hydroxy-6-(hydroxymethyl)-N-((3S,4S)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-cyanophenyl)-5-hydroxy-6-(hydroxymethyl)-N-((3S,4S)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-5-hydroxy-6-(hydroxymethyl)-N-((3S,4S)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)-4-(4-(4-bromo-2,3-difluorophenyl)-1H-1,2,3-triazol-1-yl)-N-(3,5-dichlorophenyl)-5-hydroxy-6-(hydroxymethyl)-N-((3S,4S)-4-hydroxypyrrolidin-3-yl)-3-methoxytetrahydro-2H-pyran-2-carboxamide;

(2R,3R,4S,5R,6R)—N-(3,5-dichlorophenyl)-4-(4-(2,3-difluoro-4-methylphenyl)-1H-1,2,3-triazol-1-yl)-5-hydroxy-6-(hydroxymethyl)-N-((3S,4S)-4-hydroxypyrrolidin-3-yl)-3-methoxytetrahydro-2H-pyran-2-carboxamide;

(2R,3R,4S,5R,6R)—N-(3-bromo-5-methylphenyl)-4-(4-(2,3-difluoro-4-methylphenyl)-1H-1,2,3-triazol-1-yl)-5-hydroxy-6-(hydroxymethyl)-N-((3S,4S)-4-hydroxypyrrolidin-3-yl)-3-methoxytetrahydro-2H-pyran-2-carboxamide;

(2R,3R,4S,5R,6R)—N-(3,5-dichlorophenyl)-4-(4-(3,4-dichlorophenyl)-1H-1,2,3-triazol-1-yl)-5-hydroxy-6-(hydroxymethyl)-N—((3S,4S)-4-hydroxypyrrolidin-3-yl)-3-methoxytetrahydro-2H-pyran-2-carboxamide;

(2R,3R,4S,5R,6R)—N-(3,5-dichlorophenyl)-5-hydroxy-6-(hydroxymethyl)-N-((3R,4R)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-cyanophenyl)-5-hydroxy-6-(hydroxymethyl)-N-((3R,4R)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-5-hydroxy-6-(hydroxymethyl)-N-((3R,4R)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-4-(4-(2,3-difluoro-4-methylphenyl)-1H-1,2,3-triazol-1-yl)-5-hydroxy-6-(hydroxymethyl)-N-((3R,4R)-4-hydroxypyrrolidin-3-yl)-3-methoxytetrahydro-2H-pyran-2-carboxamide;

(2R,3R,4S,5R,6R)—N-(3-bromo-5-methylphenyl)-4-(4-(3,5-difluoro-4-methylphenyl)-1H-1,2,3-triazol-1-yl)-5-hydroxy-6-(hydroxymethyl)-N-((3S,4S)-4-hydroxypyrrolidin-3-yl)-3-methoxytetrahydro-2H-pyran-2-carboxamide;

(2R,3R,4S,5R,6R)—N-(3-bromo-5-methylphenyl)-4-(4-(3,5-difluoro-4-methylphenyl)-1H-1,2,3-triazol-1-yl)-5-hydroxy-6-(hydroxymethyl)-N-((3R,4R)-4-hydroxypyrrolidin-3-yl)-3-methoxytetrahydro-2H-pyran-2-carboxamide;

(2R,3R,4S,5R,6R)—N-((3S,4S)-1-acetyl-4-hydroxypyrrolidin-3-yl)-N-(3,5-dichlorophenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-((3S,4S)-1-acetyl-4-hydroxypyrrolidin-3-yl)-N-(3-bromo-5-methylphenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-((3S,4S)-1-acetyl-4-hydroxypyrrolidin-3-yl)-4-(4-(4-bromo-2,3-difluorophenyl)-1H-1,2,3-triazol-1-yl)-N-(3,5-dichlorophenyl)-5-hydroxy-6-(hydroxymethyl)-3-methoxytetrahydro-2H-pyran-2-carboxamide;

(2R,3R,4S,5R,6R)—N-((3S,4S)-1-acetyl-4-hydroxypyrrolidin-3-yl)-N-(3,5-dibromophenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3S,4S)-1-acetyl-4-hydroxypyrrolidin-3-yl)-N-(3-bromo-5-methylphenyl)-4-(4-(3,5-difluoro-4-methylphenyl)- 1H-1,2,3-triazol-1-yl)-5-hydroxy-6-(hydroxymethyl)-3-methoxytetrahydro-2H-pyran-2-carboxamide;

(2R,3R,4S,5R,6R)—N-((3S,4S)-1-acetyl-4-hydroxypyrrolidin-3-yl)-N-(3-bromo-5-methylphenyl)-4-(4-(4-chloro-3,5-difluorophenyl)- 1H-1,2,3-triazol-1-yl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-N-(3,5-dichlorophenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-((3R,4R)-1-acetyl-4-hydroxypyrrolidin-3-yl)-N-(3-bromo-5-cyanophenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-((3R,4R)-1-acetyl-4-hydroxypyrrolidin-3-yl)-N-(3-bromo-5-methylphenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-((3R,4R)-1-acetyl-4-hydroxypyrrolidin-3-yl)-4-(4-(4-bromo-2,3-difluorophenyl)-1H-1,2,3-triazol-1-yl)-N-(3,5-dichlorophenyl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-N-(3,5-dibromophenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-N-(3-bromo-5-methylphenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-N-(3-bromo-5-methylphenyl)-4-(4-(4-chloro- 3,5-difluorophenyl)- 1H-1,2,3-triazol-1-yl)-5-hydroxy-6-(hydroxymethyl)-3-methoxytetrahydro-2H-pyran-2-carboxamide;

(2R,3R,4S,5R,6R)—N-((3S,4S)-1-acetyl-4-hydroxypyrrolidin-3-yl)-N-(3,5-dibromophenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-((3R,4R)-1-acetyl-4-hydroxypyrrolidin-3-yl)-N-(3,5-dibromophenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-((3S,4S)-1-acetyl-4-hydroxypyrrolidin-3-yl)-N-(3,5-dichlorophenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-N-(3,5-dichlorophenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3S,4S)-1-acetyl-4-hydroxypyrrolidin-3-yl)-4-(4-(4-chloro-3,5-difluorophenyl)-1H-1,2,3-triazol-1-yl)-N-(3,5-dichlorophenyl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-4-(4-(4-chloro-3,5-difluorophenyl)-1H-1,2,3-triazol-1-yl)-N-(3,5-dichlorophenyl)-5-hydroxy-6-(hydroxymethyl)-3-methoxytetrahydro-2H-pyran-2-carboxamide;

(2R,3R,4S,5R,6R)—N-((3S,4S)-1-acetyl-4-hydroxypyrrolidin-3-yl)-4-(4-(4-chloro-3,5-difluorophenyl)-1H-1,2,3-triazol-1-yl)-N-(3,5-dibromophenyl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-4-(4-(4-chloro-3,5-difluorophenyl)-1H-1,2,3-triazol-1-yl)-N-(3,5-dibromophenyl)-5-hydroxy-6-(hydroxymethyl)-3-methoxytetrahydro-2H-pyran-2-carboxamide;

(2R,3R,4S,5R,6R)—N-((3S,4S)-1-acetyl-4-hydroxypyrrolidin-3-yl)-N-(3,5-dichlorophenyl)-4-(4-(3,4-dichlorophenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-N-(3,5-dichlorophenyl)-4-(4-(3,4-dichlorophenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-(3-bromo-5-cyanophenyl)-N-((3S,4S)-1-formyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-N-((3S,4S)-1-formyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)-4-(4-(4-bromo-2,3-difluorophenyl)-1H-1,2,3-triazol-1-yl)-N-(3,5-dichlorophenyl)-N—((3S,4S)-1-formyl-4-hydroxypyrrolidin-3-yl)-5-hydroxy-6-(hydroxymethyl)-3-methoxytetrahydro-2H-pyran-2-carboxamide;

(2R,3R,4S,5R,6R)—N-(3-bromo-5-methylphenyl)-4-(4-(2,3-difluoro-4-methylphenyl)-1H-1,2,3-triazol-1-yl)-N-((3S,4S)-1-formyl-4-hydroxypyrrolidin-3-yl)-5-hydroxy-6-(hydroxymethyl)-3-methoxytetrahydro-2H-pyran-2-carboxamide;

(2R,3R,4S,5R,6R)—N-(3-bromo-5-cyanophenyl)-N-((3R,4R)-1-formyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-N-((3R,4R)-1-formyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-4-(4-(2,3-difluoro-4-methylphenyl)-1H-1,2,3-triazol-1-yl)-N-((3R,4R)-1-formyl-4-hydroxypyrrolidin-3-yl)-5-hydroxy-6-(hydroxymethyl)-3-methoxytetrahydro-2H-pyran-2-carboxamide;

(2R,3R,4S,5R,6R)—N-(3-bromo-5-methylphenyl)-5-hydroxy-N-((3S,4S)-4-hydroxy-1-methylpyrrolidin-3-yl)-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-N-((3S,4S)-1-ethyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-5-hydroxy-N-((3S,4S)-4-hydroxy-1-(methylsulfonyl) pyrrolidin-3-yl)-6-(hydroxymethyl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3,5-dichlorophenyl)-5-hydroxy-6-(hydroxymethyl)-N-((3R,4S)-3-hydroxytetrahydro-2H-pyran-4-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-chloro-5-cyanophenyl)-5-hydroxy-6-(hydroxymethyl)-N-((3R,4S)-3-hydroxytetrahydro-2H-pyran-4-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-cyanophenyl)-5-hydroxy-6-(hydroxymethyl)-N-((3R,4S)-3-hydroxytetrahydro-2H-pyran-4-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-5-hydroxy-6-(hydroxymethyl)-N-((3R,4S)-3-hydroxytetrahydro-2H-pyran-4-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3,5-dichlorophenyl)-5-hydroxy-6-(hydroxymethyl)-N-((3S,4R)-3-hydroxytetrahydro-2H-pyran-4-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-5-hydroxy-6-(hydroxymethyl)-N-((3S,4R)-3-hydroxytetrahydro-2H-pyran-4-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3,5-dichlorophenyl)-5-hydroxy-6-(hydroxymethyl)-N-((3S,4S)-4-hydroxytetrahydro-2H-pyran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-5-hydroxy-6-(hydroxymethyl)-N-((3S,4S)-4-hydroxytetrahydro-2H-pyran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3,5-dichlorophenyl)-5-hydroxy-6-(hydroxymethyl)-N-((3R,4R)-4-hydroxytetrahydro-2H-pyran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-5-hydroxy-6-(hydroxymethyl)-N-((3R,4R)-4-hydroxytetrahydro-2H-pyran-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3,5-dichlorophenyl)-5-hydroxy-6-(hydroxymethyl)-N-((3S,4S)-3-hydroxypiperidin-4-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-cyanophenyl)-5-hydroxy-6-(hydroxymethyl)-N-((3S,4S)-3-hydroxypiperidin-4-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-5-hydroxy-6-(hydroxymethyl)-N-((3S,4S)-3-hydroxypiperidin-4-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-5-hydroxy-6-(hydroxymethyl)-N-((3R,4R)-3-hydroxypiperidin-4-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3,5-dichlorophenyl)-5-hydroxy-6-(hydroxymethyl)-N-((3S,4S)-4-hydroxypiperidin-3-yl)-3-methoxy-4-(4-(3,4,5-trifluorophenyl)-1H-1,2,3-triazol-1-yl)tetrahydro-2H-pyran-2-carboxamide;

(2R,3R,4S,5R,6R)—N-(3-bromo-5-methylphenyl)-5-hydroxy-6-(hydroxymethyl)-N-((3S,4S)-4-hydroxypiperidin-3-yl)-3-methoxy-4-(4-(3,4,5-trifluorophenyl)-1H-1,2,3-triazol-1-yl)tetrahydro-2H-pyran-2-carboxamide; and (2R,3R,4S,5R,6R)—N-(3-bromo-5-methylphenyl)-5-hydroxy-6-(hydroxymethyl)-N-((3R,4R)-4-hydroxypiperidin-3-yl)-3-methoxy-4-(4-(3,4,5-trifluorophenyl)-1H-1,2,3-triazol-1-yl)tetrahydro-2H-pyran-2-carboxamide.

The compounds of Formula (I) according to embodiments 1) to 18) and their pharmaceutically acceptable salts can be used as medicaments, e.g. in the form of pharmaceutical compositions for enteral (such especially oral e.g. in form of a tablet or a capsule) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention/prophylaxis or treatment of a disease or disorder mentioned herein comprising administering to a subject a pharmaceutically active amount of a compound of Formula (I) according to embodiments 1) to 18). In a sub-embodiment of the invention, the administered amount is comprised between 1 mg and 1000 mg per day.

For avoidance of any doubt, if compounds are described as useful for the prevention/prophylaxis or treatment of certain diseases, such compounds are likewise suitable for use in the preparation of a medicament for the prevention/prophylaxis or treatment of said diseases. Likewise, such compounds are also suitable in a method for the prevention/prophylaxis or treatment of such diseases, comprising administering to a subject (mammal, especially human) in need thereof, an effective amount of such compound.

19) Another embodiment relates to the compounds of formula (I) as defined in any one of embodiments 1) to 18) which are useful for the prevention/prophylaxis or treatment of diseases and disorders that are related to galectin-3 binding to natural ligands.

Such diseases and disorders that are related to Gal-3 binding to natural ligands are especially diseases and disorders in which inhibition of the physiological activity of Gal-3 is useful, such as diseases in which a Gal-3 receptor participates, is involved in the etiology or pathology of the disease, or is otherwise associated with at least one symptom of the disease.

Diseases or disorders that are related to galectin-3 binding to natural ligands may in particular be defined as including:

fibrosis of organs comprising:
all forms of lung/pulmonary fibrosis including all forms of fibrosing interstitial lung diseases, especially idiopathic pulmonary fibrosis (alternatively named cryptogenic fibrosing alveolitis); pulmonary fibrosis secondary to systemic inflammatory disease such as rheumatoid arthritis, scleroderma (systemic sclerosis, SSc), lupus (systemic lupus erythematosus, SLE), polymyositis, or mixed connective tissue disease (MCTD); pulmonary fibrosis secondary to sarcoidosis; iatrogenic pulmonary fibrosis including radiation-induced fibrosis; silicosis-induced pulmonary fibrosis; asbestos-induced pulmonary fibrosis; and pleural fibrosis;

renal/kidney fibrosis, including renal fibrosis caused by/associated with chronic kidney disease (CKD), (acute or chronic) renal failure, tubulointerstitial nephritis, and/or chronic nephropathies such as (primary) glomerulonephritis and glomerulonephritis secondary to systemic inflammatory diseases such as SLE or SSc, diabetes, focal segmental glomerular sclerosis, IgA nephropathy, hypertension, renal allograft, and Alport syndrome;

all forms of liver/hepatic fibrosis (associated or not with portal hypertension) including cirrhosis, alcohol-induced liver fibrosis, nonalcoholic steatohepatitis, biliary duct injury, primary biliary cirrhosis (also known as primary biliary cholangitis), infection- or viral-induced liver fibrosis (e.g. chronic HCV infection), and autoimmune hepatitis;

all forms of heart/cardiac fibrosis, including heart/cardiac fibrosis associated with cardiovascular diseases, heart failure, Fabry disease, CKD; diabetes, hypertension, or hypercholesterolemia;

gut fibrosis, including gut fibrosis secondary to SSc, and radiation-induced gut fibrosis;

skin fibrosis, including SSc and skin scarring;

head and neck fibrosis, including radiation-induced head and neck fibrosis;

eye/corneal fibrosis, including scarring (e.g. sequelae of laser-assisted in situ keratomileusis, or trabeculectomy);

hypertrophic scarring and keloids, including burn-induced or surgical hypertrophic scarring and keloids;

fibrosis sequelae of organ transplant (including corneal transplant);
and other fibrotic diseases including endometriosis, spinal cord fibrosis, myelofibrosis, perivascular and aterial fibrosis; as well as formation of scar tissue, Peyronie's disease, abdominal or bowel adhesions, bladder fibrosis, fibrosis of the nasal passages, and fibrosis mediated by fibroblasts;

(acute or chronic) liver diseases and disorders including acute and chronic viral hepatitis; cirrhosis caused by/associated with arthritis and vasculitis; metabolic liver diseases caused by/associated with arthritis, myocarditis, diabetes, or neurologic symptoms; cholestatic diseases caused by/associated with hyperlipidaemia, inflammatory bowel disease (IBD), or ulcerative colitis; liver tumors; autoimmune hepatitis and cirrhosis caused by/associated with celiac disease, autoimmune haemolytic anaemia, IBD, autoimmune thyroiditis, ulcerative colitis, diabetes, glomerulonephritis, pericarditis, autoimmune thyroiditis, hyperthyroidism, polymyositis, Sjörgen syndrome, panniculitis, alveolitis or alcoholic steatosis; cirrhosis associated with dementia; cirrhosis associated with peripheral neuropathy; cirrhosis caused by/associated with oral or oesophageal cancer; non-alcoholic fatty liver disease (especially non-alcoholic steatohepatitis) caused by/associated with obesity, metabolic syndrome or type 2 diabetes; hepatic blood vessel disorders (including Budd-Chiari syndrome, portal vein thrombosis, sinusoidal obstruction syndrome); acute and chronic liver failure (associated or not with portal hypertension); liver hypofunction;

acute kidney injury and chronic kidney disease (CKD) [especially CKD of stages 1 to 5 as defined by the Kidney Disease Improving Global Outcomes (KDIGO) Guidelines], in particular CKD (notably of these stages) caused by/associated with cardiac diseases (also referred to as cardio-renal syndrome type 1 and type 2), or caused by/associated with hypertension, or caused by/associated with diabetes (also referred to as diabetic kidney disease (DKD), including DKD associated with hypertension), wherein such diabetes especially is type 1 or type 2 diabetes), or caused by/associated with inflammatory diseases and disorders (such as glomerulonephritis and glomerulonephritis secondary to systemic inflammatory diseases such as SLE or SSc, tubulo-interstitial nephritis, vasculitis, sepsis, urinary tract infection), or caused by/associated with polycystic kidney disease, or caused by/associated with obstructive nephropathy (including calculi, benign prostatic hyperplasia, prostate cancer, retroperitoneal pelvic tumor), or caused by/associated with symptoms associated with neuropathic bladder disease); as well as acute and chronic renal failure;

cardiovascular diseases and disorders (including atherosclerosis caused by/associated with hypertension, hypercholesterolemia, diabetes, inflammation, obesity, elderly/age; peripheral arterial disease caused by/associated with hypertension, hypercholesterolemia, diabetes, elderly/age; deep venous thrombosis; pulmonary embolism caused by/associated with obesity or cancer; aortic aneurysm and dissection caused by/associated with elderly/age, hypertension, Marfan syndrome, congenital heart disorders, inflammatory or infectious disorders; cerebrovascular disease caused by/associated with hypertension, atrial fibrillation, hypercholesterolemia, diabetes, elderly/age; coronary heart disease caused by/associated with hypertension, hypercholesterolemia, diabetes, elderly/age, or CKD (especially CKD of stages 1 to 5 as defined by the Kidney Disease Improving Global Outcomes (KDIGO) Guidelines); rheumatic heart disease caused by/associated with bacterial infection; heart and vascular tumors; cardiomyopathy and arrythmias; valvular heart disease (including valvular calcification and degenerative aortic stenosis); inflammatory heart disease caused by/associated with infection, carditis, glomerulonephritis, cancer; heart failure (HF) defined as including especially congestive HF, including in particular systolic HF/HF with reduced ejection fraction (HFrEF), and diastolic HF/HF with preserved ejection fraction (HFpEF);

interstitial lung diseases and disorders (including smoking-related interstitial lung disease; interstitial lung disease associated with/caused by chronic obstructive pulmonary disease; interstitial pneumonia associated with collagen vascular disease (including usual interstitial pneumonia), or pneumonia);

cell proliferative diseases and cancers (including solid tumors, solid tumor metastasis, carcinoma, sarcoma, myeloma (and multiple myeloma), leukemia, lymphoma, mixed types of cancers, vascular fibroma, Kaposi's sarcoma, chronic lymphocytic leukemia (CLL), spinal cord tumors and invasive metastasis of cancer cells; in particular said cell proliferative diseases and cancers are cancers of the thyroid gland, the central nervous system, the tongue, the breast, the gastric system, the head and neck squamous cell, the pancreas, the bladder, the kidney, the liver, the parathyroid, or the salivary glands; or lymphoma; carcinoma, non-small cell lung cancer, melanoma or neuroblastoma);

inflammatory and autoimmune diseases and disorders including chronic and acute inflammatory and autoimmune diseases and disorders (in particular including sepsis, Q-fever, asthma, rheumatoid arthritis, multiple sclerosis, SLE, SSc, polymyositis, plaque psoriasis (including psoriasis caused by/associated with NASH), atopic dermatitis, inflammatory renal/kidney diseases such as nephropathy (including diabetic nephropathy, glomerulonephritis, tubulointerstitial nephritis), inflammatory cardiac/heart diseases, inflammatory lung/lung related diseases; inflammatory liver/liver related diseases; diabetes (type 1 or type 2) and diabetes related diseases such as diabetic vasculopathy, diabetic nephropathy, diabetic retinopathy, diabetic peripheral neuropathy or skin related condition; viral encephalitis; and COVID-19 and sequelae thereof);

gastrointestinal tract diseases and disorders (including irritable bowel syndrome (IBS), inflammatory bowel disease (IBD), gastritis, and abnormal pancreatic secretion);

pancreatic diseases and disorders (including pancreatitis, e.g. associated with cystic fibrosis);

abnormal angiogenesis-associated diseases and disorders (including arterial obstruction);

brain-associated diseases and disorders (including stroke and cerebral haemorrhage);

neuropathic pain and peripheral neuropathy;

ocular diseases and disorders (including dry eye disease (dry eye syndrome), macular degeneration (AMD) associated with age, diabetes related disease (diabetic retinopathy), proliferative vitreoretinopathy (PVR), cicatricial pemphigoid, and glaucoma (including glaucoma associated with elevated intraocular pressure, and ocular scarring after glaucoma filtration surgery), and corneal angiogenesis/neovascularization); and transplant rejection comprising rejection of transplanted organs such as kidney, liver, heart, lung, pancreas, cornea, and skin; graft-versus-host diseases brought about by hematopoietic stem cell transplantation; chronic allograft rejection and chronic allograft vasculopathy; and sequelae of such transplant rejection.

20) A further embodiment relates to the compounds of formula (I) for use according to embodiment 19) wherein said compounds are for use in the prevention/prophylaxis or treatment of fibrosis of organs including liver/hepatic fibrosis, renal/kidney fibrosis, lung/pulmonary fibrosis, heart/cardiac fibrosis, eye/corneal fibrosis, and skin fibrosis; as well as gut fibrosis, head and neck fibrosis, hypertrophic scarring and keloids; and fibrosis sequelae of organ transplant.

21) A further embodiment relates to the compounds of formula (I) for use according to embodiment 19) wherein said compounds are for use in the prevention/prophylaxis or treatment of cardiovascular diseases and disorders.

22) A further embodiment relates to the compounds of formula (I) for use according to embodiment 19) wherein said compounds are for use in the prevention/prophylaxis or treatment of acute kidney injury and chronic kidney disease (CKD).

23) A further embodiment relates to the compounds of formula (I) for use according to embodiment 19) wherein said compounds are for use in the prevention/prophylaxis or treatment of (acute or chronic) liver diseases and disorders.

24) A further embodiment relates to the compounds of formula (I) for use according to embodiment 19) wherein said compounds are for use in the prevention/prophylaxis or treatment of interstitial lung diseases and disorders.

25) A further embodiment relates to the compounds of formula (I) for use according to embodiment 19) wherein said compounds are for use in the prevention/prophylaxis or treatment of ocular diseases and disorders.

26) A further embodiment relates to the compounds of formula (I) for use according to embodiment 19) wherein said compounds are for use in the prevention/prophylaxis or treatment of cell proliferative diseases and cancers.

Especially such cell proliferative diseases and cancers are cancers of the thyroid gland, the central nervous system, the tongue, the breast, the gastric system, the head and neck squamous cell, the pancreas, the bladder, the kidney, the liver, the parathyroid, or the salivary glands; or lymphoma; carcinoma, non-small cell lung cancer, melanoma or neuroblastoma.

27) A further embodiment relates to the compounds of formula (I) for use according to embodiment 19) wherein said compounds are for use in the prevention/prophylaxis or treatment of chronic or acute inflammatory and autoimmune diseases and disorders.

28) A further embodiment relates to the compounds of formula (I) for use according to embodiment 19) wherein said compounds are for use in the prevention/prophylaxis or treatment of gastrointestinal tract diseases and disorders.

29) A further embodiment relates to the compounds of formula (I) for use according to embodiment 19) wherein said compounds are for use in the prevention/prophylaxis or treatment of pancreatic diseases and disorders.

30) A further embodiment relates to the compounds of formula (I) for use according to embodiment 19) wherein said compounds are for use in the prevention/prophylaxis or treatment of abnormal angiogenesis-associated diseases and disorders.

31) A further embodiment relates to the compounds of formula (I) for use according to embodiment 19) wherein said compounds are for use in the prevention/prophylaxis or treatment of brain-associated diseases and disorders.

32) A further embodiment relates to the compounds of formula (I) for use according to embodiment 19) wherein said compounds are for use in the prevention/prophylaxis or treatment of neuropathic pain and peripheral neuropathy.

33) A further embodiment relates to the compounds of formula (I) for use according to embodiment 19) wherein said compounds are for use in the treatment of transplant rejection.

Besides, any preferences and (sub-)embodiments indicated for the compounds of Formula (I) (whether for the compounds themselves, salt thereof, compositions containing the compounds or salts thereof, or uses of the compounds or salts thereof, etc.) apply mutatis mutandis to compounds of Formula (II), (III), (IV), $(I_S)$, $(II_S)$, $(III_S)$, $(IV_S)$, $(I_R)$, $(II_R)$, $(III_R)$, $(IV_R)$ and (V).

Preparation of Compounds of Formula (I)

The compounds of Formula (I) can be prepared by well-known literature methods, by the methods given below, by the methods given in the experimental part below or by analogous methods. Optimum reaction conditions may vary with the particular reactants or solvents used, but such conditions can be determined by a person skilled in the art by routine optimisation procedures. In some cases, the order of carrying out the following reaction schemes, and/or reaction steps, may be varied to facilitate the reaction or to avoid unwanted by-products. In the general sequence of reactions outlined below, the integers n and m, and the generic groups $R^1$, L, $Ar^1$, $Ar^2$, n and m are as defined for Formula (I). Other abbreviations used herein are explicitly defined, or are as defined in the experimental section. In some instances, the generic groups $R^1$, L, $Ar^1$, $Ar^2$, n and m might be incompatible with the assembly illustrated in the schemes below and so will require the use of protecting groups (Pg). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. In some cases, the final product may be further modified, for example, by manipulation of substituents to give a new final product. These manipulations may include, but are not limited to, reduction, oxidation, alkylation, acylation, hydrolysis and transition-metal catalysed cross-coupling reactions which are commonly known to those skilled in the art. The compounds obtained may also be converted into salts, especially pharmaceutically acceptable salts, in a manner known per se.

Compounds of Formula (I) of the present invention can be prepared according to the general sequence of reactions outlined below. Only a few of the synthetic possibilities leading to compounds of Formula (I) are described.

Compounds of Formula (I) are prepared by coupling a compound of Structure 1 where R is either hydrogen, a suitable protective group (Pg) or $R^1$ (as defined in Formula (I)) with a compound of Structure 2 to give Structure 3. The coupling reaction is performed using standard peptide coupling conditions such as DCC, HOBT, or T3P in presence of a base such as TEA or DIPEA in a suitable solvent such as DCM or DMF or mixtures thereof. Alternatively, $POCl_3$ can be used with pyridine as a base. In Structure 2 and 3, Pg is a suitable protective group such as acetyl, trimethylsilyl (TMS) or tert-butyl dimethylsilyl (TBS), or benzyl, which are well known to the person skilled in the art. The hydroxy groups in position 4 and 6 of Structure 1 can be protected with cyclic protective groups such as isopropylidene, benzylidene or bis-tert-butyl silyl groups. R is either a suitable protective group (Pg) or the group OR corresponds to $R^1$ (as defined in Formula (I)). Compounds of Structure 3 are then deprotected to yield compounds of Formula (I).

Structure 1

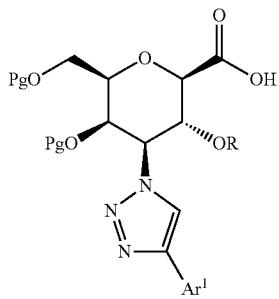

Structure 2

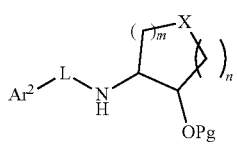

Structure 3

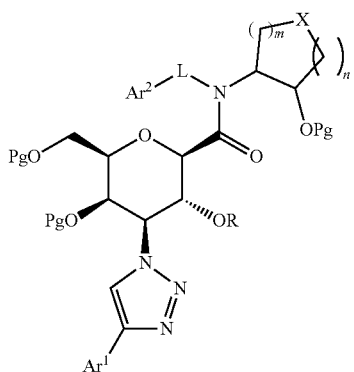

In the case Pg represents an acyl protective group, such a protective group can be cleaved under standard conditions, e.g. by water or an alcohol in the presence or absence of additional solvents such as THF, dioxane, etc. and in the presence of a base such as $K_2CO_3$, NaOH, LiOH. In the case wherein such a protective group represents a benzyl group, the protective group can be cleaved e.g. by hydrogen in the presence of a catalyst such as Pd/C, $PtO_2$ in methanol, EA, THF, etc. or mixtures thereof, or by $BBr_3$ in a solvent such as DCM. In the case wherein such a protective group is TMS or TBS, the protective group is cleaved using fluoride ions such as TBAF of HF in pyridine. Alternatively, silyl protective groups are removed under mild acidic conditions such as aqueous AcOH at temperatures between rt and reflux. In the case where Pg is a cyclic protective group such as isopropylidene, benzylidene and bis-tert-butyl silylene group, the cleavage can be performed under acidic conditions using aqueous AcOH or TFA.

Structure 4

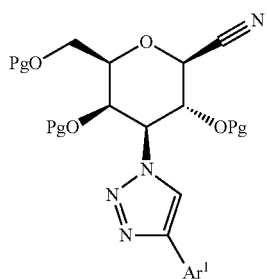

Structure 5

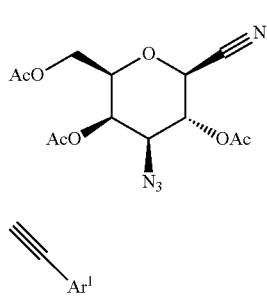

Structure 6

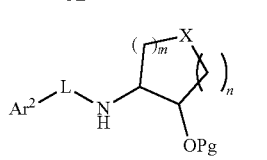

Structure 7

The compounds of Structure 1 are prepared by hydrolysis of the nitrile function in Structure 4 to the carboxylic acid using aq. acidic (conc. HCl) or basic (NaOH) conditions at temperatures between 20 and 100° C., followed by suitable protection or modification of the free hydroxyl groups. Structure 4 in turn is obtained e.g. by reacting a compound of Structure 5 with a compound of Structure 6 in the presence of CuI and DIPEA in solvents such as THF or DMF (*Click Chemistry in Glycoscience: New Development and Strategies*, 1st Edition, 2013, John Wiley& Sons), alternatively the reaction can be run on a commercial continuous-flow reactor (Vapourtec) using a copper coil in a solvent such as THF. Compounds of Structure 6 are either commercially available or can be prepared according to procedures known to a person skilled in the art (Synthesis 2011, 22, 3604-3611). Compounds of Structure 5 can be prepared from corresponding gulofuranose derivatives through methods well known to a person skilled in the art (*Carbohydrate Research* 1994, 251, 33-67; *Bioorg. Med. Chem.* 2002, 10, 1911-2013).

Compounds of Structure 2 are obtained by protection of compounds of Structure 7 with a suitable silyl-based protective group under standard conditions. Compounds of Structure 7 are obtained by reaction of 3,6-dioxabicyclo[3.1.0]hexane, tert-butyl 6-oxa-3-azabicyclo[3.1.0]hexane-3-carboxylate, 1-(6-oxa-3-azabicyclo[3.1.0]hexan-3-ypethan-1-one, 3,7-dioxabicyclo[4.1.0]heptane or tert-butyl 7-oxa-3-azabicyclo[4.1.0]heptane-3-carboxylate with an amine.

Compounds of Structure 2 are used in racemic form or as separated enantiomers for the coupling with compounds of Structure 1. The diastereomers of Structure 3 or Formula I (after the deprotection) are separated using techniques which are well known to the person skilled in the art, such as chiral preparative HPLC using achiral or chiral stationary phases. Typically used achiral or chiral stationary phases for chiral preparative HPLC are such as a Waters XBridge C18, 10 μm OBD, 30×75 mm, or Daicel Chiralcel OZ—H (5 um) column, Daicel ChiralCel OJ-H (5-10 μm) column, a ChiralPak IC (5 μm) column, ChiralPak ID (5 μm) column, ChiralPak IG (5 μm) column, ChiralPak IH (5 μm) column, ChiralPak IE (5 μm) column, ChiralPak AS-H (5 μm), AD-H (5 μm or IB (5 μm) column, respectively.

Typical conditions of chiral HPLC are an isocratic mixture of eluent A ($CO_2$) and eluent B (DCM/MeOH, MeCN/MeOH, MeCN/EtOH, 0.1% $Et_2NH$ in EtOH, MeOH, EtOH, iPrOH), at a flow rate of 0.8 to 160 mL/min. In some cases, enantiomerically pure form of compounds of Structure 2 are used for the amide coupling with compounds of Structure 1 delivering pure enantiomers of compounds of Structure 3 and Formula I, respectively.

In cases where diastereomers were not separated, the $IC_{50}$ values are measured for the mixture of diastereomers.

Experimental Part

The following examples illustrate the invention but do not at all limit the scope thereof.

All temperatures are stated in °C. Commercially available starting materials were used as received without further purification. Unless otherwise specified, all reactions were carried out under an atmosphere of nitrogen or argon. Compounds were purified by flash chromatography on silica gel (Biotage, Redisep), by prep TLC (TLC-plates from Merck, Silica gel 60 $F_{254}$) or by preparative H PLC. Compounds described in the invention are characterized by $^1$H-NMR (Bruker Neo, 400 MHz Ultra Shield™ or Bruker Avance III HD, Ascend 500 MHz); chemical shifts are given in ppm relative to the solvent used; multiplicities: s=singlet, d=doublet, t=triplet, q=quadruplet, quint=quintuplet, hex=hexet, hept=heptet, m=multiplet, br=broad, coupling constants are given in Hz) and/or by LCMS (retention time $t_R$ is given in min; molecular weight obtained for the mass spectrum is given in g/mol) using the conditions listed below.

Characterization methods used:
The LC-MS retention times have been obtained using the following elution conditions:

A) LC-MS (A)

Zorbax RRHD SB-Aq, 1.8 μm, 2.1×50 mm column thermostated at 40° C. The two elution solvents were as follows: solvent A=water+0.04% TFA; solvent B=MeCN. The eluent flow rate was 0.8 mL/min and the characteristics of the eluting mixture proportion in function of the time t from start of the elution are summarized in the table below (a linear gradient being used between two consecutive time points):

|  | t (min) | | | | |
| --- | --- | --- | --- | --- | --- |
|  | 0 | 0.01 | 1.20 | 1.90 | 2.10 |
| Solvent A (%) | 95 | 95 | 5 | 5 | 95 |
| Solvent B (%) | 5 | 5 | 95 | 95 | 5 |

Detection: UV at 210 nm.

The purifications by preparative LC-MS have been performed using the conditions described hereafter.

B) Preparative LC-MS (I)

A Zorbax column (Zorbax Dr. Maisch, 5 μm, 30×75 mm) was used. The two elution solvents were as follows: solvent A=water+0.5% of a solution of formic acid in water; solvent B=MeCN. The eluent flow rate was 75 mUmin and the characteristics of the eluting mixture proportion in function of the time t from start of the elution are summarized in the tables below (a linear gradient being used between two consecutive time points):

|  | t (min) | | | |
| --- | --- | --- | --- | --- |
|  | 0 | 3.0 | 6.0 | 6.7 |
| Solvent A (%) | 50 | 5 | 5 | 50 |
| Solvent B (%) | 50 | 95 | 95 | 50 |

C) Preparative LC-MS (ID

A Waters column (Waters XBridge C18, 10 μm OBD, 30×75 mm) was used. The two elution solvents were as follows: solvent A=water+0.5% of a solution of 25% NH4OH in water; solvent B=MeCN. The eluent flow rate was 75 mL/min and the characteristics of the eluting mixture proportion in function of the time t from start of the elution are summarized in the tables below (a linear gradient being used between two consecutive time points):

|  | t (min) | | | | | |
| --- | --- | --- | --- | --- | --- | --- |
|  | 0 | 0.01 | 4.0 | 6.0 | 6.2 | 6.6 |
| Solvent A (%) | 90 | 90 | 5 | 5 | 90 | 90 |
| Solvent B (%) | 10 | 10 | 95 | 95 | 10 | 10 |

Detection 210 nm.

Abbreviations (as Used Herein)

ABTS 2,2'-Azino-bis(3-ethylbenzothiazoline-6-sulfonic acid
Ac acetyl such as in AcOH=acetic acid
aq. aqueous
Bu butyl (such as in nBuLi=n-butyl lithium)
Ca circa
CC column chromatography on silica
conc. Concentrated
DCM dichloromethane
DIPEA N-ethyl diisopropyl amine
DMF dimethylformamide
DMSO dimethylsulfoxide
EA ethyl acetate
eq (molar) equivalent(s)
Et ethyl
EtOH ethanol
$Et_2O$ diethyl ether
Ex. Example
FC flash chromatography
h hour(s)
HOBt 1-hydroxybenzotriazole hydrate
HPLC high performance liquid chromatography
hv high vacuum
LC liquid chromatography
M molarity [mol $L^{-1}$]
Me methyl
MeCN acetonitrile
MeOH methanol
MS mass spectroscopy
min minute(s)

N normality
NaOH sodium hydroxide
OD optical density
o/n over night
org. organic
Pg protecting group
Ph phenyl
PTSA p-Toluenesulfonic acid
rt room temperature
sat. saturated
TBME tert-butylmethylether
TBS tert-butyldimethylsilyl
tBu tert-butyl=tertiary butyl
TEA triethylamine
Tf trifluoromethanesulfonate
TFA trifluoroacetic acid
THF tetrahydrofuran
TMS trimethylsilyl
T3P propylphosphonic anhydride
$t_R$ retention time A—Preparation of Precursors and Intermediates Preparation of Intermediates of Structure 1

The following precursors have been prepared for the synthesis of the compounds:

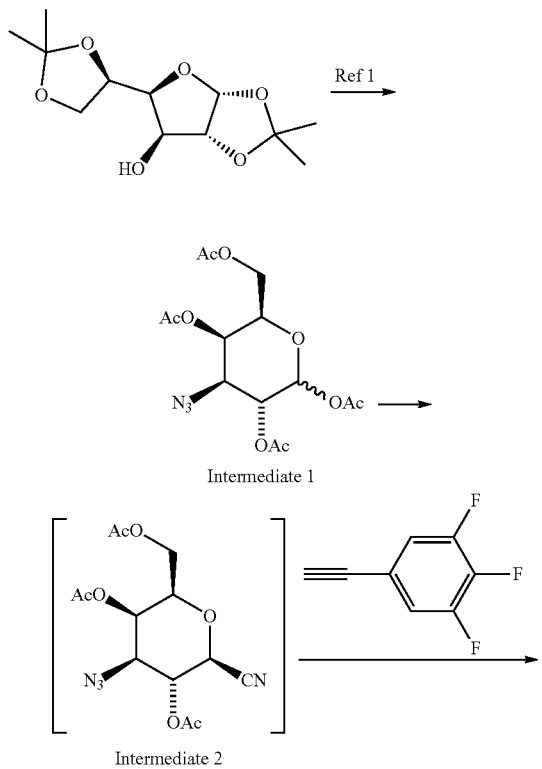

Intermediate 1

Intermediate 2

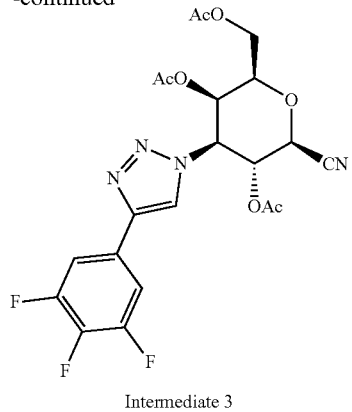

Intermediate 3

Intermediate 1: (3R,4S,5R,6R)-6-(Acetoxymethyl)-4-azidotetrahydro-2H-pyran-2,3,5-triyi triacetate (3R,4S,5R,6R)-6-(acetoxymethyl)-4-azidotetrahydro-2H-pyran-2,3,5-triyl triacetate is synthesized from (3aR,5S,6S,6aR)-5-((R)-2,2-dimethyl-1,3-dioxolan-4-yl)-2,2-dimethyltetrahydrofuro[2,3-d][1,3]dioxol-6-ol following the literature procedures from Ref: Carbohydrate Research 1994, 251, 33-67 and references cited therein.

Intermediate 2: (2R,3R,4R,5R,6S)-2-(acetoxymethyl)-6-cyano-4-(4-(3,4,5-trifluorophenyl)-1H-1,2,3-triazol-1-yl)tetrahydro-2H-pyran-3,5-diyl diacetate Intermediate 1 (10000 mg, 26.5 mmol, 1 eq) is dissolved in nitromethane (4 vol.) (40 mL) and trimethylsilyl cyanide 98% (10.2 mL, 79.6 mmol, 3 eq) and boron trifluoride diethyl etherate (3.93 mL, 31.8 mmol, 1.2 eq) are added portionwise over 30 min. Temperature is kept below 35° C. with a water bath. The mixture is stirred at rt for 2 h. The mixture is partitioned between water (400 mL), sat aq. bicarbonate (100 mL) and TBME (300 mL). The aq phase is extracted once more with TBME (200 mL) and org. phases washed twice with water/brine (ca. 5:1) and brine, dried over MgSO$_4$. TBME is evaporated on Rotavap at 20° C. The crude intermediate is purified by filtration over SiO$_2$ (150 mL cartridge filled 3/4, DCM/TBME 10:1). The intermediate is used immediately in the next step.

$^1$H NMR (500 MHz, DMSO) δ: 5.47 (dd, $J^1$=0.7 Hz, $J^2$=3.2 Hz, 1H), 5.17 (t, J=10.3 Hz, 1H), 5.04 (d, J=10.1 Hz, 1H), 4.22 (dd, $J^1$=3.2 Hz, $J^2$=10.4 Hz, 1H), 4.15 (ddd, $J^1$=0.8 Hz, $J^2$=4.5 Hz, $J^3$=7.2 Hz, 1H), 4.03-4.08 (m, 1H), 3.97 (dd, $J^1$=7.4 Hz, $J^2$=11.7 Hz, 1H), 2.18 (s, 3H), 2.15 (m, 3H), 2.04 (s, 3H)

Intermediate 3: (2R,3R,4R,5R,6S)-2-(acetoxymethyl)-6-cyano-4-(4-(3,4,5-trifluorophenyl)-1H-1,2,3-triazol-1-yl)tetrahydro-2H-pyran-3,5-diyl diacetate Intermediate 2 is dissolved in DMF (80 mL) and 5-ethynyl-1,2,3-trifluorobenzene (312 mg, 21.2 mmol, 0.8 eq), DIPEA (13.6 mL, 79.6 mmol, 3 eq) and CuI (505 mg, 2.65 mmol, 0.1 eq) are added under N$_2$. The yellow mixture is stirred at rt for 1 h. Exothermic. The yellow solution is slowly poured on water (800 mL) and stirred for 10 min. The beige precipitate is filtered off and the filtrate discarded. The beige solid is washed with MeOH and then dissolved in EA (300 mL) and stirred for 10 min. The fine Cu residues are filtered off and the filtrated is washed with NH4Cl solution (half saturated) and brine, dried over MgSO$_4$ and concentrated. The residue is triturated with MeOH (ca 100 mL), filtered and dried at hv to give the desired intermediate 3a as a beige solid $^1$H NMR (500 MHz, DMSO-d6) δ: 8.85 (s, 1H), 7.81-7.85 (m, 2H), 5.91 (m, 1H), 5.64 (dd, J1=3.1 Hz, J2=11.0 Hz, 1H), 5.51 (dd, J1=0.7 Hz, J2=3.0 Hz, 1H), 5.24 (d, J=9.9 Hz, 1H), 4.43-4.46 (m, 1H), 4.03-4.12 (m, 2H), 2.10 (s, 3H), 2.04 (m, 3H), 1.94 (m, 3H). LCMS (A): $t_R$=0.97 min; [M+H]$^+$=497.21

Intermediate 3 is further functionalised as shown in the scheme below:

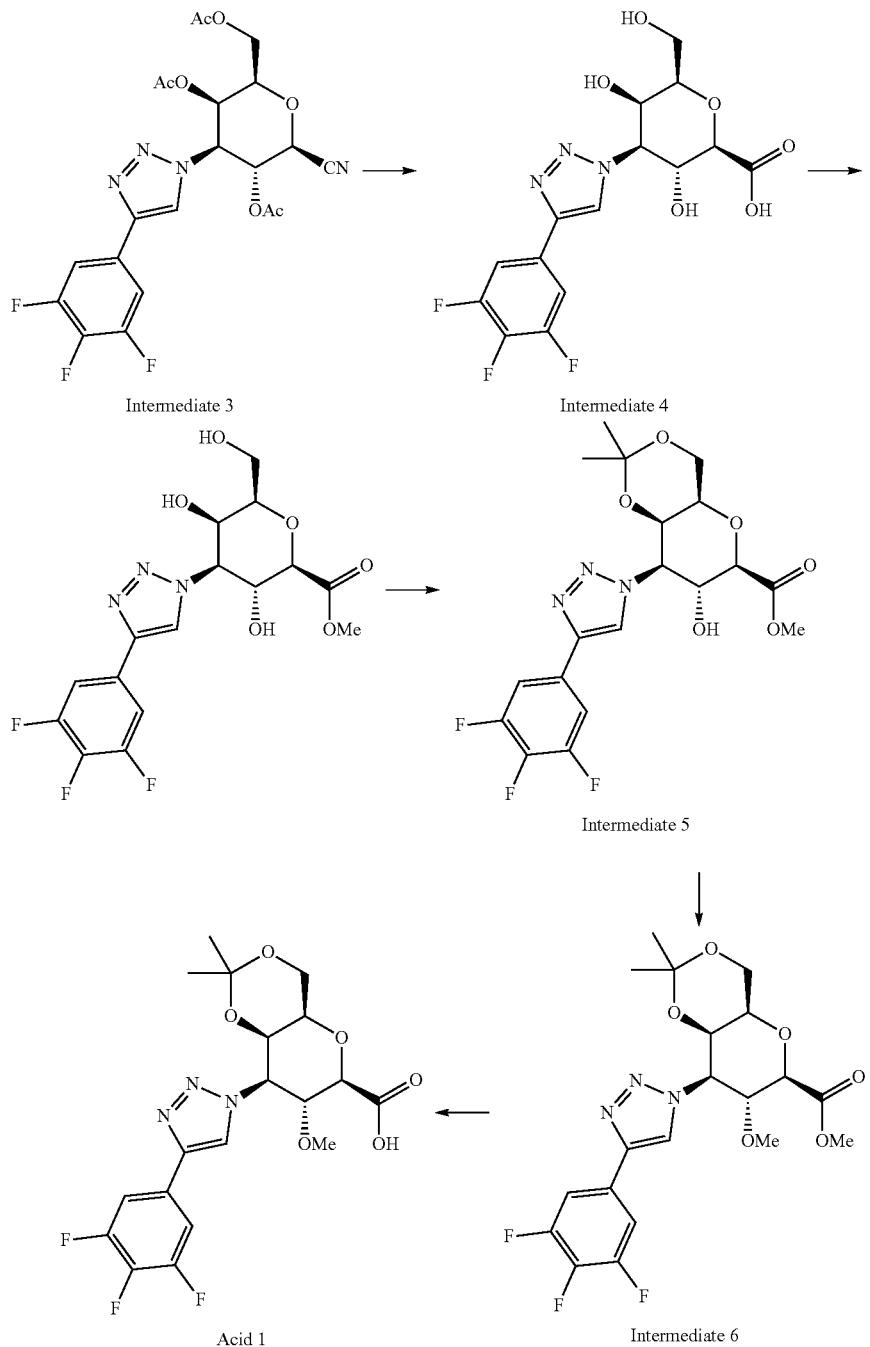

Intermediate 4: (2R,3R,4S,5R,6R)-3,5-dihydroxy-6-(hydroxymethyl)-4-(4-(3,4,5-trifluorophenyl)-1H-1,2,3-triazol-1-yl) tetrahydro-2H-pyran-2-carboxylic acid Intermediate 3 (2800 mg, 5.64 mmol, 1 eq) is suspended in HCl 25% (20.6 mL, 169 mmol, 30 eq) and heated at reflux for 1.5 h. The solution is applied to a MCI® gel column (ca 100 mL gel) under water. The column is eluted with water until neutral pH (5 fractions a 40 mL). The compound is then eluted with $H_2O$/MeCN (3:1). Fractions of 40 mL are taken. Fractions containing product are first concentrated in vacuo to remove MeCN and then freeze-dried to give the title compound as a colourless solid.

LCMS (A): $t_R$=0.59 min; $[M+H]^+$=390.22

$^1$H NMR (500 MHz, DMSO-d6) δ: 12.88-12.90 (br, 1H), 8.79 (s, 1H), 7.86 (dd, $J^1$=6.8 Hz, $J^2$=9.1 Hz, 2H), 5.43-5.46 (m, 1H), 5.30 (d, J=6.2 Hz, 1H), 4.84 (dd, $J^1$=3.0 Hz, $J^2$=10.8 Hz, 1H), 4.72 (d, J=0.5 Hz, 1H), 4.36 (t, J=10.0 Hz, 1H), 3.94 (dd, $J^1$=3.0 Hz, $J^2$=6.0 Hz, 1H), 3.85 (d, J=9.4 Hz, 1H), 3.71 (t, J=6.5 Hz, 1H), 3.48-3.55 (m, 2H)

Intermediate 5: Methyl (4aR,6R,7R,8R,8aR)-7-hydroxy-2,2-dimethyl-8-(4-(3,4,5-trifluorophenyl)-1H-1,2,3-triazol-1-yl)hexahydropyrano[3,2-d][1,3]dioxine-6-carboxylate Step 1: Methyl (2R,3R,4S, 5R, 6R)-3,5-dihydroxy-6-(hydroxymethyl)-4-(4-(3,4,5-trifluorophenyl)-1H-1,2,3-triazol-1-yl) tetrahydro-2H-pyran-2-carboxylate To a suspension of Intermediate 4 (14.2 g, 0.036 mol) in MeOH (60 ml) and THF (40 ml) is added 1M $H_2SO_4$ in MeOH (1.82 ml, 0.00182 mol) [freshly prepared by dissolving $H_2SO_4$ 95-98% (0.136 ml) in 2.5 ml MeOH]. The mixture is stirred at rt over the weekend. $K_2CO_3$ (0.25 g, 0.0018 mol) is added, the mixture is filtered, and the solvent is evaporated in vacuo. The crude intermediate is purified by filtration over $SiO_2$ (EA/MeOH 9:1). The crude product—a colourless solid—is used in the next step without purification.

LCMS (A): $t_R$=0.85 min; $[M+H]^+$=403.87

Step 2: Methyl (4aR,6R,7R,8R,8aR)-7-hydroxy-2,2-dimethyl-8-(4-(3,4,5-trifluorophenyl)-1H-1,2,3-triazol-1-yl)hexa-hydropyrano[3,2-d][1,3]dioxine-6-carboxylate To a mixture of crude product from step 1 (15.5 g, 0.038 mmol) in THF (400 ml) and 2,2-dimethoxypropane (7.22 ml, 0.058 mmol) is added at rt PTSA (0.165 g, 0.001 mol). The reaction mixture is stirred at 75° C. for 1.5 h, during which time ca. 150 ml of the solvent are distilled off the mixture. The mixture is allowed cool down to rt and is partitioned between aq. sat $NaHCO_3$ and EA. The aq. layer is once more extracted with EA. The combined org. layers are washed with water and brine, dried with $MgSO_4$, filtered and evaporated in vacuo. The crude product—a yellowish solid—is used in the next step without purification.

LCMS (A): $t_R$=0.88 min; $[M+H]^+$=444.01

Intermediate 6: Methyl (4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxine-6-carboxylate To solution of Intermediate 5 (16.5 g, 0.037 mol) in DMF (180 ml) is added at 0° C. iodomethane (2.57 ml, 0.041 mol) followed by addition of NaH (60% dispersion in mineral oil, 1.57 g, 0.041 mol). The mixture is allowed to warm to rt and stirred at rt for 4 h. The mixture is cooled to 0° C., carefully quenched by addition of water and extracted twice with EA. The combined org. layers are washed with water and brine, dried with $MgSO_4$, filtered and evaporated in vacuo. The crude product is purified by column chromatography (6 cm×24 cm $SiO_2$ column; gradient: heptane/EA 2:1 to heptane/EA 1:1) to give the desired product as a yellowish solid.

LCMS (A): $t_R$=0.98 min; $[M+H]^+$=458.03

Acid 1: (4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxine-6-carboxylic acid A mixture of Intermediate 6 (12.8 g, 0.028 mol) in THF/MeOH/$H_2O$ (3.2:1, 90 ml) and LiOH.$H_2O$ (1.77 g, 0.042 mmol) is stirred at rt for 2 h. The mixture is diluted by water (100 ml) and THF/MeOH are evaporated. Additional water (100 ml) and citric acid (10% in water) is added to reach pH 3. The suspension is filtered, the solid is washed with water and the crude product—a colourless solid—is dried under hv.

LCMS (A): $t_R$=0.87 min; $[M+H]^+$=444.03

Acids 2-6 are synthesized in analogy to the Acid 1 using the corresponding acetylene for the cycloaddition with Intermediate 2.

| Acid | Compound | $t_R$ [min] LC-MS A | MS Data m/z $[M + H]^+$ |
|---|---|---|---|
| 2 | (4aR,6R,7R,8R,8aR)-8-(4-(4-bromo-2,3-difluorophenyl)-1H-1,2,3-triazol-1-yl)-7-methoxy-2,2-dimethylhexahydropyrano[3,2-d][1,3]dioxine-6-carboxylic acid | 0.89 | 505.92 |
| 3 | (4aR,6R,7R,8R,8aR)-8-(4-(3,5-difluoro-4-methylphenyl)-1H-1,2,3-triazol-1-yl)-7-methoxy-2,2-dimethylhexahydropyrano[3,2-d][1,3]dioxine-6-carboxylic acid | 0.88 | 440.08 |
| 4 | (4aR,6R,7R,8R,8aR)-8-(4-(2,3-difluoro-4-methylphenyl)-1H-1,2,3-triazol-1-yl)-7-methoxy-2,2-dimethylhexahydropyrano[3,2-d][1,3]dioxine-6-carboxylic acid | 0.87 | 440.12 |
| 5 | (4aR,6R,7R,8R,8aR)-8-(4-(4-chloro-3,5-difluorophenyl)-1H-1,2,3-triazol-1-yl)-7-methoxy-2,2-dimethylhexahydropyrano[3,2-d][1,3]dioxine-6-carboxylic acid | 0.90 | 460.01 |
| 6 | (4aR,6R,7R,8R,8aR)-8-(4-(3,4-dichlorophenyl)-1H-1,2,3-triazol-1-yl)-7-methoxy-2,2-dimethylhexahydropyrano[3,2-d][1,3]dioxine-6-carboxylic acid | 0.90 | 457.98 |

Preparation of Intermediates of Structure 2

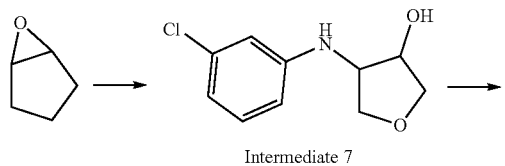

Intermediate 7

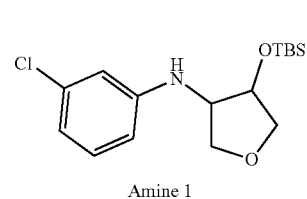

Amine 1

Intermediate 7:
4-((3-chlorophenyl)amino)tetrahydrofuran-3-ol

Step 1: To a solution of 3,6-dioxabicyclo[3.1.0]hexane (400 mg, 4.55 mmol) and 3-chloroaniline (639 mg, 5.01 mmol) in toluene (4 ml) is added $InCl_3$ (71 mg, 0.32 mmol) and the reaction mixture is stirred at 85° for 3 days. Water and EA are added at rt and the mixture is stirred for 30 min at rt. The water phase is separated and extracted with EA. The combined org. layers are dried with $MgSO_4$, filtered and evaporated in vacuo. The crude product is purified by prep. LC-MS MS (II) to give the title intermediate 7 as a yellow oil.

LCMS (A): $t_R$=0.72 min; $[M+H]^+$=214.06

Amine 1: 4-((tert-butyldimethylsilyl)oxy)-N-(3-chlorophenyl)tetrahydrofuran-3-amine Step 2: To a solution of Intermediate 7 (250 mg, 1.41 mmol) and 2,6-lutidine (333 mg, 3.1 mmol) in DCM (10 ml) is added at 0° C. tert-butyldimethylsilyl trifluoromethanesulfonate (447 mg, 1.69 mmol) and the mixture is stirred at 0° C. for 1 h. Water is added, the mixture is quenched with sat. aq. $NH_4Cl$ solution and extracted twice with DCM. The org. layers are washed with brine. The combined org. layers are dried over $MgSO_4$, filtered and concentrated.

The crude is purified by FC CombiFlash (24 g RediSep column, 0-30% EA in heptane within 10 min) to give the amine 1 as a colourless oil. LCMS (A): $t_R$=1.21 min; $[M+H]^+$=328.05

The following amines 2-11 are prepared in analogy to Amine 1 in 2 steps by coupling of the corresponding aniline with 3,6-dioxabicyclo[3.1.0]hexane.

| Amine | Compound | $t_R$ [min] LC-MS A | MS Data m/z $[M + H]^+$ |
|---|---|---|---|
| 2 | N-(3-bromophenyl)-4-((tert-butyldimethylsilyl)oxy)tetrahydrofuran-3-amine | 1.22 | 371.97 |
| 3 | 4-((tert-butyldimethylsilyl)oxy)-N-(3-iodophenyl)tetrahydrofuran-3-amine | 1.23 | 419.86 |
| 4 | 4-((tert-butyldimethylsilyl)oxy)-N-(3,5-dichlorophenyl)tetrahydrofuran-3-amine | 1.26 | 361.97 |
| 5 | 3-((4-((tert-butyldimethylsilyl)oxy)tetrahydrofuran-3-yl)amino)-5-chlorobenzonitrile | 1.21 | 352.97 |
| 6 | 4-((tert-butyldimethylsilyl)oxy)-N-(3,5-dibromophenyl)tetrahydrofuran-3-amine | 1.28 | 451.89 |
| 7 | 3-bromo-5-((4-((tert-butyldimethylsilyl)oxy)tetrahydrofuran-3-yl)amino)benzonitrile | 1.22 | 398.96 |
| 8 | N-(3-bromo-5-methylphenyl)-4-((tert-butyldimethylsilyl)oxy)tetrahydrofuran-3-amine | 1.25 | 385.82 |
| 9 | 3-((4-((tert-butyldimethylsilyl)oxy)tetrahydrofuran-3-yl)amino)-5-methoxybenzonitrile | 1.16 | 349.07 |
| 10 | 3-((4-((tert-butyldimethylsilyl)oxy)tetrahydrofuran-3-yl)amino)-5-methylbenzonitrile | 1.19 | 333.11 |
| 11 | 3-((4-((tert-butyldimethylsilyl)oxy)tetrahydrofuran-3-yl)amino)-5-fluorobenzonitrile | 1.17 | 337.05 |

The following amines 12 and 13 are prepared in analogy to Amine 1 in 2 steps by coupling of the corresponding aniline with tert-butyl 6-oxa-3-azabicyclo[3.1.0]hexane-3-carboxylate. The enantiomers are separated by chiral chromatography before silylated and used for the amide coupling.

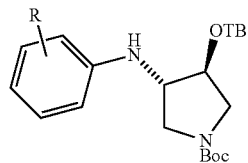

| Amine | Compound | $t_R$ [min] LC-MS A | MS Data m/z [M + H]$^+$ |
|---|---|---|---|
| 12* | tert-butyl (3S,4S)-3-((tert-butyldimethylsilyl)oxy)-4-((3,5-dichlorophenyl)amino)pyrrolidine-1-carboxylate | 1.32 | 461.08 |
| 13* | tert-butyl (3S,4S)-3-((3-bromo-5-methylphenyl)amino)-4-((tert-butyldimethyl-silyl)oxy)pyrrolidine-1-carboxylate | 1.30 | 486.90 |

*could contain the tert-butyldimethylsilyl (3S,4S)-3-((tert-butyldimethylsilyl)oxy)-4-((3,5-dichlorophenyl)amino)pyrrolidine-1-carboxylate as a side product of the protection of hydroxy group with TBSCl The following amines 14-17 are prepared in analogy to Amine 1 in 2 steps by coupling of the corresponding aniline with 1-(6-oxa-3-azabicyclo[3.1.0]hexan-3-ypethan-1-one. Enantiomers of 16 are separated by chiral chromatography before silylated and used for the amide coupling, amines 14, 15 and 17 are used as racemate for the amide coupling.

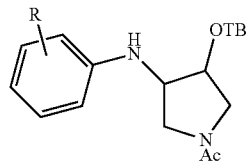

| Amine | Compound | $t_R$ [min] LC-MS A | MS Data m/z [M + H]$^+$ |
|---|---|---|---|
| 14 | 1-(3-((tert-butyldimethylsilyl)oxy)-4-((3,5-dichlorophenyl)amino)pyrrolidin-1-yl)ethan-1-one | 1.22 | 402.90 |
| 15 | 1-(3-((tert-butyldimethylsilyl)oxy)-4-((3,5-dibromophenyl)amino)pyrrolidin-1-yl)ethan-1-one | 1.23 | 492.77 |
| 16 | 3-(((3S,4S)-1-acetyl-4-((tert-butyldimethylsilyl)oxy)pyrrolidin-3-yl)amino)-5-bromobenzonitrile | 1.17 | 439.93 |
| 17 | 1-(3-((3-bromo-5-methylphenyl)amino)-4-((tert-butyldimethylsilyl)oxy)pyrrolidin-1-yl)ethan-1-one | 1.22 | 428.92 |

The following amines 18-21 are prepared in analogy to Amine 1 in 2 steps by coupling of the corresponding aniline with 3,7-dioxabicyclo[4.1.0]heptane. In these cases, the obtained aminoalcohols are separated by chiral chromatography before silylated and used for the amide coupling.

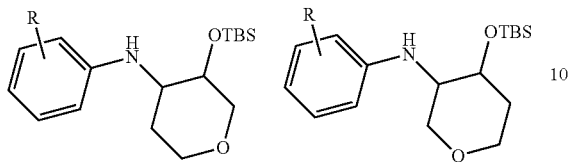

| Amine | Compound | $t_R$ [min] LC-MS A | MS Data m/z [M + H]$^+$ |
|---|---|---|---|
| 18 | (3R,4S)-3-((tert-butyldimethylsilyl)oxy)-N-(3,5-dichlorophenyl)tetrahydro-2H-pyran-4-amine | 0.85 | 262.04 |
| 19 | (3S,4R)-3-((tert-butyldimethylsilyl)oxy)-N-(3,5-dichlorophenyl)tetrahydro-2H-pyran-4-amine | 0.85 | 262.04 |
| 20 | (3S,4S)-4-((tert-butyldimethylsilyl)oxy)-N-(3,5-dichlorophenyl)tetrahydro-2H-pyran-3-amine | 0.84 | 262.04 |
| 21 | (3R,4R)-4-((tert-butyldimethylsilyl)oxy)-N-(3,5-dichlorophenyl)tetrahydro-2H-pyran-3-amine | 0.84 | 262.04 |

The following amines 22-25 are prepared in analogy to Amine 1 in 2 steps by coupling of the corresponding aniline with tert-butyl 7-oxa-3-azabicyclo[4.1.0]heptane-3-carboxylate. In these cases, the obtained aminoalcohols are separated by chiral chromatography before silylated and used for the amide coupling.

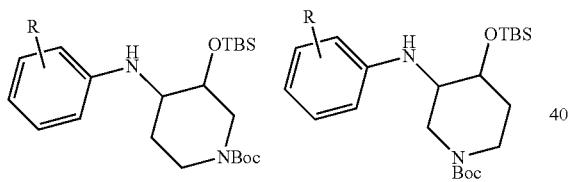

| Amine | Compound | $t_R$ [min] LC-MS A | MS Data m/z [M + H]$^+$ |
|---|---|---|---|
| 22 | tert-butyl (3S,4S)-3-((tert-butyldimethylsilyl)oxy)-4-((3,5-dichlorophenyl) amino)piperidine-1-carboxylate | 1.03 | 360.93 |
| 23 | tert-butyl (3R,4R)-3-((tert-butyldimethylsilyl)oxy)-4-((3,5-dichlorophenyl)amino)piperidine-1-carboxylate | 1.03 | 360.95 |
| 24 | tert-butyl (3S,4S)-4-((tert-butyldimethylsilyl)oxy)-3-((3,5-dichlorophenyl)amino)piperidine-1-carboxylate | 1.01 | 360.95 |
| 25 | tert-butyl (3R,4R)-4-((tert-butyldimethylsilyl)oxy)-3-((3,5-dichlorophenyl)amino)piperidine-1-carboxylate | 1.01 | 360.94 |

B—PREPARATION OF EXAMPLES

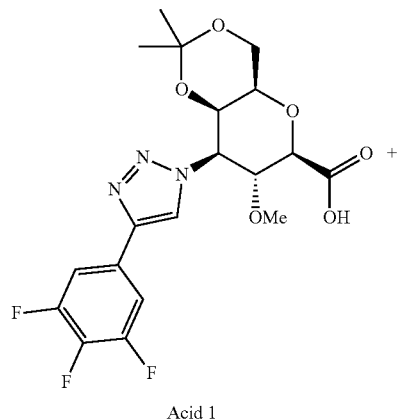

Acid 1

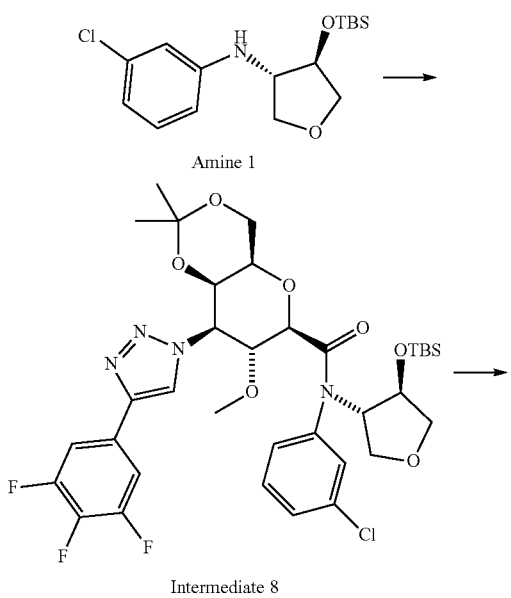

Amine 1

Intermediate 8

Example 1: (2R,3R,4S,5R,6R)—N-(3-chlorophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide

Step 1: (4aR,6R,7R,8R,8aR)—N-((3S,4R)-4-((tert-butyldimethylsilyl)oxy)tetrahydrofuran-3-yl)-N-(3-chlorophenyl)-7-methoxy-2,2-dimethyl-8-(4-(3,4,5-trifluorophenyl)-1H-1,2,3-triazol-1-yl)hexahydropyrano[3,2-d][1,3]dioxine-6-carboxamide To a mixture of Acid 1 (50 mg; 0.113 mmol) and Amine 1 (39 mg, 0.118 mmol) in DCM (4 mL) is added at rt phosphorus(V) oxychloride (1M solution in pyridine, 0.14 mL, 0.135 mmol) and the mixture is stirred at rt for 24 h. Water is added, the mixture is quenched with sat. aq. NH₄Cl solution and extracted twice with DCM. The org. layers are washed with brine. The combined org. layers are dried over MgSO₄, filtered and concentrated. The crude is purified by prep. LC-MS (I) to give the Intermediate 8 (as a mixture of diastereomers).

LCMS (A): $t_R$=1.29/1.30 min; [M+H]⁺=753.10

Step 2: (2R,3R,4S,5R,6R)—N-(3-chlorophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-Atetrahydro-2H-pyran-2-carboxamide To a solution of intermediate 8 (mixture of diastereomers) (74 mg, 0.98 mmol) in dioxane (1 ml) and water (0.5 ml) is added at 0° C. TFA (0.60 ml, 7.8 mmol) and the reaction mixture is stirred at rt for 21 h. The solvent is evaporated, MeCN is added, mixture is basified with 25% aq. NH₄OH solution (to rich pH 11) and the product is purified by prep. LCMS (II) to give the final compound as a mixture of diastereomers, which are separated by chiral column chromatography to give example 1 and example 30.

Example 1: ¹H NMR (500 MHz, DMSO) δ: 9.00 (s, 1H), 7.88 (dd, J₁=9.0 Hz, J₂=6.8 Hz, 2H), 7.57 (m, 1H), 7.49-7.52 (m, 1H), 7.46 (s, 1H), 7.35-7.39 (m, 1H), 5.39 (d, J=4.9 Hz, 1H), 5.33 (d, J=6.0 Hz, 1H), 4.83 (d, J=9.2 Hz, 1H), 4.63-4.72 (m, 2H), 4.39 (dd, J₁=9.1 Hz, J₂=10.6 Hz, 1H), 4.24 (m, 1H), 4.03 (dd, J₁=7.1 Hz, J₂=9.5 Hz, 1H), 3.76 (m, 1H), 3.64 (m, 2H), 3.50 (d, J=9.0 Hz, 1H), 3.38-3.46 (m, 3H), 3.17 (t, J=6.4 Hz, 1H), 3.07 (s, 3H)

LC-MS (A): $t_R$=0.85 min; [M+H]⁺=599.05

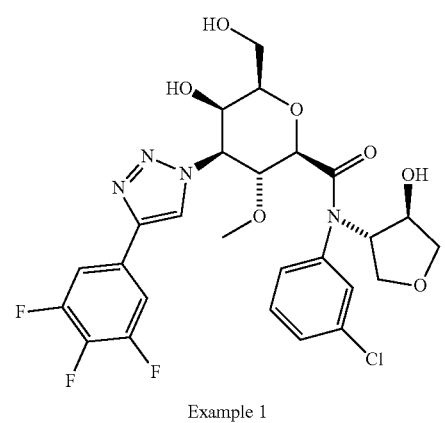

Example 1

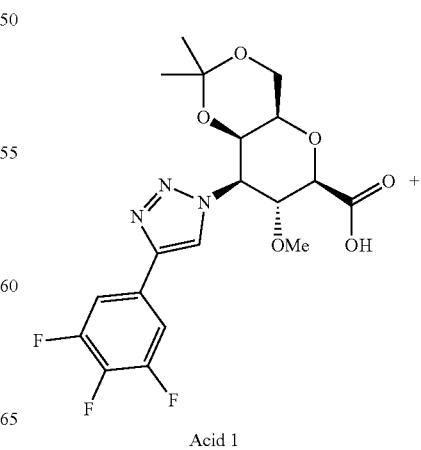

Acid 1

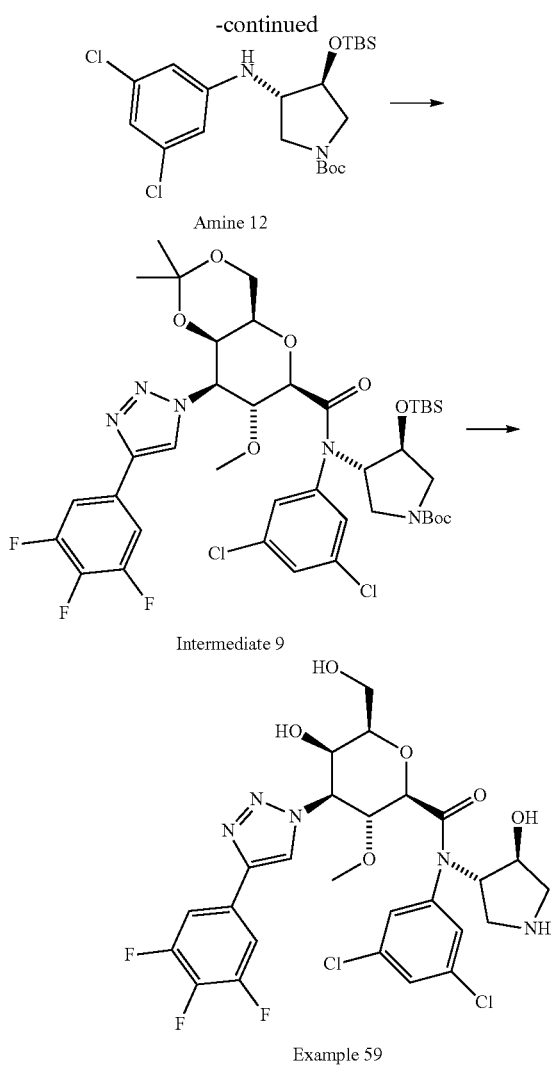

Example 59: (2R,3R,4S,5R,6R)—N-(3,5-dichlorophenyl)-5-hydroxy-6-(hydroxymethyl)-N-((3S,4S)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide Step 1: tert-butyl (3S,4S)-3-((tert-butyldimethylsilyl)oxy)-4-((4aR,6R,7R,8R, 8aR)—N-(3,5-dichlorophenyl)-7-methoxy-2,2-dimethyl-8-(4-(3,4,5-trifluorophenyl)-1H-1,2,3-triazol-1-yl)hexahydropyrano[3,2-d][1,3]dioxine-6-carboxamido)pyrrolidine-1-carboxylate To a mixture of Acid 1 (450 mg; 1.01 mmol) and Amine 12 (554 mg, 1.07 mmol) in DCM (35 mL) is added at rt phosphorus(V) oxychloride (1M solution in pyridine, 1.22 mL, 1.22 mmol) and the mixture is stirred at rt for 24 h. Water is added, the mixture is quenched with sat. aq. NH$_4$Cl solution and extracted twice with DCM. The org. layers are washed with brine. The combined org. layers are dried over MgSO$_4$, filtered and concentrated. The crude is purified by ISCO (24 g RediSep column, 0-80% EA in heptane within 15 min) to give the intermediate 9 as yellow foam.

LCMS (A): $t_R$=1.37 min; [M+H]$^+$=886.09

The product may contain tert-butyldimethylsilyl (3S,4S)-3-((tert-butyldimethylsilyl)oxy)-4-((4aR,6R,7R,8R,8aR)—N-(3,5-dichlorophenyl)-7-methoxy-2,2-dimethyl-8-(4-(3,4,5-trifluorophenyl)-1H-1,2,3-triazol-1-yl)hexahydropyrano[3,2-d][1,3]dioxine-6-carboxamido)pyrrolidine-1-carboxylate.

LCMS (A): $t_R$=1.42 min; [M+H]$^+$=944.10

Step 2: (2R,3R,4S,5R,6R)—N-(3,5-dichlorophenyl)-5-hydroxy-6-(hydroxymethyl)-N-((3S,4S)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide To a solution of intermediate 9 (486 mg, 0.51 mmol) in dioxane (10 ml) and water (5 ml) is added at 0° C. TFA (1.97 ml, 25.7 mmol) and the reaction mixture is stirred at rt for 2 weeks [additional TFA (0.5 ml) is added after 3 days and one week]. EA is added, mixture is basified with 25% aq. NH$_4$OH solution (to rich pH 9) and extracted twice with EA. The org. layers are washed with brine. The combined org. layers are dried over MgSO$_4$, filtered and concentrated. The crude is purified by ISCO (12 g RediSep column, 0-30% 7N NH$_3$/MeOH in DCM) and prep. LC-MS (II) to give the final product as a colourless solid.

LCMS (A): $t_R$=0.71 min; [M+H]$^+$=631.96

Example 59: $^1$H NMR (500 MHz, DMSO) δ: 9.01 (s, 1H), 7.89 (dd, J$_1$=9.0 Hz, J$_2$=6.8 Hz, 2H), 7.76 (t, J=1.8 Hz, 1H), 7.48 (s, 2H), 5.34 (d, J=6.0 Hz, 1H), 5.11 (d, J=5.1 Hz, 1H), 4.92 (dd, J$_1$=10.7 Hz, J$_2$=2.9 Hz, 1H), 4.70 (m, 1H), 4.40 (dd, J$_1$=9.0 Hz, J$_2$=10.7 Hz, 1H), 4.33 (m, 1H), 4.01 (m, 1H), 3.79 (dd, J$_1$=6.0 Hz, J$_2$=2.8 Hz, 1H), 3.59 (d, J=9.0 Hz, 1H), 3.40-3.56 (m, 2H), 3.31 (m, 2H), 3.16 (dd, J$_1$=8.3 Hz, J$_2$=11.3 Hz, 1H), 3.00-3.07 (m, 3H), 2.87 (dd, J$_1$=6.6 Hz, J$_2$=11.2 Hz, 1H), 2.80 (dd, J$_1$=7.4 Hz, J$_2$=11.4 Hz, 1H)

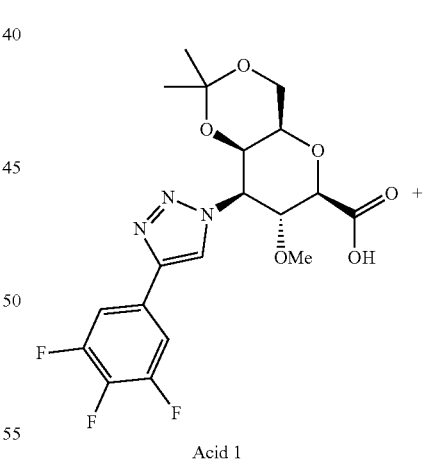

Acid 1

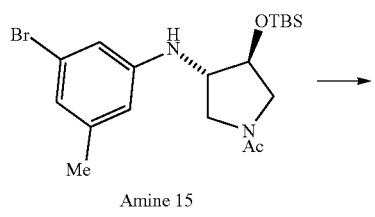

Amine 15

-continued

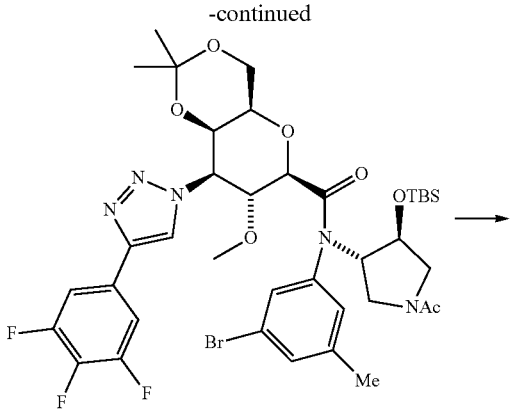

Intermediate 10

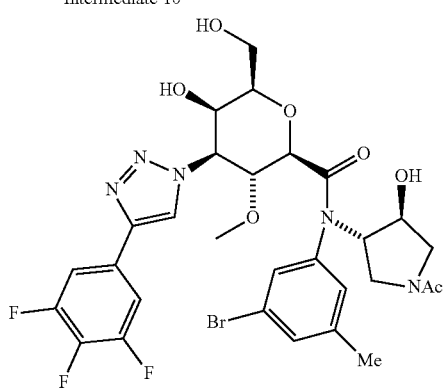

Example 72
or

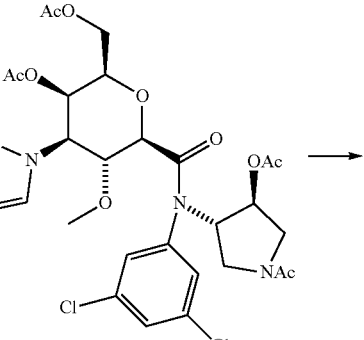

Example 59

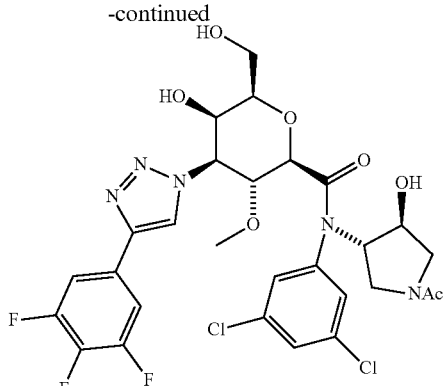

Intermediate 11

-continued

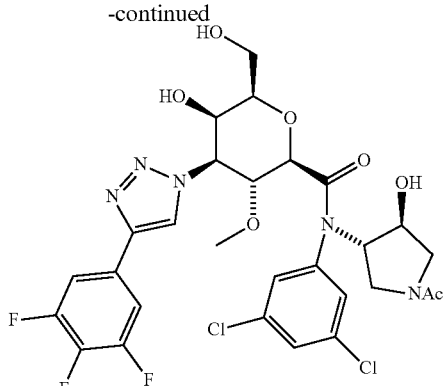

Example 71

Example 72: (2R,3R,4S,5R,6R)—N-((3S,4S)-1-acetyl-4-hydroxypyrrolidin-3-yl)-N-(3-bromo-5-methylphenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide This product is prepared in 2 steps in analogy to example 1 from the acid 1 and amine 15. The diastereomers are separated by chiral chromatography to give example 72 and 79.

LCMS (A): $t_R$=0.84 min; [M+H]$^+$=697.91

Example 72: 100° C.: $^1$H NMR (400 MHz, DMSO) δ: 8.82 (m, 1H), 7.77-7.83 (m, 2H), 7.49-7.51 (m, 1H), 7.31-7.42 (m, 1H), 7.17-7.28 (m, 1H), 5.17-5.29 (m, 1H), 4.96-5.02 (m, 1H), 4.64-4.82 (m, 2H), 4.42-4.49 (m, 1H), 4.33-4.42 (m, 1H), 4.13-4.29 (m, 1H), 3.84-3.93 (m, 1H+0.5H), 3.70-3.75 (m, 0.5H), 3.33-3.65 (m, 5H), 3.16-3.33 (m, 1H), 3.09 (s, 3H), 2.97 (m, 1H), 2.39 (s, 3H), 1.83 (s, 3H)

The N-acetyl analogs could be prepare also in 2 steps procedure—peracetylation and O-deacetylation from the corresponding NH products as shown for example 71.

Example 71: (2R,3R,4S,5R,6R)—N-((3S,4S)-1-acetyl-4-hydroxypyrrolidin-3-yl)-N-(3,5-dichlorophenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide Step 1: (2R,3R,4R,5R,6R)-6-(((3S,4S)-4-acetoxy-1-acetylpyrrolidin-3-yl)(3,5-dichlorophenyl)carbamoyl)-2-(acetoxymethyl)-5-methoxy-4-(4-(3,4,5-ttifluorophenyl)-1H-1,2,3-triazol-1-yl)tetrahydro-2H-pyran-3-yl acetate To a solution of compound 59 (23 mg, 0.0364 mmol) in DCM (1.5 ml) is added at rt triethylamine (0.050 ml, 0.364 mmol), acetic acid anhydride (0.017 ml, 0.182 mmol) and DMAP (6.7 mg, 0.054 mmol) and the mixture is stirred at rt for 15 min. The mixture is quenched with sat. aq. NH$_4$Cl solution and extracted twice with DCM. The org. layers are washed with brine. The combined org. layers are dried over MgSO$_4$, filtered and concentrated. The intermediate 11 is used in the next step without purification.

LCMS (A): $t_R$=1.07 min; [M+H]$^+$=800.03

Step 2: (2R,3R,4S,5R,6R)—N-((3S,4S)-1-acetyl-4-hydroxypyrrolidin-3-yl)-N-(3,5-dichlorophenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide To a solution of intermediate 11 (27 mg, 0.0337 mmol) in MeOH (1.5 ml) is added a solution of NaOMe in MeOH (1.26 ml; selfmade by dissolving 0.25 mg NaOMe in 1 ml MeOH) at rt and the mixture is stirred for 3 h. The mixture is quenched with sat. aq. NH$_4$Cl solution and extracted twice with ethyl acetate. The org. layers are washed with brine. The combined org. layers are dried over MgSO$_4$, filtered and concentrated. The crude is purified by prep. LC-MS (II) to give the final product as a colourless solid LCMS (A): $t_R$=0.85 min; [M+H]$^+$=673.86.

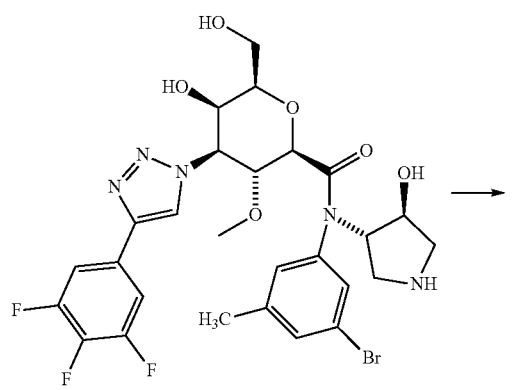

Example 61

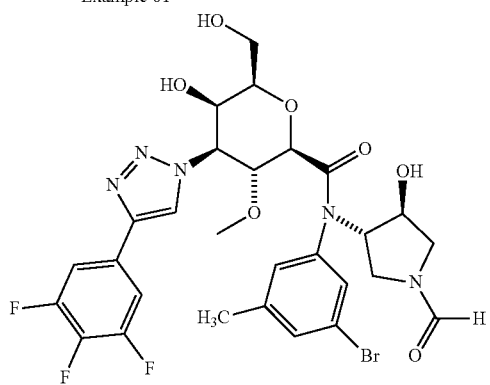

Example 90

Example 90: (2R,3R,4S,5R,6R)—N-(3-bromo-5-methylphenyl)-N-((3S,4S)-1-formyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide To a solution of the example 61 (35 mg, 0.053 mmol) in ethyl formate (0.44 ml, 5.33 mmol) is added triethylamine (0.008 ml, 0.053 mmol) and the reaction mixture is stirred at 50° C. for 4 h in sealed tube. The solvent is evaporated and the mixture is purified by prep. LC-MS (II) to give the final product as a colourless solid.

LCMS (A): $t_R$=0.84 min; [M+H]$^+$=683.83

Example 90: 100° C. $^1$H NMR (400 MHz, DMSO) δ: 8.82 (s, 1H), 8.00 (brs, 1H), 7.78-7.82 (m, 2H), 7.50 (s, 1H), 7.37 (m, 1H), 7.23 (s, 1H), 5.22-5.37 (m, 1H), 4.97-5.03 (m, 1H), 4.74-4.79 (m, 1H), 4.59-4.65 (m, 1H), 4.45 (m, 1H), 4.34-4.41 (m, 1H), 4.18-4.28 (m, 1H), 3.50-4.0 (m, 6H), 3.34-3.49 (m, 1H), 3.19-3.32 (m, 1H), 3.09 (s, 3H), 3.01-3.05 (m, 1H), 2.39 (s, 3H)

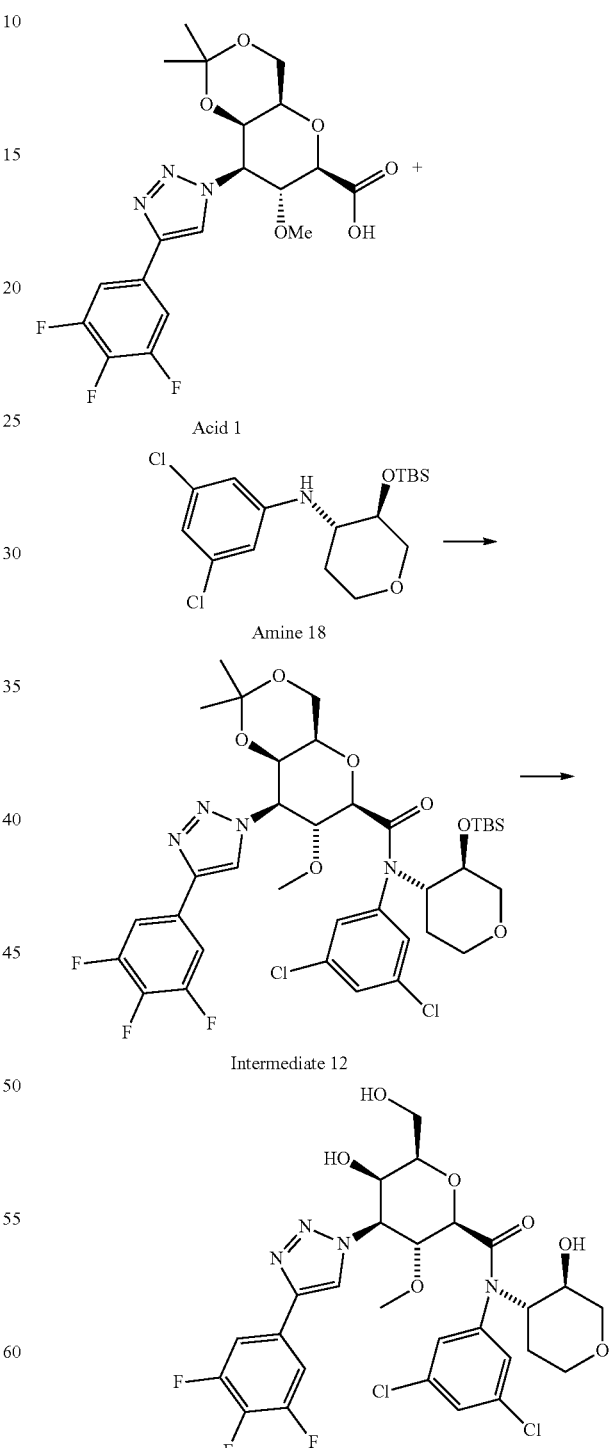

Example 99: (2R,3R,4S,5R,6R)—N-(3,5-dichlorophenyl)-5-hydroxy-6-(hydroxymethyl)-N-((3R,4S)-3-hydroxytetrahydro-2H-pyran-4-yl)-3-methoxy-4-(4-(3,4,5-trifluorophenyl)-1H-1,2,3-triazol-1-yl)tetrahydro-2H-pyran-2-carboxamide This product is prepared in 2 steps in analogy to example 1 from the acid 1 and amine 18.

LCMS (A): $t_R$=0.93 min; [M+H]$^+$=646.97

Example 99: $^1$H NMR (500 MHz, DMSO) δ: 9.00 (s, 1H), 7.89 (dd, $J_1$=6.8 Hz, $J_2$=9.1 Hz, 2H), 7.78 (t, J=1.9 Hz, 1H), 7.55 (s, 1H), 7.38 (s, 1H), 5.33 (d, J=6.0 Hz, 1H), 5.10 (d, J=5.7 Hz, 1H), 4.90 (dd, $J_1$=10.8 Hz, $J_2$=2.9 Hz, 1H), 4.68 (t, J=5.6 Hz, 1H), 4.31-4.41 (m, 2H), 3.76-3.81 (m, 4H), 3.55 (d, J=9.0 Hz, 1H), 3.45 (t, J=6.1 Hz, 2H), 3.31-3.36 (m, 1H), 3.28 (t, J=6.7 Hz, 1H), 3.21 (m, 1H), 3.07 (s, 3H), 1.71-1.84 (m, 2H)

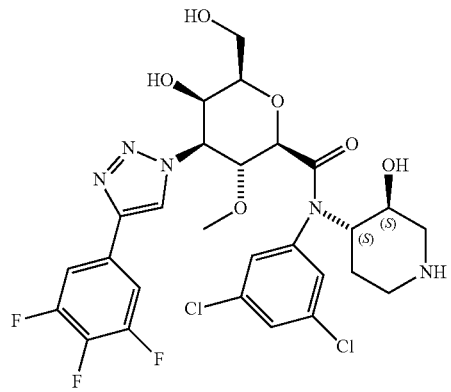

Example 109

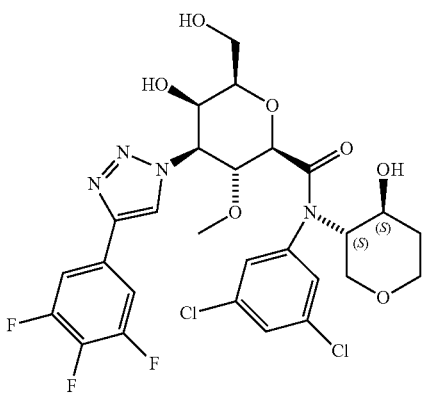

Example 105

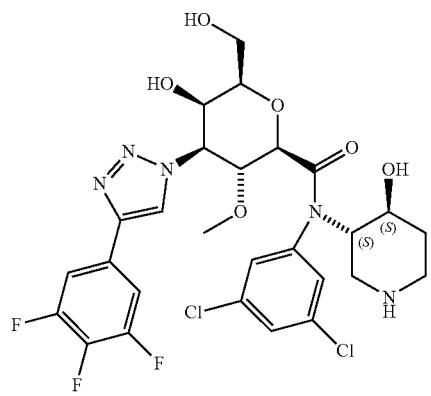

Example 113

Example 105: (2R,3R,4S,5R,6R)—N-(3,5-dichlorophenyl)-5-hydroxy-6-(hydroxymethyl)-N-((3S,4S)-4-hydroxytetrahydro-2H-pyran-3-yl)-3-methoxy-4-(4-(3,4,5-trifluorophenyl)-1H-1,2,3-triazol-1-yl)tetrahydro-2H-pyran-2-carboxamide This product is prepared in 2 steps in analogy to example 1 from the acid 1 and amine 20.

LCMS (A): $t_R$=0.93 min; [M+H]$^+$=647.00

Example 105: $^1$H NMR (500 MHz, DMSO) δ: 9.00 (s, 1H), 7.89 (dd, $J_1$=6.8 Hz, $J_2$=9.1 Hz, 2H), 7.76 (m, 1H), 7.59 (s, 1H), 7.31-7.39 (m, 1H), 5.32 (d, J=6.0 Hz, 1H), 5.04 (d, =5.8 Hz, 1H), 4.89 (dd, $J_1$=10.8 Hz, $J_2$=2.9 Hz, 1H), 4.68 (t, J=5.6 Hz, 1H), 4.39 (dd, $J_1$=10.7 Hz, $J_2$=9.0 Hz, 1H), 4.23 (td, $J_1$=10.4 Hz, $J_2$=4.4 Hz, 1H), 3.85 (dd, $J_1$=4.7 Hz, $J_2$=11.0 Hz, 1H), 3.74-3.79 (m, 2H), 3.53 (d, J=9.0 Hz, 1H), 3.45 (t, J=6.0 Hz, 2H), 3.32-3.36 (m, 1H), 3.25-3.30 (m, 2H), 3.20 (td, $J_1$=1.4 Hz, $J_2$=12.1 Hz, 1H), 3.07 (s, 3H), 1.84-1.87 (m, 1H), 1.42-1.61 (m, 1H)

Example 109: (2R,3R,4S,5R,6R)—N-(3,5-dichlorophenyl)-5-hydroxy-6-(hydroxymethyl)-N-((3S,4S)-3-hydroxypiperidin-4-yl)-3-methoxy-4-(4-(3,4,5-trifluorophenyl)-1H-1,2,3-triazol-1-yl)tetrahydro-2H-pyran-2-carboxamide This product is prepared in 2 steps in analogy to example 1 from the acid 1 and amine 22.

LCMS (A): $t_R$=0.71 min; [M+H]$^+$=645.90

Example 109: $^1$H NMR (500 MHz, DMSO) δ: 9.00 (s, 1H), 7.89 (dd, $J_1$=9.1 Hz, $J_2$=6.8 Hz, 2H), 7.77 (t, J=1.9 Hz, 1H), 7.57 (s, 1H), 7.27-7.34 (m, 1H), 5.33 (d, J=6.0 Hz, 1H), 4.88 (dd, $J_1$=2.9 Hz, $J_2$=10.8 Hz, 1H), 4.85 (d, J=5.4 Hz, 1H), 4.68 (t, J=5.4 Hz, 1H), 4.38 (dd, $J_1$=10.7 Hz, $J_2$=9.0 Hz, 1H), 4.24-4.33 (m, 1H), 3.79 (dd, $J_1$=6.1 Hz, $J_2$=3.0 Hz, 1H), 3.52-3.55 (m, 1H), 3.45 (m, 2H), 3.23-3.28 (m, 1H), 3.06 (s, 3H), 2.87-3.03 (m, 2H), 2.78-2.87 (m, 1H), 2.37-2.43 (m, 1H), 2.22-2.27 (m, 1H), 1.67-1.81 (m, 1H), 1.31-1.54 (m, 1H)

Example 113: (2R,3R,4S,5R,6R)—N-(3,5-dichlorophenyl)-5-hydroxy-6-(hydroxymethyl)-N-((3S,4S)-4-hydroxypiperidin-3-yl)-3-methoxy-4-(4-(3,4,5-trifluorophenyl)-1H-1,2,3-triazol-1-yl)tetrahydro-2H-pyran-2-carboxamide This product is prepared in 2 steps in analogy to example 1 from the acid 1 and amine 24.

LCMS (A): $t_R$=0.70 min; [M+H]$^+$=645.90

Example 113: $^1$H NMR (500 MHz, DMSO) δ: 9.00 (s, 1H), 7.89 (dd, $J_1$=6.8 Hz, $J_2$=9.1 Hz, 2H), 7.75 (t, J=1.9 Hz, 1H), 7.58 (s, 1H), 7.31-7.35 (m, 1H), 5.33 (d, J=6.0 Hz, 1H), 4.88 (dd, J$_1$=2.9 Hz, J$_2$=10.8 Hz, 1H), 4.85 (d, J=5.6 Hz, 1H), 4.69 (t, J=5.5 Hz, 1H), 4.39 (dd, J$_1$=10.7 Hz, J$_2$=9.0 Hz, 1H), 4.11-4.19 (m, 1H), 3.79 (dd, J$_1$=6.0 Hz, J$_2$=3.0 Hz, 1H), 3.52 (d, J=8.9 Hz, 1H), 3.45 (t, J=6.0 Hz, 2H), 3.26 (t, J=6.6 Hz, 1H), 3.10-3.21 (m, 1H), 3.07 (s, 3H), 2.96-2.99 (m, 1H), 2.78 (dd, J$_1$=10.9 Hz, J$_2$=1.3 Hz, 1H), 2.43-2.49 (m, 1H), 2.20-2.30 (m, 1H), 1.80-1.83 (m, 1H), 1.32-1.39 (m, 1H)

The following compounds are prepared are prepared in analogy to Example 1 from the corresponding acids and amines, or as described for the referenced Examples 59, 71, 72, 90, 99, 105, 109, or 113.

TABLE 1

| Example | Compound | t$_R$ [min] LC-MS A | MS Data m/z [M + H]$^+$ |
|---|---|---|---|
| 1 | (2R,3R,4S,5R,6R)-N-(3-chlorophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide 1,3-di-deoxy-2-O-methyl-3-[4-(3,4,5-trifluorophenyl)-1H-1,2,3-triazol-1-yl]-N-(3-chlorophenyl)-N-((3S,4R)-4-hydroxy-3-tetrahydrofuranyl)-beta-D-galacto-pyranose-1-carboxamide | 0.85 | 599.05 |
| 2 | (2R,3R,4S,5R,6R)-N-(3-bromophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.86 | 642.96 |
| 3 | (2R,3R,4S,5R,6R)-5-hydroxy-6-(hydroxymethyl)-N-((3S,4R)-4-hydroxytetrahydrofuran-3-yl)-N-(3-iodophenyl)-3-methoxy-4-(4-(3,4,5-trifluorophenyl)-1H-1,2,3-triazol-1-yl)tetrahydro-2H-pyran-2-carboxamide | 0.86 | 690.75 |
| 4 | (2R,3R,4S,5R,6R)-N-(3,5-dichlorophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.89 | 633.98 |
| 5 | (2R,3R,4S,5R,6R)-N-(3-chloro-5-cyanophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.85 | 624.07 |
| 6 | (2R,3R,4S,5R,6R)-N-(3,5-dibromophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.91 | 722.84 |
| 7 | (2R,3R,4S,5R,6R)-N-(3-bromo-5-cyanophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.86 | 669.58 |
| 8 | (2R,3R,4S,5R,6R)-N-(3-bromo-5-methylphenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.89 | 656.98 |
| 9 | (2R,3R,4S,5R,6R)-N-(3-cyano-5-methoxyphenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.83 | 620.08 |
| 10 | (2R,3R,4S,5R,6R)-N-(3-cyano-5-methylphenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.83 | 604.10 |
| 11 | (2R,3R,4S,5R,6R)-N-(3-cyano-5-fluorophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.83 | 608.06 |
| 12 | (2R,3R,4S,5R,6R)-4-(4-(4-bromo-2,3-difluorophenyl)-1H-1,2,3-triazol-1-yl)-N-(3,5-dichlorophenyl)-5-hydroxy-6-(hydroxymethyl)-N-((3S,4R)-4-hydroxytetrahydrofuran-3-yl)-3-methoxytetrahydro-2H-pyran-2-carboxamide | 0.92 | 694.88 |
| 13 | (2R,3R,4S,5R,6R)-4-(4-(4-bromo-2,3-difluorophenyl)-1H-1,2,3-triazol-1-yl)-N-(3-bromo-5-cyanophenyl)-5-hydroxy-6-(hydroxymethyl)-N-((3S,4R)-4-hydroxytetrahydrofuran-3-yl)-3-methoxytetrahydro-2H-pyran-2-carboxamide | 0.88 | 729.85 |
| 14 | (2R,3R,4S,5R,6R)-4-(4-(4-bromo-2,3-difluorophenyl)-1H-1,2,3-triazol-1-yl)-N-(3-bromo-5-methylphenyl)-5-hydroxy-6-(hydroxymethyl)-N-((3S,4R)-4-hydroxytetrahydrofuran-3-yl)-3-methoxytetrahydro-2H-pyran-2-carboxamide | 0.92 | 718.82 |
| 15 | (2R,3R,4S,5R,6R)-N-(3,5-dichlorophenyl)-4-(4-(3,5-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide | 0.91 | 629.02 |
| 16 | (2R,3R,4S,5R,6R)-N-(3,5-dibromophenyl)-4-(4-(3,5-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide | 0.92 | 718.79 |
| 17 | (2R,3R,4S,5R,6R)-N-(3-bromo-5-cyanophenyl)-4-(4-(3,5-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide | 0.87 | 665.96 |

TABLE 1-continued

| Example | Compound | $t_R$ [min] LC-MS A | MS Data m/z [M + H]$^+$ |
|---|---|---|---|
| 18 | (2R,3R,4S,5R,6R)-N-(3-bromo-5-methylphenyl)-4-(4-(3,5-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide | 0.90 | 654.95 |
| 19 | (2R,3R,4S,5R,6R)-N-(3,5-dichlorophenyl)-4-(4-(2,3-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide | 0.88 | 629.14 |
| 20 | (2R,3R,4S,5R,6R)-N-(3-bromo-5-cyanophenyl)-4-(4-(2,3-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide | 0.85 | 666.11 |
| 21 | (2R,3R,4S,5R,6R)-N-(3-bromo-5-methylphenyl)-4-(4-(2,3-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide | 0.88 | 655.09 |
| 22 | (2R,3R,4S,5R,6R)-4-(4-(4-chloro-3,5-difluorophenyl)-1H-1,2,3-triazol-1-yl)-N-(3,5-dichlorophenyl)-5-hydroxy-6-(hydroxymethyl)-N-((3S,4R)-4-hydroxytetrahydrofuran-3-yl)-3-methoxytetrahydro-2H-pyran-2-carboxamide | 0.92 | 649.06 |
| 23 | (2R,3R,4S,5R,6R)-4-(4-(4-chloro-3,5-difluorophenyl)-1H-1,2,3-triazol-1-yl)-N-(3,5-dibromophenyl)-5-hydroxy-6-(hydroxymethyl)-N-((3S,4R)-4-hydroxytetrahydrofuran-3-yl)-3-methoxytetrahydro-2H-pyran-2-carboxamide | 0.93 | 738.97 |
| 24 | (2R,3R,4S,5R,6R)-N-(3-bromo-5-cyanophenyl)-4-(4-(4-chloro-3,5-difluorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide | 0.88 | 685.67 |
| 25 | (2R,3R,4S,5R,6R)-N-(3-bromo-5-methylphenyl)-4-(4-(4-chloro-3,5-difluorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide | 0.91 | 675.05 |
| 26 | (2R,3R,4S,5R,6R)-N-(3,5-dichlorophenyl)-4-(4-(3,4-dichlorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide | 0.92 | 648.93 |
| 27 | (2R,3R,4S,5R,6R)-N-(3,5-dibromophenyl)-4-(4-(3,4-dichlorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide | 0.94 | 736.79 |
| 28 | (2R,3R,4S,5R,6R)-N-(3-bromo-5-cyanophenyl)-4-(4-(3,4-dichlorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide | 0.89 | 683.92 |
| 29 | (2R,3R,4S,5R,6R)-N-(3-bromo-5-methylphenyl)-4-(4-(3,4-dichlorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide | 0.92 | 672.92 |
| 30 | (2R,3R,4S,5R,6R)-N-(3-chlorophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.84 | 599.04 |
| 31 | (2R,3R,4S,5R,6R)-N-(3-bromophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.85 | 643.02 |
| 32 | (2R,3R,4S,5R,6R)-5-hydroxy-6-(hydroxymethyl)-N-((3R,4S)-4-hydroxytetrahydrofuran-3-yl)-N-(3-iodophenyl)-3-methoxy-4-(4-(3,4,5-trifluorophenyl)-1H-1,2,3-triazol-1-yl)tetrahydro-2H-pyran-2-carboxamide | 0.85 | 690.74 |
| 33 | (2R,3R,4S,5R,6R)-N-(3,5-dichlorophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.88 | 632.97 |
| 34 | (2R,3R,4S,5R,6R)-N-(3-chloro-5-cyanophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.85 | 624.03 |
| 35 | (2R,3R,4S,5R,6R)-N-(3,5-dibromophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.91 | 722.85 |
| 36 | (2R,3R,4S,5R,6R)-N-(3-bromo-5-cyanophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.85 | 669.47 |
| 37 | (2R,3R,4S,5R,6R)-N-(3-bromo-5-methylphenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.88 | 658.97 |
| 38 | (2R,3R,4S,5R,6R)-N-(3-cyano-5-methoxyphenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.82 | 620.07 |

TABLE 1-continued

| Example | Compound | $t_R$ [min] LC-MS A | MS Data m/z [M + H]+ |
|---|---|---|---|
| 39 | (2R,3R,4S,5R,6R)-N-(3-cyano-5-methylphenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.83 | 604.08 |
| 40 | (2R,3R,4S,5R,6R)-N-(3-cyano-5-fluorophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl)tetrahydro-2H-pyran-2-carboxamide | 0.82 | 608.07 |
| 41 | (2R,3R,4S,5R,6R)-4-(4-(4-bromo-2,3-difluorophenyl)-1H-1,2,3-triazol-1-yl)-N-(3,5-dichlorophenyl)-5-hydroxy-6-(hydroxymethyl)-N-((3R,4S)-4-hydroxytetrahydrofuran-3-yl)-3-methoxytetrahydro-2H-pyran-2-carboxamide | 0.91 | 694.87 |
| 42 | (2R,3R,4S,5R,6R)-4-(4-(4-bromo-2,3-difluorophenyl)-1H-1,2,3-triazol-1-yl)-N-(3-bromo-5-cyanophenyl)-5-hydroxy-6-(hydroxymethyl)-N-((3R,4S)-4-hydroxytetrahydrofuran-3-yl)-3-methoxytetrahydro-2H-pyran-2-carboxamide | 0.88 | 729.85 |
| 43 | (2R,3R,4S,5R,6R)-4-(4-(4-bromo-2,3-difluorophenyl)-1H-1,2,3-triazol-1-yl)-N-(3-bromo-5-methylphenyl)-5-hydroxy-6-(hydroxymethyl)-N-((3R,4S)-4-hydroxytetrahydrofuran-3-yl)-3-methoxytetrahydro-2H-pyran-2-carboxamide | 0.91 | 718.82 |
| 44 | (2R,3R,4S,5R,6R)-N-(3,5-dichlorophenyl)-4-(4-(3,5-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide | 0.90 | 629.08 |
| 45 | (2R,3R,4S,5R,6R)-N-(3,5-dibromophenyl)-4-(4-(3,5-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide | 0.91 | 718.83 |
| 46 | (2R,3R,4S,5R,6R)-N-(3-bromo-5-cyanophenyl)-4-(4-(3,5-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide | 0.87 | 663.97 |
| 47 | (2R,3R,4S,5R,6R)-N-(3-bromo-5-methylphenyl)-4-(4-(3,5-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide | 0.90 | 654.94 |
| 48 | (2R,3R,4S,5R,6R)-N-(3,5-dichlorophenyl)-4-(4-(2,3-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide | 0.88 | 629.19 |
| 49 | (2R,3R,4S,5R,6R)-N-(3-bromo-5-cyanophenyl)-4-(4-(2,3-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide | 0.84 | 664.10 |
| 50 | (2R,3R,4S,5R,6R)-N-(3-bromo-5-methylphenyl)-4-(4-(2,3-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide | 0.87 | 655.11 |
| 51 | (2R,3R,4S,5R,6R)-4-(4-(4-chloro-3,5-difluorophenyl)-1H-1,2,3-triazol-1-yl)-N-(3,5-dichlorophenyl)-5-hydroxy-6-(hydroxymethyl)-N-((3R,4S)-4-hydroxytetrahydrofuran-3-yl)-3-methoxytetrahydro-2H-pyran-2-carboxamide | 0.91 | 651.07 |
| 52 | (2R,3R,4S,5R,6R)-4-(4-(4-chloro-3,5-difluorophenyl)-1H-1,2,3-triazol-1-yl)-N-(3,5-dibromophenyl)-5-hydroxy-6-(hydroxymethyl)-N-((3R,4S)-4-hydroxytetrahydrofuran-3-yl)-3-methoxytetrahydro-2H-pyran-2-carboxamide | 0.92 | 738.96 |
| 53 | (2R,3R,4S,5R,6R)-N-(3-bromo-5-cyanophenyl)-4-(4-(4-chloro-3,5-difluorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide | 0.87 | 685.63 |
| 54 | (2R,3R,4S,5R,6R)-N-(3-bromo-5-methylphenyl)-4-(4-(4-chloro-3,5-difluorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide | 0.90 | 675.06 |
| 55 | (2R,3R,4S,5R,6R)-N-(3,5-dichlorophenyl)-4-(4-(3,4-dichlorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide | 0.92 | 648.93 |
| 56 | (2R,3R,4S,5R,6R)-N-(3,5-dibromophenyl)-4-(4-(3,4-dichlorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide | 0.93 | 736.78 |
| 57 | (2R,3R,4S,5R,6R)-N-(3-bromo-5-cyanophenyl)-4-(4-(3,4-dichlorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide | 0.88 | 683.90 |
| 58 | (2R,3R,4S,5R,6R)-N-(3-bromo-5-methylphenyl)-4-(4-(3,4-dichlorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide | 0.91 | 672.92 |

TABLE 1-continued

| Example | Compound | $t_R$ [min] LC-MS A | MS Data m/z [M + H]+ |
|---|---|---|---|
| 59 | (2R,3R,4S,5R,6R)-N-(3,5-dichlorophenyl)-5-hydroxy-6-(hydroxymethyl)-N-((3S,4S)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide 1,3-di-deoxy-2-O-methyl-3-[4-(3,4,5-trifluorophenyl)-1H-1,2,3-triazol-1-yl]-N-(3,5-dichlorophenyl)-N-((3S,4S)-4-hydroxy-pyrrolidin-3-yl)-beta-D-galacto-pyranose-1-carboxamide | 0.71 | 631.96 |
| 60 | (2R,3R,4S,5R,6R)-N-(3-bromo-5-cyanophenyl)-5-hydroxy-6-(hydroxymethyl)-N-((3S,4S)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide | 0.70 | 666.86 |
| 61 | (2R,3R,4S,5R,6R)-N-(3-bromo-5-methylphenyl)-5-hydroxy-6-(hydroxymethyl)-N-((3S,4S)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide | 0.72 | 655.83 |
| 62 | (2R,3R,4S,5R,6R)-4-(4-(4-bromo-2,3-difluorophenyl)-1H-1,2,3-triazol-1-yl)-N-(3,5-dichlorophenyl)-5-hydroxy-6-(hydroxymethyl)-N-((3S,4S)-4-hydroxypyrrolidin-3-yl)-3-methoxytetrahydro-2H-pyran-2-carboxamide | 0.73 | 693.45 |
| 63 | (2R,3R,4S,5R,6R)-N-(3,5-dichlorophenyl)-4-(4-(2,3-difluoro-4-methylphenyl)-1H-1,2,3-triazol-1-yl)-5-hydroxy-6-(hydroxymethyl)-N-((3S,4S)-4-hydroxypyrrolidin-3-yl)-3-methoxytetrahydro-2H-pyran-2-carboxamide | 0.71 | 627.81 |
| 64 | (2R,3R,4S,5R,6R)-N-(3-bromo-5-methylphenyl)-4-(4-(2,3-difluoro-4-methylphenyl)-1H-1,2,3-triazol-1-yl)-5-hydroxy-6-(hydroxymethyl)-N-((3S,4S)-4-hydroxypyrrolidin-3-yl)-3-methoxytetrahydro-2H-pyran-2-carboxamide | 0.70 | 651.96 |
| 65 | (2R,3R,4S,5R,6R)-N-(3,5-dichlorophenyl)-4-(4-(3,4-dichlorophenyl)-1H-1,2,3-triazol-1-yl)-5-hydroxy-6-(hydroxymethyl)-N-((3S,4S)-4-hydroxypyrrolidin-3-yl)-3-methoxytetrahydro-2H-pyran-2-carboxamide | 0.74 | 647.73 |
| 66 | (2R,3R,4S,5R,6R)-N-(3,5-dichlorophenyl)-5-hydroxy-6-(hydroxymethyl)-N-((3R,4R)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide | 0.71 | 631.98 |
| 67 | (2R,3R,4S,5R,6R)-N-(3-bromo-5-cyanophenyl)-5-hydroxy-6-(hydroxymethyl)-N-((3R,4R)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide | 0.70 | 666.86 |
| 68 | (2R,3R,4S,5R,6R)-N-(3-bromo-5-methylphenyl)-5-hydroxy-6-(hydroxymethyl)-N-((3R,4R)-4-hydroxypyrrolidin-3-yl)-3-methoxy-4-(4-(3,4,5-trifluorophenyl)-1H-1,2,3-triazol-1-yl)tetrahydro-2H-pyran-2-carboxamide | 0.72 | 655.85 |
| 69 | (2R,3R,4S,5R,6R)-N-(3-bromo-5-methylphenyl)-4-(4-(2,3-difluoro-4-methylphenyl)-1H-1,2,3-triazol-1-yl)-5-hydroxy-6-(hydroxymethyl)-N-((3R,4R)-4-hydroxypyrrolidin-3-yl)-3-methoxytetrahydro-2H-pyran-2-carboxamide | 0.70 | 653.94 |
| 70 | mixture of two diastereomers:<br>(2R,3R,4S,5R,6R)-N-(3-bromo-5-methylphenyl)-4-(4-(3,5-difluoro-4-methylphenyl)-1H-1,2,3-triazol-1-yl)-5-hydroxy-6-(hydroxymethyl)-N-((3S,4S)-4-hydroxypyrrolidin-3-yl)-3-methoxytetrahydro-2H-pyran-2-carboxamide<br>(2R,3R,4S,5R,6R)-N-(3-bromo-5-methylphenyl)-4-(4-(3,5-difluoro-4-methylphenyl)-1H-1,2,3-triazol-1-yl)-5-hydroxy-6-(hydroxymethyl)-N-((3R,4R)-4-hydroxypyrrolidin-3-yl)-3-methoxytetrahydro-2H-pyran-2-carboxamide | 0.72 | 653.84 |
| 71 | (2R,3R,4S,5R,6R)-N-((3S,4S)-1-acetyl-4-hydroxypyrrolidin-3-yl)-N-(3,5-dichlorophenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide | 0.85 | 673.86 |
| 72 | (2R,3R,4S,5R,6R)-N-((3S,4S)-1-acetyl-4-hydroxypyrrolidin-3-yl)-N-(3-bromo-5-methylphenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide | 0.84 | 697.91 |
| 73 | (2R,3R,4S,5R,6R)-N-((3S,4S)-1-acetyl-4-hydroxypyrrolidin-3-yl)-4-(4-(4-bromo-2,3-difluorophenyl)-1H-1,2,3-triazol-1-yl)-N-(3,5-dichlorophenyl)-5-hydroxy-6-(hydroxymethyl)-3-methoxytetrahydro-2H-pyran-2-carboxamide | 0.98 | 734.27 |
| 74 | (2R,3R,4S,5R,6R)-N-((3S,4S)-1-acetyl-4-hydroxypyrrolidin-3-yl)-N-(3,5-dibromophenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide | 0.98 | 758.26 |
| 75 | (2R,3R,4S,5R,6R)-N-((3S,4S)-1-acetyl-4-hydroxypyrrolidin-3-yl)-N-(3-bromo-5-methylphenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide | 0.85 | 693.96 |
| 76 | (2R,3R,4S,5R,6R)-N-((3S,4S)-1-acetyl-4-hydroxypyrrolidin-3-yl)-N-(3-bromo-5-methylphenyl)-4-(4-(4-chloro-3,5-difluorophenyl)-1H-1,2,3-triazol-1-yl)-5-hydroxy-6-(hydroxymethyl)-3-methoxytetrahydro-2H-pyran-2-carboxamide | 0.87 | 715.86 |
| 77 | (2R,3R,4S,5R,6R)-N-((3R,4R)-1-acetyl-4-hydroxypyrrolidin-3-yl)-N-(3,5-dichlorophenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide | 0.84 | 673.85 |

TABLE 1-continued

| Example | Compound | $t_R$ [min] LC-MS A | MS Data m/z [M + H]⁺ |
|---|---|---|---|
| 78 | (2R,3R,4S,5R,6R)-N-((3R,4R)-1-acetyl-4-hydroxypyrrolidin-3-yl)-N-(3-bromo-5-cyanophenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide | 0.82 | 710.84 |
| 79 | (2R,3R,4S,5R,6R)-N-((3R,4R)-1-acetyl-4-hydroxypyrrolidin-3-yl)-N-(3-bromo-5-methylphenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide | 0.83 | 697.93 |
| 80 | (2R,3R,4S,5R,6R)-N-((3R,4R)-1-acetyl-4-hydroxypyrrolidin-3-yl)-4-(4-(4-bromo-2,3-difluorophenyl)-1H-1,2,3-triazol-1-yl)-N-(3,5-dichlorophenyl)-5-hydroxy-6-(hydroxymethyl)-3-methoxytetrahydro-2H-pyran-2-carboxamide | 0.98 | 734.24 |
| 81 | (2R,3R,4S,5R,6R)-N-((3R,4R)-1-acetyl-4-hydroxypyrrolidin-3-yl)-N-(3,5-dibromophenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide | 0.98 | 758.26 |
| 82 | (2R,3R,4S,5R,6R)-N-((3R,4R)-1-acetyl-4-hydroxypyrrolidin-3-yl)-N-(3-bromo-5-methylphenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide | 0.83 | 693.97 |
| 83 | (2R,3R,4S,5R,6R)-N-((3R,4R)-1-acetyl-4-hydroxypyrrolidin-3-yl)-N-(3-bromo-5-methylphenyl)-4-(4-(4-chloro-3,5-difluorophenyl)-1H-1,2,3-triazol-1-yl)-5-hydroxy-6-(hydroxymethyl)-3-methoxytetrahydro-2H-pyran-2-carboxamide | 0.86 | 715.88 |
| 84 | mixture of two diastereomers: (2R,3R,4S,5R,6R)-N-((3S,4S)-1-acetyl-4-hydroxypyrrolidin-3-yl)-N-(3,5-dibromophenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide (2R,3R,4S,5R,6R)-N-((3R,4R)-1-acetyl-4-hydroxypyrrolidin-3-yl)-N-(3,5-dibromophenyl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide | 0.85 | 763.73 |
| 85 | mixture of two diastereomers: (2R,3R,4S,5R,6R)-N-((3S,4S)-1-acetyl-4-hydroxypyrrolidin-3-yl)-N-(3,5-dichlorophenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide (2R,3R,4S,5R,6R)-N-((3R,4R)-1-acetyl-4-hydroxypyrrolidin-3-yl)-N-(3,5-dichlorophenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide | 0.85 | 669.83 |
| 86 | mixture of two diastereomers: (2R,3R,4S,5R,6R)-N-((3S,4S)-1-acetyl-4-hydroxypyrrolidin-3-yl)-4-(4-(4-chloro-3,5-difluorophenyl)-1H-1,2,3-triazol-1-yl)-N-(3,5-dichlorophenyl)-5-hydroxy-6-(hydroxymethyl)-3-methoxytetrahydro-2H-pyran-2-carboxamide (2R,3R,4S,5R,6R)-N-((3R,4R)-1-acetyl-4-hydroxypyrrolidin-3-yl)-4-(4-(4-chloro-3,5-difluorophenyl)-1H-1,2,3-triazol-1-yl)-N-(3,5-dichlorophenyl)-5-hydroxy-6-(hydroxymethyl)-3-methoxytetrahydro-2H-pyran-2-carboxamide | 0.87 | 689.82 |
| 87 | mixture of two diastereomers: (2R,3R,4S,5R,6R)-N-((3S,4S)-1-acetyl-4-hydroxypyrrolidin-3-yl)-4-(4-(4-chloro-3,5-difluorophenyl)-1H-1,2,3-triazol-1-yl)-N-(3,5-dibromophenyl)-5-hydroxy-6-(hydroxymethyl)-3-methoxytetrahydro-2H-pyran-2-carboxamide (2R,3R,4S,5R,6R)-N-((3R,4R)-1-acetyl-4-hydroxypyrrolidin-3-yl)-4-(4-(4-chloro-3,5-difluorophenyl)-1H-1,2,3-triazol-1-yl)-N-(3,5-dibromophenyl)-5-hydroxy-6-(hydroxymethyl)-3-methoxytetrahydro-2H-pyran-2-carboxamide | 0.88 | 779.73 |
| 88 | mixture of two diastereomers: (2R,3R,4S,5R,6R)-N-((3S,4S)-1-acetyl-4-hydroxypyrrolidin-3-yl)-N-(3,5-dichlorophenyl)-4-(4-(3,4-dichlorophenyl)-1H-1,2,3-triazol-1-yl)-5-hydroxy-6-(hydroxymethyl)-3-methoxytetrahydro-2H-pyran-2-carboxamide (2R,3R,4S,5R,6R)-N-((3R,4R)-1-acetyl-4-hydroxypyrrolidin-3-yl)-N-(3,5-dichlorophenyl)-4-(4-(3,4-dichlorophenyl)-1H-1,2,3-triazol-1-yl)-5-hydroxy-6-(hydroxymethyl)-3-methoxytetrahydro-2H-pyran-2-carboxamide | 0.86 | 689.79 |
| 89 | (2R,3R,4S,5R,6R)-N-(3-bromo-5-cyanophenyl)-N-((3S,4S)-1-formyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide | 0.84 | 696.84 |
| 90 | (2R,3R,4S,5R,6R)-N-(3-bromo-5-methylphenyl)-N-((3S,4S)-1-formyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide | 0.84 | 683.83 |
| 91 | (2R,3R,4S,5R,6R)-4-(4-(4-bromo-2,3-difluorophenyl)-1H-1,2,3-triazol-1-yl)-N-(3,5-dichlorophenyl)-N-((3S,4S)-1-formyl-4-hydroxypyrrolidin-3-yl)-5-hydroxy-6-(hydroxymethyl)-3-methoxytetrahydro-2H-pyran-2-carboxamide | 0.87 | 721.73 |
| 92 | (2R,3R,4S,5R,6R)-N-(3-bromo-5-methylphenyl)-4-(4-(2,3-difluoro-4-methylphenyl)-1H-1,2,3-triazol-1-yl)-N-((3S,4S)-1-formyl-4- | 0.83 | 679.81 |

TABLE 1-continued

| Example | Compound | $t_R$ [min] LC-MS A | MS Data m/z [M + H]+ |
|---|---|---|---|
| | hydroxypyrrolidin-3-yl)-5-hydroxy-6-(hydroxymethyl)-3-methoxytetrahydro-2H-pyran-2-carboxamide | | |
| 93 | (2R,3R,4S,5R,6R)-N-(3-bromo-5-cyanophenyl)-N-((3R,4R)-1-formyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide | 0.81 | 696.88 |
| 94 | (2R,3R,4S,5R,6R)-N-(3-bromo-5-methylphenyl)-N-((3R,4R)-1-formyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide | 0.84 | 685.83 |
| 95 | (2R,3R,4S,5R,6R)-N-(3-bromo-5-methylphenyl)-4-(4-(2,3-difluoro-4-methylphenyl)-1H-1,2,3-triazol-1-yl)-N-((3R,4R)-1-formyl-4-hydroxypyrrolidin-3-yl)-5-hydroxy-6-(hydroxymethyl)-3-methoxytetrahydro-2H-pyran-2-carboxamide | 0.83 | 679.87 |
| 96 | (2R,3R,4S,5R,6R)-N-(3-bromo-5-methylphenyl)-5-hydroxy-N-((3S,4S)-4-hydroxy-1-methylpyrrolidin-3-yl)-6-(hydroxymethyl)-3-methoxy-4-(4-(3,4,5-trifluorophenyl)-1H-1,2,3-triazol-1-yl)tetrahydro-2H-pyran-2-carboxamide | 0.73 | 671.96 |
| 97 | (2R,3R,4S,5R,6R)-N-(3-bromo-5-methylphenyl)-N-((3S,4S)-1-ethyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl)tetrahydro-2H-pyran-2-carboxamide | 0.75 | 684.01 |
| 98 | (2R,3R,4S,5R,6R)-N-(3-bromo-5-methylphenyl)-5-hydroxy-N-((3S,4S)-4-hydroxy-1-(methylsulfonyl)pyrrolidin-3-yl)-6-(hydroxymethyl)-3-methoxy-4-(4-(3,4,5-trifluorophenyl)-1H-1,2,3-triazol-1-yl)tetrahydro-2H-pyran-2-carboxamide | 0.90 | 735.95 |
| 99 | (2R,3R,4S,5R,6R)-N-(3,5-dichlorophenyl)-5-hydroxy-6-(hydroxymethyl)-N-((3R,4S)-3-hydroxytetrahydro-2H-pyran-4-yl)-3-methoxy-4-(4-(3,4,5-trifluorophenyl)-1H-1,2,3-triazol-1-yl)tetrahydro-2H-pyran-2-carboxamide 1,3-di-deoxy-2-O-methyl-3-[4-(3,4,5-trifluorophenyl)-1H-1,2,3-triazol-1-yl]-N-(3,5-dichlorophenyl)-N-((3R,4S)-3-hydroxytetrahydro-2H-pyran-4-yl)-beta-D-galacto-pyranose-1-carboxamide | 0.93 | 646.97 |
| 100 | (2R,3R,4S,5R,6R)-N-(3-chloro-5-cyanophenyl)-5-hydroxy-6-(hydroxymethyl)-N-((3R,4S)-3-hydroxytetrahydro-2H-pyran-4-yl)-3-methoxy-4-(4-(3,4,5-trifluorophenyl)-1H-1,2,3-triazol-1-yl)tetrahydro-2H-pyran-2-carboxamide | 0.89 | 637.92 |
| 101 | (2R,3R,4S,5R,6R)-N-(3-bromo-5-cyanophenyl)-5-hydroxy-6-(hydroxymethyl)-N-((3R,4S)-3-hydroxytetrahydro-2H-pyran-4-yl)-3-methoxy-4-(4-(3,4,5-trifluorophenyl)-1H-1,2,3-triazol-1-yl)tetrahydro-2H-pyran-2-carboxamide | 0.89 | 682.01 |
| 102 | (2R,3R,4S,5R,6R)-N-(3-bromo-5-methylphenyl)-5-hydroxy-6-(hydroxymethyl)-N-((3R,4S)-3-hydroxytetrahydro-2H-pyran-4-yl)-3-methoxy-4-(4-(3,4,5-trifluorophenyl)-1H-1,2,3-triazol-1-yl)tetrahydro-2H-pyran-2-carboxamide | 0.93 | 671.00 |
| 103 | (2R,3R,4S,5R,6R)-N-(3,5-dichlorophenyl)-5-hydroxy-6-(hydroxymethyl)-N-((3S,4R)-3-hydroxytetrahydro-2H-pyran-4-yl)-3-methoxy-4-(4-(3,4,5-trifluorophenyl)-1H-1,2,3-triazol-1-yl)tetrahydro-2H-pyran-2-carboxamide | 0.91 | 646.96 |
| 104 | (2R,3R,4S,5R,6R)-N-(3-bromo-5-methylphenyl)-5-hydroxy-6-(hydroxymethyl)-N-((3S,4R)-3-hydroxytetrahydro-2H-pyran-4-yl)-3-methoxy-4-(4-(3,4,5-trifluorophenyl)-1H-1,2,3-triazol-1-yl)tetrahydro-2H-pyran-2-carboxamide | 0.90 | 671.00 |
| 105 | (2R,3R,4S,5R,6R)-N-(3,5-dichlorophenyl)-5-hydroxy-6-(hydroxymethyl)-N-((3S,4S)-4-hydroxytetrahydro-2H-pyran-3-yl)-3-methoxy-4-(4-(3,4,5-trifluorophenyl)-1H-1,2,3-triazol-1-yl)tetrahydro-2H-pyran-2-carboxamide | 0.93 | 647.00 |
| 106 | (2R,3R,4S,5R,6R)-N-(3-bromo-5-methylphenyl)-5-hydroxy-6-(hydroxymethyl)-N-((3S,4S)-4-hydroxytetrahydro-2H-pyran-3-yl)-3-methoxy-4-(4-(3,4,5-trifluorophenyl)-1H-1,2,3-triazol-1-yl)tetrahydro-2H-pyran-2-carboxamide | 0.92 | 671.00 |
| 107 | (2R,3R,4S,5R,6R)-N-(3,5-dichlorophenyl)-5-hydroxy-6-(hydroxymethyl)-N-((3R,4R)-4-hydroxytetrahydro-2H-pyran-3-yl)-3-methoxy-4-(4-(3,4,5-trifluorophenyl)-1H-1,2,3-triazol-1-yl)tetrahydro-2H-pyran-2-carboxamide | 0.91 | 646.97 |
| 108 | (2R,3R,4S,5R,6R)-N-(3-bromo-5-methylphenyl)-5-hydroxy-6-(hydroxymethyl)-N-((3R,4R)-4-hydroxytetrahydro-2H-pyran-3-yl)-3-methoxy-4-(4-(3,4,5-trifluorophenyl)-1H-1,2,3-triazol-1-yl)tetrahydro-2H-pyran-2-carboxamide | 0.90 | 670.97 |
| 109 | (2R,3R,4S,5R,6R)-N-(3,5-dichlorophenyl)-5-hydroxy-6-(hydroxymethyl)-N-((3S,4S)-3-hydroxypiperidin-4-yl)-3-methoxy-4-(4-(3,4,5-trifluorophenyl)-1H-1,2,3-triazol-1-yl)tetrahydro-2H-pyran-2-carboxamide 1,3-di-deoxy-2-O-methyl-3-[4-(3,4,5-trifluorophenyl)-1H-1,2,3-triazol-1-yl]-N-(3,5-dichlorophenyl)-N-((3S,4S)-3-hydroxypiperidin-4-yl)-beta-D-galacto-pyranose-1-carboxamide | 0.71 | 645.90 |
| 110 | (2R,3R,4S,5R,6R)-N-(3-bromo-5-cyanophenyl)-5-hydroxy-6-(hydroxymethyl)-N-((3S,4S)-3-hydroxypiperidin-4-yl)-3-methoxy-4-(4-(3,4,5-trifluorophenyl)-1H-1,2,3-triazol-1-yl)tetrahydro-2H-pyran-2-carboxamide | 0.70 | 680.97 |
| 111 | (2R,3R,4S,5R,6R)-N-(3-bromo-5-methylphenyl)-5-hydroxy-6-(hydroxymethyl)-N-((3S,4S)-3-hydroxypiperidin-4-yl)-3-methoxy-4-(4- | 0.71 | 669.63 |

TABLE 1-continued

| Example | Compound | $t_R$ [min] LC-MS A | MS Data m/z $[M + H]^+$ |
|---|---|---|---|
| | (3,4,5-trifluorophenyl)-1H-1,2,3-triazol-1-yl)tetrahydro-2H-pyran-2-carboxamide | | |
| 112 | (2R,3R,4S,5R,6R)-N-(3-bromo-5-methylphenyl)-5-hydroxy-6-(hydroxymethyl)-N-((3R,4R)-3-hydroxypiperidin-4-yl)-3-methoxy-4-(4-(3,4,5-trifluorophenyl)-1H-1,2,3-triazol-1-yl)tetrahydro-2H-pyran-2-carboxamide | 0.71 | 669.65 |
| 113 | (2R,3R,4S,5R,6R)-N-(3,5-dichlorophenyl)-5-hydroxy-6-(hydroxymethyl)-N-((3S,4S)-4-hydroxypiperidin-3-yl)-3-methoxy-4-(4-(3,4,5-trifluorophenyl)-1H-1,2,3-triazol-1-yl)tetrahydro-2H-pyran-2-carboxamide | 0.70 | 645.90 |
| 114 | (2R,3R,4S,5R,6R)-N-(3-bromo-5-methylphenyl)-5-hydroxy-6-(hydroxymethyl)-N-((3S,4S)-4-hydroxypiperidin-3-yl)-3-methoxy-4-(4-(3,4,5-trifluorophenyl)-1H-1,2,3-triazol-1-yl)tetrahydro-2H-pyran-2-carboxamide | 0.72 | 669.66 |
| 115 | (2R,3R,4S,5R,6R)-N-(3-bromo-5-methylphenyl)-5-hydroxy-6-(hydroxymethyl)-N-((3R,4R)-4-hydroxypiperidin-3-yl)-3-methoxy-4-(4-(3,4,5-trifluorophenyl)-1H-1,2,3-triazol-1-yl)tetrahydro-2H-pyran-2-carboxamide | 0.71 | 669.61 |

II. Biological Assays

Evaluation of Compound Inhibitory Activity ($IC_{50}$)

The inhibitory activity of compounds is determined in competitive binding assays. This spectrophotometric assay measures the binding of biotinylated human Gal-3 (hGal-3) or human Gal-1 (hGal-1), respectively, to a microplate-adsorbed glycoprotein, asialofetuin (ASF) (Proc Natl Acad Sci USA. 2013 Mar. 26; 110(13):5052-7.). Alternatively, and preferably, a human Gal-1 version in which all six cysteines are substituted by serines may be used.

Briefly, compounds are serially diluted in DMSO (working dilutions). ASF-coated 384 well plates are supplemented with 22.8 µL/well of biotinylated hGal-3 or hGal-1 in assay buffer (i.e. 300-1000 ng/mL biotinylated hGal-3 or hGal-1) to which 1.2 µL of compound working dilutions are added and mixed.

Plates are incubated for 3 hours at 4° C., then washed with cold assay buffer (3×50 uL), incubated for 1 hour with 25 µL/well of a streptavidin-peroxidase solution (diluted in assay buffer to 80 ng/mL at 4° C., followed by further washing steps with assay buffer (3×50 uL). Finally, 25 µL/well of ABTS substrate is added. OD (410 nm) is recorded after 30 to 45 min and $IC_{50}$ values are calculated.

The calculated $IC_{50}$ values may fluctuate depending on the daily assay performance. Fluctuations of this kind are known to those skilled in the art. $IC_{50}$ values from several measurements are given as mean values.

TABLE 2

Activity on hGal-3 ($IC_{50}$ in nM):

| Example | Gal-3 $IC_{50}$ [nM] | Example | Gal-3 $IC_{50}$ [nM] | Example | Gal-3 $IC_{50}$ [nM] | Example | Gal-3 $IC_{50}$ [nM] |
|---|---|---|---|---|---|---|---|
| 1 | 102 | 2 | 80 | 3 | 56 | 4 | 72 |
| 5 | 69 | 6 | 53 | 7 | 83 | 8 | 77 |
| 9 | 101 | 10 | 136 | 11 | 124 | 12 | 47 |
| 13 | 15 | 14 | 46 | 15 | 38 | 16 | 61 |
| 17 | 66 | 18 | 69 | 19 | 40 | 20 | 31 |
| 21 | 35 | 22 | 50 | 23 | 55 | 24 | 73 |
| 25 | 31 | 26 | 162 | 27 | 89 | 28 | 115 |
| 29 | 153 | 30 | 235 | 31 | 103 | 32 | 130 |
| 33 | 104 | 34 | 102 | 35 | 84 | 36 | 67 |
| 37 | 186 | 38 | 113 | 39 | 69 | 40 | 145 |
| 41 | 63 | 42 | 37 | 43 | 33 | 44 | 81 |
| 45 | 59 | 46 | 81 | 47 | 72 | 48 | 29 |
| 49 | 18 | 50 | 34 | 51 | 73 | 52 | 86 |
| 53 | 46 | 54 | 89 | 55 | 164 | 56 | 222 |
| 57 | 151 | 58 | 175 | 59 | 23 | 60 | 51 |
| 61 | 26 | 62 | 12 | 63 | 24 | 64 | 25 |
| 65 | 54 | 66 | 182 | 67 | 129 | 68 | 222 |
| 69 | 38 | 70 | 56 | 71 | 36 | 72 | 26 |
| 73 | 23 | 74 | 27 | 75 | 22 | 76 | 37 |
| 77 | 80 | 78 | 71 | 79 | 76 | 80 | 31 |
| 81 | 40 | 82 | 45 | 83 | 67 | 84 | 70 |
| 85 | 327 | 86 | 64 | 87 | 36 | 88 | 71 |
| 89 | 38 | 90 | 20 | 91 | 20 | 92 | 19 |
| 93 | 80 | 94 | 86 | 95 | 40 | 96 | 51 |
| 97 | 24 | 98 | 29 | 99 | 16 | 100 | 16 |
| 101 | 14 | 102 | 14 | 103 | 299 | 104 | 256 |
| 105 | 18 | 106 | 13 | 107 | 217 | 108 | 315 |
| 109 | 12 | 110 | 17 | 111 | 14 | 112 | 184 |
| 113 | 13 | 114 | 9 | 115 | 196 | | |

TABLE 3

Activity on hGal-1 ($IC_{50}$ in nM):

| Example | Gal-1 $IC_{50}$ [nM] | Example | Gal-1 $IC_{50}$ [nM] | Example | Gal-1 $IC_{50}$ [nM] | Example | Gal-1 $IC_{50}$ [nM] |
|---|---|---|---|---|---|---|---|
| 1 | 2427 | 2 | 1680 | 3 | 2713 | 4 | 1298 |
| 5 | 801 | 6 | 689 | 7 | 956 | 8 | 1412 |
| 9 | 1475 | 10 | 1453 | 11 | 1723 | 12 | 807 |
| 13 | 593 | 14 | 1944 | 15 | 1934 | 16 | 2281 |
| 17 | 1415 | 18 | 3638 | 19 | 1355 | 20 | 1121 |
| 21 | 1758 | 22 | 2012 | 23 | 2492 | 24 | 1414 |
| 25 | 3061 | 26 | 788 | 27 | 950 | 28 | 308 |
| 29 | 1259 | 30 | 3870 | 31 | 3268 | 32 | 3887 |
| 33 | 1612 | 34 | 1195 | 35 | 2478 | 36 | 836 |
| 37 | 2477 | 38 | 1648 | 39 | 1458 | 40 | 1363 |
| 41 | 999 | 42 | 1030 | 43 | 3266 | 44 | 2524 |
| 45 | 2537 | 46 | 1419 | 47 | 6187 | 48 | 1451 |
| 49 | 1165 | 50 | 3280 | 51 | 3250 | 52 | 3506 |
| 53 | 2417 | 54 | 7387 | 55 | 982 | 56 | 1468 |
| 57 | 791 | 58 | 1563 | 59 | 148 | 60 | 456 |
| 61 | 235 | 62 | 167 | 63 | 226 | 64 | 218 |
| 65 | 93 | 66 | 1496 | 67 | 1828 | 68 | 1928 |

TABLE 3-continued

Activity on hGal-1 ($IC_{50}$ in nM):

| Example | Gal-1 $IC_{50}$ [nM] | Example | Gal-1 $IC_{50}$ [nM] | Example | Gal-1 $IC_{50}$ [nM] | Example | Gal-1 $IC_{50}$ [nM] |
|---|---|---|---|---|---|---|---|
| 69 | 1229 | 70 | 1798 | 71 | 349 | 72 | 756 |
| 73 | 422 | 74 | 778 | 75 | 1040 | 76 | 1046 |
| 77 | 1280 | 78 | 1347 | 79 | 1866 | 80 | 973 |
| 81 | 2085 | 82 | 3016 | 83 | 1993 | 84 | 1210 |
| 85 | 13400 | 86 | 1780 | 87 | 1860 | 88 | 657 |
| 89 | 587 | 90 | 893 | 91 | 357 | 92 | 491 |
| 93 | 776 | 94 | 2289 | 95 | 1085 | 96 | 670 |
| 97 | 288 | 98 | 1160 | 99 | 73 | 100 | 147 |
| 101 | 109 | 102 | 311 | 103 | 2530 | 104 | 21300 |
| 105 | 147 | 106 | 314 | 107 | 1638 | 108 | 5030 |
| 109 | 49 | 110 | 51 | 111 | 76 | 112 | 1170 |
| 113 | 31 | 114 | 40 | 115 | 1240 | | |

Compounds of the present invention may be further characterized with regard to their general pharmacokinetic and pharmacological properties using conventional assays well known in the art; for example relating to their bioavailability in different species (such as rat or dog) including aspects such as solubility, permeability, metabolic stability, absorption, etc.; or for their properties with regard to drug safety and/or toxicological properties using conventional assays well known in the art, for example relating to cytochrome P450 enzyme inhibition and time dependent inhibition, pregnane X receptor (PXR) activation, glutathione binding, or phototoxic behavior.

The invention claimed is:

1. A compound of Formula (I):

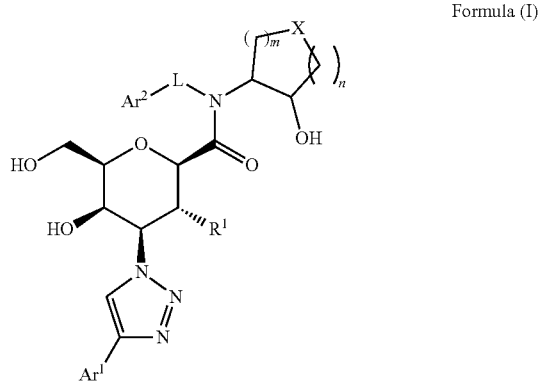

Formula (I)

wherein n and m each, independently, represent the integer 1 or 2 such that n+m equals 2 or 3;

X represents O or $NR^2$; wherein $R^2$ represents hydrogen, $C_{1-3}$-alkyl, —CO—H, —$SO_2$—$C_{1-3}$-alkyl, or —CO—$C_{1-3}$-alkyl;

$Ar^1$ represents

Aryl, which is mono-, di-, tri-, tetra-, or penta-substituted, wherein the substituents are independently selected from halogen; methyl; cyano; methoxy; trifluoromethyl; trifluoromethoxy; and $NR^{N11}R^{N12}$ wherein $R^{N11}$ represents hydrogen and $R^{N12}$ represents hydroxy-$C_{2-3}$-alkyl, or $R^{N11}$ and $R^{N12}$ together with the nitrogen atom to which they are attached form a 4- to 6-membered heterocyclyl selected from morpholin-4-yl, azetidine-1-yl, pyrrolidine-1-yl, and piperidine-1-yl, wherein said 4- to 6-membered heterocyclyl is unsubstituted or mono-substituted with hydroxy;

5- or 6-membered heteroaryl, wherein said 5- or 6-membered heteroaryl independently is unsubstituted, mono- or di-substituted, wherein the substituents are independently selected from halogen, methyl, cyano, and methoxy; or 9- or 10-membered heteroaryl, wherein said 9- or 10-membered heteroaryl independently is unsubstituted, or mono-substituted with methyl;

$R^1$ represents hydroxy;

$C_{1-3}$-alkoxy;

—O—CO—$C_{1-3}$-alkyl;

—O—$CH_2$—$CH_2$—OH; or

—O—$CH_2$—CO—$R^{1X}$ wherein $R^{1X}$ represents

-hydroxy;

morpholin-4-yl; or

—$NR^{N21}R^{N22}$, wherein $R^{N21}$ and $R^{N22}$ together with the nitrogen atom to which they are attached form a 4- to 6-membered heterocyclyl selected from azetidine-1-yl, pyrrolidine-1-yl, and piperidine-1-yl, wherein said 4- to 6-membered heterocyclyl is mono-substituted with hydroxy;

L represents a direct bond, methylene, or ethylene; and $Ar^2$ represents phenyl or 5- or 6-membered heteroaryl, wherein said phenyl or 5- or 6-membered heteroaryl independently is unsubstituted, or mono-, di- or tri-substituted; wherein the substituents are independently selected from $C_{1-6}$-alkyl, $C_{3-6}$-cycloalkyl, —$CH_2$—$C_{3-6}$-cycloalkyl, $C_{1-3}$-fluoroalkyl, $C_{1-3}$-fluoroalkoxy, $C_{1-3}$-alkoxy, halogen, morpholine-4-yl, amino, ethynyl, and cyano;

9-membered bicyclic heteroaryl or 10-membered bicyclic heteroaryl, wherein said 9- or 10-membered bicyclic heteroaryl independently is unsubstituted, mono- or di-substituted, wherein the substituents are independently selected from methyl, methoxy, and halogen; or naphthyl;

or a pharmaceutically acceptable salt thereof.

2. The compound of Formula (I) according to claim 1, wherein said compound is also a compound of Formula ($I_S$):

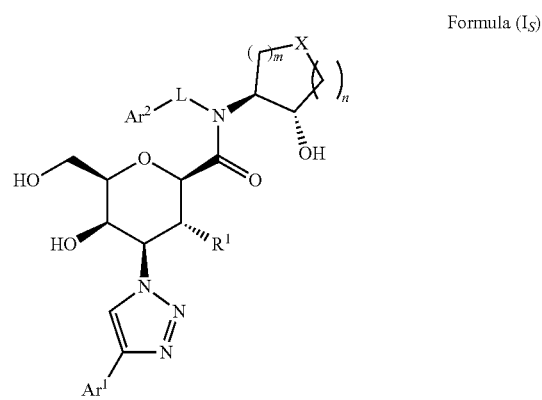

Formula ($I_S$)

or a pharmaceutically acceptable salt thereof.

3. The compound according to claim 1, wherein $Ar^1$ represents a phenyl which is di- or tri-substituted, wherein the substituents are independently selected from halogen, methyl, and cyano; wherein at least one of said substituents is attached in a meta- or in the para-position of said phenyl; or a pharmaceutically acceptable salt thereof.

4. The compound according to claim 1, wherein Ar$^1$ represents

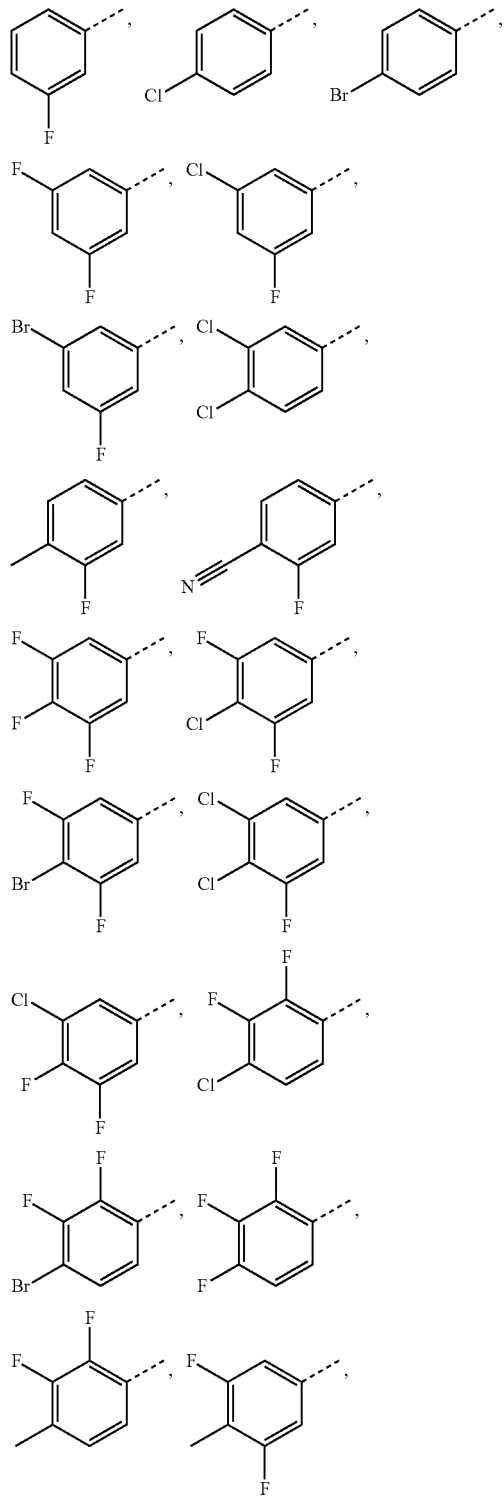

or a pharmaceutically acceptable salt thereof.

5. The compound according to claim 1, wherein R$^1$ represents methoxy; or a pharmaceutically acceptable salt thereof.

6. The compound according to claim 1, wherein L represents a direct bond; or a pharmaceutically acceptable salt thereof.

7. The compound according to claim 1, wherein Ar$^2$ represents phenyl which is mono-, or di-substituted, wherein the substituents are independently selected from $C_{1-4}$-alkyl, $C_{1-3}$-alkoxy, halogen, and cyano; or a pharmaceutically acceptable salt thereof.

8. The compound according to claim 1, wherein the fragment -L-Ar$^2$ represents:

or a pharmaceutically acceptable salt thereof.

9. A compound, wherein said compound is:
(2R,3R,4S,5R,6R)—N-(3-chlorophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)-5-hydroxy-6-(hydroxymethyl)-N-((3S,4R)-4-hydroxytetrahydrofuran-3-yl)-N-(3-iodophenyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3,5-dichlorophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-chloro-5-cyanophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3,5-dibromophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-cyanophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-cyano-5-methoxyphenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-cyano-5-methylphenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-cyano-5-fluorophenyl)-5-hydroxy-6-(hydroxymethyl)-N-((3S,4R)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)-4-(4-(4-bromo-2,3-difluorophenyl)-1H-1,2,3-triazol-1-yl)-N-(3,5-dichlorophenyl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)-4-(4-(4-bromo-2,3-difluorophenyl)-1H-1,2,3-triazol-1-yl)-N-(3-bromo-5-cyanophenyl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)-4-(4-(4-bromo-2,3-difluorophenyl)-1H-1,2,3-triazol-1-yl)-N-(3-bromo-5-methylphenyl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3,5-dichlorophenyl)-4-(4-(3,5-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3,5-dibromophenyl)-4-(4-(3,5-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(3,5-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(3,5-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3,5-dichlorophenyl)-4-(4-(2,3-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(2,3-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(2,3-difluoro-4-methylphenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)-4-(4-(4-chloro-3,5-difluorophenyl)-1H-1,2,3-triazol-1-yl)-N-(3,5-dichlorophenyl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)-4-(4-(4-chloro-3,5-difluorophenyl)-1H-1,2,3-triazol-1-yl)-N-(3,5-dibromophenyl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(4-chloro-3,5-difluorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(4-chloro-3,5-difluorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3,5-dichlorophenyl)-4-(4-(3,4-dichlorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3,5-dibromophenyl)-4-(4-(3,4-dichlorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(3,4-dichlorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(3,4-dichlorophenyl)-1H-1,2,3-triazol-1-yl)-5-hydroxy-6-(hydroxymethyl)-N-((3S,4R)-4-hydroxytetrahydrofuran-3-yl)-3-methoxytetrahydro-2H-pyran-2-carboxamide;

(2R,3R,4S,5R,6R)—N-(3-chlorophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)-5-hydroxy-6-(hydroxymethyl)-N-((3R,4S)-4-hydroxytetrahydrofuran-3-yl)-N-(3-iodophenyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3,5-dichlorophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-chloro-5-cyanophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3,5-dibromophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-cyanophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-cyano-5-methoxyphenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-cyano-5-methylphenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-cyano-5-fluorophenyl)-5-hydroxy-6-(hydroxymethyl)-N-((3R,4S)-4-hydroxytetrahydrofuran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)-4-(4-(4-bromo-2,3-difluorophenyl)-1H-1,2,3-triazol-1-yl)-N-(3,5-dichlorophenyl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)-4-(4-(4-bromo-2,3-difluorophenyl)-1H-1,2,3-triazol-1-yl)-N-(3-bromo-5-cyanophenyl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)-4-(4-(4-bromo-2,3-difluorophenyl)-1H-1,2,3-triazol-1-yl)-N-(3-bromo-5-methylphenyl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3,5-dichlorophenyl)-4-(4-(3,5-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3,5-dibromophenyl)-4-(4-(3,5-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(3,5-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(3,5-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3,5-dichlorophenyl)-4-(4-(2,3-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(2,3-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(2,3-difluoro-4-methylphenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)-4-(4-(4-chloro-3,5-difluorophenyl)-1H-1,2,3-triazol-1-yl)-N-(3,5-dichlorophenyl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)-4-(4-(4-chloro-3,5-difluorophenyl)-1H-1,2,3-triazol-1-yl)-N-(3,5-dibromophenyl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(4-chloro-3,5-difluorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(4-chloro-3,5-difluorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3,5-dichlorophenyl)-4-(4-(3,4-dichlorophenyl)-1H-1,2,3-triazol-1-yl)-5-hydroxy-6-

(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3,5-dibromophenyl)-4-(4-(3,4-dichlorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-cyanophenyl)-4-(4-(3,4-dichlorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3-bromo-5-methylphenyl)-4-(4-(3,4-dichlorophenyl)-1H-1,2,3-triazol-1-yl)-5-hydroxy-6-(hydroxymethyl)-N-((3R,4S)-4-hydroxytetrahydrofuran-3-yl)-3-methoxytetrahydro-2H-pyran-2-carboxamide;

(2R,3R,4S,5R,6R)—N-(3,5-dichlorophenyl)-5-hydroxy-6-(hydroxymethyl)-N-((3S,4S)-4-hydroxypyrrolidin-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-cyanophenyl)-5-hydroxy-6-(hydroxymethyl)-N-((3S,4S)-4-hydroxypyrrolidin-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-5-hydroxy-6-(hydroxymethyl)-N-((3S,4S)-4-hydroxypyrrolidin-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)-4-(4-(4-bromo-2,3-difluorophenyl)-1H-1,2,3-triazol-1-yl)-N-(3,5-dichlorophenyl)-5-hydroxy-6-(hydroxymethyl)-N-((3S,4S)-4-hydroxypyrrolidin-3-yl)-3-methoxytetrahydro-2H-pyran-2-carboxamide;

(2R,3R,4S,5R,6R)—N-(3,5-dichlorophenyl)-4-(4-(2,3-difluoro-4-methylphenyl)-1H-1,2,3-triazol-1-yl)-5-hydroxy-6-(hydroxymethyl)-N-((3S,4S)-4-hydroxypyrrolidin-3-yl)-3-methoxytetrahydro-2H-pyran-2-carboxamide;

(2R,3R,4S,5R,6R)—N-(3-bromo-5-methylphenyl)-4-(4-(2,3-difluoro-4-methylphenyl)-1H-1,2,3-triazol-1-yl)-5-hydroxy-6-(hydroxymethyl)-N-((3S,4S)-4-hydroxypyrrolidin-3-yl)-3-methoxytetrahydro-2H-pyran-2-carboxamide;

(2R,3R,4S,5R,6R)—N-(3,5-dichlorophenyl)-4-(4-(3,4-dichlorophenyl)-1H-1,2,3-triazol-1-yl)-5-hydroxy-6-(hydroxymethyl)-N-((3S,4S)-4-hydroxypyrrolidin-3-yl)-3-methoxytetrahydro-2H-pyran-2-carboxamide;

(2R,3R,4S,5R,6R)—N-(3,5-dichlorophenyl)-5-hydroxy-6-(hydroxymethyl)-N-((3R,4R)-4-hydroxypyrrolidin-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-cyanophenyl)-5-hydroxy-6-(hydroxymethyl)-N-((3R,4R)-4-hydroxypyrrolidin-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-5-hydroxy-6-(hydroxymethyl)-N-((3R,4R)-4-hydroxypyrrolidin-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-4-(4-(2,3-difluoro-4-methylphenyl)-1H-1,2,3-triazol-1-yl)-

5-hydroxy-6-(hydroxymethyl)-N-((3R,4R)-4-hydroxypyrrolidin-3-yl)-3-methoxytetrahydro-2H-pyran-2-carboxamide;

(2R,3R,4S,5R,6R)—N-(3-bromo-5-methylphenyl)-4-(4-(3,5-difluoro-4-methylphenyl)-1H-1,2,3-triazol-1-yl)-5-hydroxy-6-(hydroxymethyl)-N-(3S,4S)-4-hydroxypyrrolidin-3-yl)-3-methoxytetrahydro-2H-pyran-2-carboxamide;

(2R,3R,4S,5R,6R)—N-(3-bromo-5-methylphenyl)-4-(4-(3,5-difluoro-4-methylphenyl)-1H-1,2,3-triazol-1-yl)-5-hydroxy-6-(hydroxymethyl)-N-((3R,4R)-4-hydroxypyrrolidin-3-yl)-3-methoxytetrahydro-2H-pyran-2-carboxamide;

(2R,3R,4S,5R,6R)—N-((3S,4S)-1-acetyl-4-hydroxypyrrolidin-3-yl)-N-(3,5-dichlorophenyl)-5-hydroxy-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-((3S,4S)-1-acetyl-4-hydroxypyrrolidin-3-yl)-N-(3-bromo-5-methylphenyl)-5-hydroxy-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-((3S,4S)-1-acetyl-4-hydroxypyrrolidin-3-yl)-4-(4-(4-bromo-2,3-difluorophenyl)-1H-1,2,3-triazol-1-yl)-N-(3,5-dichlorophenyl)-5-hydroxy-6-(hydroxymethyl)-3-methoxytetrahydro-2H-pyran-2-carboxamide;

(2R,3R,4S,5R,6R)—N-((3S,4S)-1-acetyl-4-hydroxypyrrolidin-3-yl)-N-(3,5-dibromophenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3S,4S)-1-acetyl-4-hydroxypyrrolidin-3-yl)-N-(3-bromo-5-methylphenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3S,4S)-1-acetyl-4-hydroxypyrrolidin-3-yl)-N-(3-bromo-5-methylphenyl)-4-(4-(4-chloro-3,5-difluorophenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-N-(3,5-dichlorophenyl)-5-hydroxy-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-((3R,4R)-1-acetyl-4-hydroxypyrrolidin-3-yl)-N-(3-bromo-5-cyanophenyl)-5-hydroxy-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-((3R,4R)-1-acetyl-4-hydroxypyrrolidin-3-yl)-N-(3-bromo-5-methylphenyl)-5-hydroxy-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-((3R,4R)-1-acetyl-4-hydroxypyrrolidin-3-yl)-4-(4-(4-bromo-2,3-difluorophenyl)-1H-1,2,3-triazol-1-yl)-N-(3,5-dichlorophenyl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-N-(3,5-dibromophenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-N-(3-bromo-5-methylphenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-N-(3-bromo-5-methylphenyl)-4-(4-(4-chloro-3,5-difluorophenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3S,4S)-1-acetyl-4-hydroxypyrrolidin-3-yl)-N-(3,5-dibromophenyl)-5-hydroxy-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-((3R,4R)-1-acetyl-4-hydroxypyrrolidin-3-yl)-N-(3,5-dibromophenyl)-5-hydroxy-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-((3S,4S)-1-acetyl-4-hydroxypyrrolidin-3-yl)-N-(3,5-dichlorophenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-N-(3,5-dichlorophenyl)-4-(4-(3,5-difluoro-4-methylphenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3S,4S)-1-acetyl-4-hydroxypyrrolidin-3-yl)-4-(4-(4-chloro-3,5-difluorophenyl)-1H-1,2,3-triazol-1-yl)-N-(3,5-dichlorophenyl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-4-(4-(4-chloro-3,5-difluorophenyl)-1H-1,2,3-triazol-1-yl)-N-(3,5-dichlorophenyl)-5-hydroxy-6-(hydroxymethyl)-3-methoxytetrahydro-2H-pyran-2-carboxamide;

(2R,3R,4S,5R,6R)—N-(3S,4S)-1-acetyl-4-hydroxypyrrolidin-3-yl)-4-(4-(4-chloro-3,5-difluorophenyl)-1H-1,2,3-triazol-1-yl)-N-(3,5-dibromophenyl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-4-(4-(4-chloro-3,5-difluorophenyl)-1H-1,2,3-triazol-1-yl)-N-(3,5-dibromophenyl)-5-hydroxy-6-(hydroxymethyl)-3-methoxytetrahydro-2H-pyran-2-carboxamide;

(2R,3R,4S,5R,6R)—N-((3S,4S)-1-acetyl-4-hydroxypyrrolidin-3-yl)-N-(3,5-dichlorophenyl)-4-(4-(3,4-dichlorophenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-((3R,4R)-1-acetyl-4-hydroxypyrrolidin-3-yl)-N-(3,5-dichlorophenyl)-4-(4-(3,4-dichlorophenyl)-1H-1,2,3-triazol-1-yl)-5-hydroxy-6-(hydroxymethyl)-3-methoxytetrahydro-2H-pyran-2-carboxamide;

(2R,3R,4S,5R,6R)—N-(3-bromo-5-cyanophenyl)-N-((3S,4S)-1-formyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-N-((3S,4S)-1-formyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)-4-(4-(4-bromo-2,3-difluorophenyl)-1H-1,2,3-triazol-1-yl)-N-(3,5-dichlorophenyl)-N-((3S,4S)-1-formyl-4-hydroxypyrrolidin-3-yl)-5-hydroxy-6-(hydroxymethyl)-3-methoxytetrahydro-2H-pyran-2-carboxamide;

(2R,3R,4S,5R,6R)—N-(3-bromo-5-methylphenyl)-4-(4-(2,3-difluoro-4-methylphenyl)-1H-1,2,3-triazol-1-yl)-N-((3S,4S)-1-formyl-4-hydroxypyrrolidin-3-yl)-5-hydroxy-6-(hydroxymethyl)-3-methoxytetrahydro-2H-pyran-2-carboxamide;

(2R,3R,4S,5R,6R)—N-(3-bromo-5-cyanophenyl)-N-((3R,4R)-1-formyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-N-((3R,4R)-1-formyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-4-(4-(2,3-difluoro-4-methylphenyl)-1H-1,2,3-triazol-1-yl)-N-((3R,4R)-1-formyl-4-hydroxypyrrolidin-3-yl)-5-hydroxy-6-(hydroxymethyl)-3-methoxytetrahydro-2H-pyran-2-carboxamide;

(2R,3R,4S,5R,6R)—N-(3-bromo-5-methylphenyl)-5-hydroxy-N-((3S,4S)-4-hydroxy-1-methylpyrrolidin-3-yl)-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-N-((3S,4S)-1-ethyl-4-hydroxypyrrolidin-3-yl)-5-hydroxy-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-5-hydroxy-N-((3S,4S)-4-hydroxy-1-(methylsulfonyl) pyrrolidin-3-yl)-6-(hydroxymethyl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3,5-dichlorophenyl)-5-hydroxy-6-(hydroxymethyl)-N-((3R,4S)-3-hydroxytetrahydro-2H-pyran-4-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-chloro-5-cyanophenyl)-5-hydroxy-6-(hydroxymethyl)-N-((3R,4S)-3-hydroxytetrahydro-2H-pyran-4-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-cyanophenyl)-5-hydroxy-6-(hydroxymethyl)-N-((3R,4S)-3-hydroxytetrahydro-2H-pyran-4-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-5-hydroxy-6-(hydroxymethyl)-N-((3R,4S)-3-hydroxytetrahydro-2H-pyran-4-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3,5-dichlorophenyl)-5-hydroxy-6-(hydroxymethyl)-N-((3S,4R)-3-hydroxytetrahydro-2H-pyran-4-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-5-hydroxy-6-(hydroxymethyl)-N-((3S,4R)-3-hydroxytetrahydro-2H-pyran-4-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3,5-dichlorophenyl)-5-hydroxy-6-(hydroxymethyl)-N-((3S,4S)-4-hydroxytetrahydro-2H-pyran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-5-hydroxy-6-(hydroxymethyl)-N-((3S,4S)-4-hydroxytetrahydro-2H-pyran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3,5-dichlorophenyl)-5-hydroxy-6-(hydroxymethyl)-N-((3R,4R)-4-hydroxytetrahydro-2H-pyran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-5-hydroxy-6-(hydroxymethyl)-N-((3R,4R)-4-hydroxytetrahydro-2H-pyran-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3,5-dichlorophenyl)-5-hydroxy-6-(hydroxymethyl)-N-((3S,4S)-3-hydroxypiperidin-4-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-cyanophenyl)-5-hydroxy-6-(hydroxymethyl)-N-((3S,4S)-3-hydroxypiperidin-4-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-5-hydroxy-6-(hydroxymethyl)-N-((3S,4S)-3-hydroxypiperidin-4-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-5-hydroxy-6-(hydroxymethyl)-N-((3R,4R)-3-hydroxypiperidin-4-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3,5-dichlorophenyl)-5-hydroxy-6-(hydroxymethyl)-N-((3S,4S)-4-hydroxypiperidin-3-yl)-3-methoxy-4-(4-(3,4,5-trifluorophenyl)-1H-1,2,3-triazol-1-yl) tetrahydro-2H-pyran-2-carboxamide;

(2R,3R,4S,5R,6R)—N-(3-bromo-5-methylphenyl)-5-hydroxy-6-(hydroxymethyl)-N-((3S,4S)-4-hydroxypiperidin-3-yl)-3-methoxy-4-(4-(3,4,5-trifluorophenyl)-1H-1,2,3-triazol-1-yl) tetrahydro-2H-pyran-2-carboxamide; or (2R,3R,4S,5R,6R)—N-(3-bromo-5-methylphenyl)-5-hydroxy-6-(hydroxymethyl)-N-((3R,4R)-4-hydroxypiperidin-3-yl)-3-methoxy-4-(4-(3,4,5-trifluorophenyl)-1H-1,2,3-triazol-1-yl) tetrahydro-2H-pyran-2-carboxamide;

or a pharmaceutically acceptable salt thereof.

10. A pharmaceutical composition comprising a compound according to claim 1, or a pharmaceutically acceptable salt thereof, and a pharmaceutically acceptable carrier.

11. A method for the treatment of an indication selected from fibrosis of organs; liver diseases and disorders; acute kidney injury and chronic kidney disease; cardiovascular diseases and disorders; interstitial lung diseases and disorders; cell proliferative diseases and cancers; inflammatory and autoimmune diseases and disorders; gastrointestinal tract diseases and disorders; pancreatic diseases and disorders; abnormal angiogenesis-associated diseases and disorders; brain-associated diseases and disorders; neuropathic pain and peripheral neuropathy; ocular diseases and disorders; and transplant rejection; comprising administering to a subject in a need thereof an effective amount of a compound as defined in claim 1, or of a pharmaceutically acceptable salt thereof.

12. A pharmaceutical composition comprising a compound according to claim 9, or a pharmaceutically acceptable salt thereof, and a pharmaceutically acceptable carrier.

13. A method for the treatment of an indication selected from fibrosis of organs; liver diseases and disorders; acute kidney injury and chronic kidney disease; cardiovascular diseases and disorders; interstitial lung diseases and disorders; cell proliferative diseases and cancers; inflammatory and autoimmune diseases and disorders; gastrointestinal tract diseases and disorders; pancreatic diseases and disorders; abnormal angiogenesis-associated diseases and disorders; brain-associated diseases and disorders; neuropathic pain and peripheral neuropathy; ocular diseases and disorders; and transplant rejection; comprising administering to a subject in a need thereof an effective amount of a compound as defined in claim 9, or of a pharmaceutically acceptable salt thereof.

\* \* \* \* \*